United States Patent
Atto et al.

(10) Patent No.: US 11,337,727 B2
(45) Date of Patent: May 24, 2022

(54) RADIALLY EXPANDABLE CANNULA DEVICES, AND SYSTEMS AND METHODS FOR USING THEM

(71) Applicant: XPAN Inc., Nobleton (CA)

(72) Inventors: Zaid Atto, Nobleton (CA); Amanda Manget, Toronto (CA)

(73) Assignee: XPAN Inc., Nobleton (CA)

( * ) Notice: Subject to any disclaimer, the term of this patent is extended or adjusted under 35 U.S.C. 154(b) by 0 days.

(21) Appl. No.: 17/534,314

(22) Filed: Nov. 23, 2021

(65) Prior Publication Data

US 2022/0079622 A1 Mar. 17, 2022

Related U.S. Application Data

(63) Continuation of application No. PCT/IB2021/000199, filed on Mar. 12, 2021.
(Continued)

(51) Int. Cl.
*A61B 17/34* (2006.01)
*A61B 34/30* (2016.01)

(52) U.S. Cl.
CPC ...... *A61B 17/3431* (2013.01); *A61B 17/3462* (2013.01); *A61B 17/3474* (2013.01);
(Continued)

(58) Field of Classification Search
CPC ............ A61B 17/3423; A61B 17/3431; A61B 17/3439; A61B 17/3462; A61B 17/3474; A61B 17/3496; A61B 17/3498; A61B 2017/34333; A61B 2017/445; A61B 2017/3447; A61B 2017/3449;
(Continued)

(56) References Cited

U.S. PATENT DOCUMENTS

| 3,509,883 A | 5/1970 | Dibelius |
| 3,789,852 A | 2/1974 | Kim |

(Continued)

FOREIGN PATENT DOCUMENTS

| CA | 2052310 A1 | 4/1992 |
| CA | 2550605 A1 | 7/2005 |

(Continued)

*Primary Examiner* — Robert A Lynch
(74) *Attorney, Agent, or Firm* — William A. English; Vista IP Law Group LLP

(57) ABSTRACT

Cannula devices, systems, and methods are provided for introducing one or more instruments into a patient's body to perform a procedure. In one example, the cannula device includes first and second housings defining a throughbore, and a plurality of elongate members extending distally from the housings, the elongate members cooperatively defining a passage axially aligned with the throughbore between proximal ends and distal tips of the elongate members. The first housing is moveable in an axial direction with respect to the second housing to cause the proximal ends of the elongate members to move outwardly to increase a size of the passage and, optionally, may taper when expanded. Optionally, one or more secondary devices, e.g., an obturator with a sharpened tip, or an obturator and tubular access device may be provided that may be inserted through the throughbore into the passage before expansion of the passage.

30 Claims, 35 Drawing Sheets

Related U.S. Application Data

(60) Provisional application No. 62/989,520, filed on Mar. 13, 2020.

(52) U.S. Cl.
CPC ...... *A61B 17/3496* (2013.01); *A61B 17/3498* (2013.01); *A61B 34/30* (2016.02)

(58) Field of Classification Search
CPC ...... A61B 2017/345; A61B 2017/3464; A61B 2017/3466; A61B 34/30; A61M 39/06; A61M 39/02; A61M 2039/062; A61M 2039/0626; A61M 2039/0633; A61M 2039/0673; A61M 2039/0686
See application file for complete search history.

(56) References Cited

U.S. PATENT DOCUMENTS

| | | |
|---|---|---|
| 4,716,901 A | 1/1988 | Jackson |
| 4,899,729 A | 2/1990 | Gill |
| 5,122,122 A | 6/1992 | Allgood |
| 5,139,511 A | 8/1992 | Gill |
| 5,183,464 A | 2/1993 | Dubrul |
| 5,197,971 A | 3/1993 | Bonutti |
| 5,295,994 A | 3/1994 | Bonutti |
| 5,312,417 A | 5/1994 | Wilk |
| 5,338,305 A | 8/1994 | Plyley |
| 5,916,232 A | 6/1999 | Hart |
| 5,944,691 A | 8/1999 | Quers |
| 7,896,897 B2 | 3/2011 | Gresham |
| 8,292,851 B2 | 10/2012 | Ferrari |
| 8,518,087 B2 | 8/2013 | Lopez |
| 8,591,538 B2 | 11/2013 | Gellman |
| 2003/0014068 A1 | 1/2003 | Bonutti |
| 2003/0023259 A1 | 1/2003 | Dubrul |
| 2004/0116954 A1 | 6/2004 | Pagliuca |
| 2006/0206008 A1 | 9/2006 | Dalton |
| 2006/0212062 A1 | 9/2006 | Farascioni |
| 2007/0010716 A1* | 1/2007 | Malandain ............. A61B 90/30 600/219 |
| 2009/0024158 A1 | 1/2009 | Viker |
| 2009/0209913 A1 | 8/2009 | Ferrari |
| 2009/0306586 A1 | 10/2009 | Ross et al. |
| 2012/0172668 A1 | 7/2012 | Kerns |
| 2013/0103048 A1 | 4/2013 | Burg et al. |
| 2014/0276584 A1 | 9/2014 | Castro |
| 2020/0261115 A1 | 8/2020 | Atto et al. |

FOREIGN PATENT DOCUMENTS

| | | | |
|---|---|---|---|
| CA | 2698872 A1 | 10/2010 | |
| CA | 2993590 A1 * | 3/2019 | ......... A61B 17/3423 |
| CN | 107049440 A | 8/2017 | |
| KR | 101287138 B1 | 7/2013 | |
| WO | 2005089433 A2 | 9/2005 | |
| WO | 2007056627 A1 | 5/2007 | |
| WO | 2008121794 A1 | 10/2008 | |
| WO | 2010080497 A2 | 7/2010 | |
| WO | 2011072098 A2 | 6/2011 | |
| WO | 2011130532 A2 | 10/2011 | |
| WO | 2013119577 A1 | 8/2013 | |
| WO | 2015040617 A1 | 3/2015 | |
| WO | 2017040275 A1 | 3/2017 | |

* cited by examiner

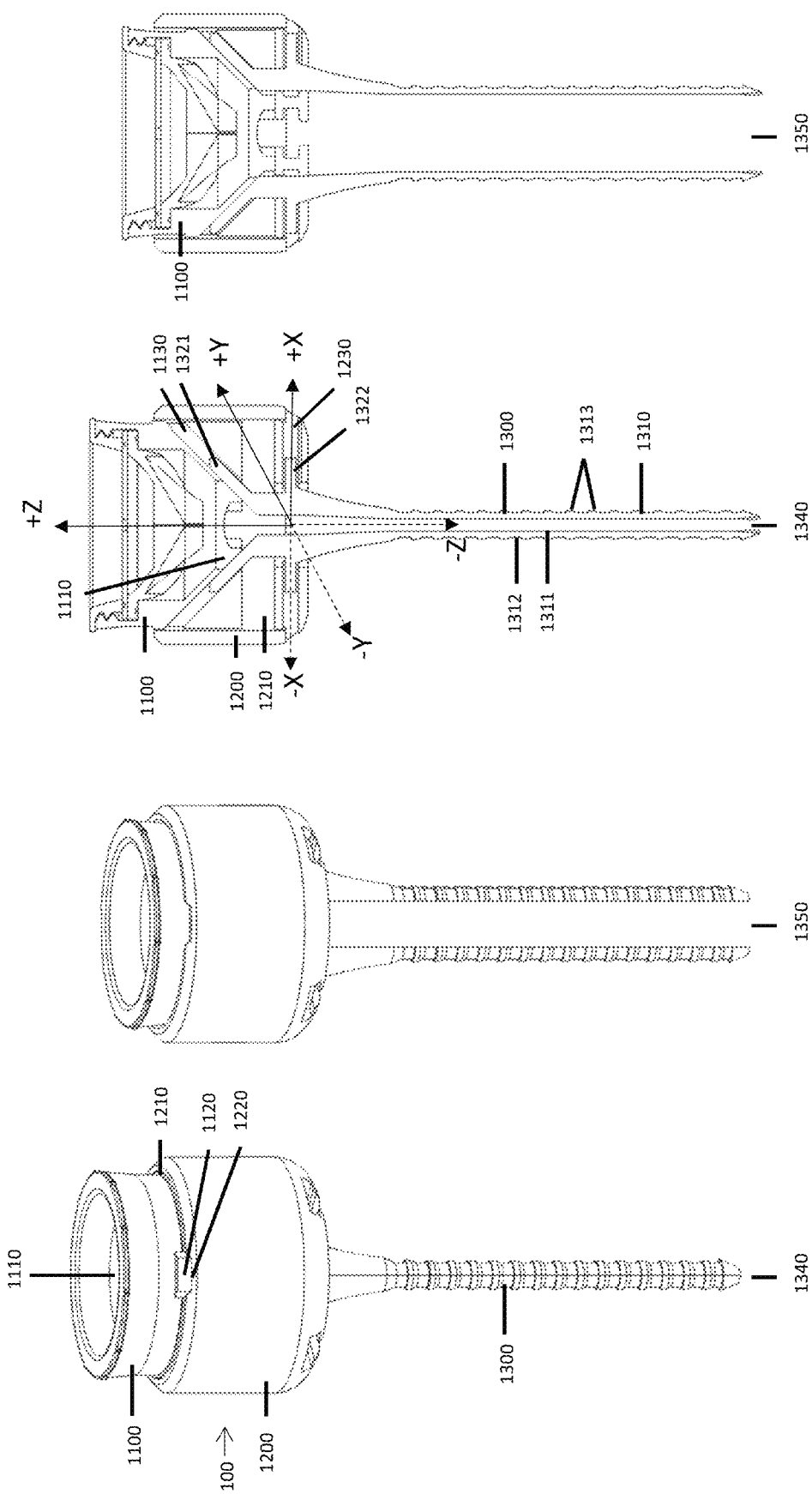

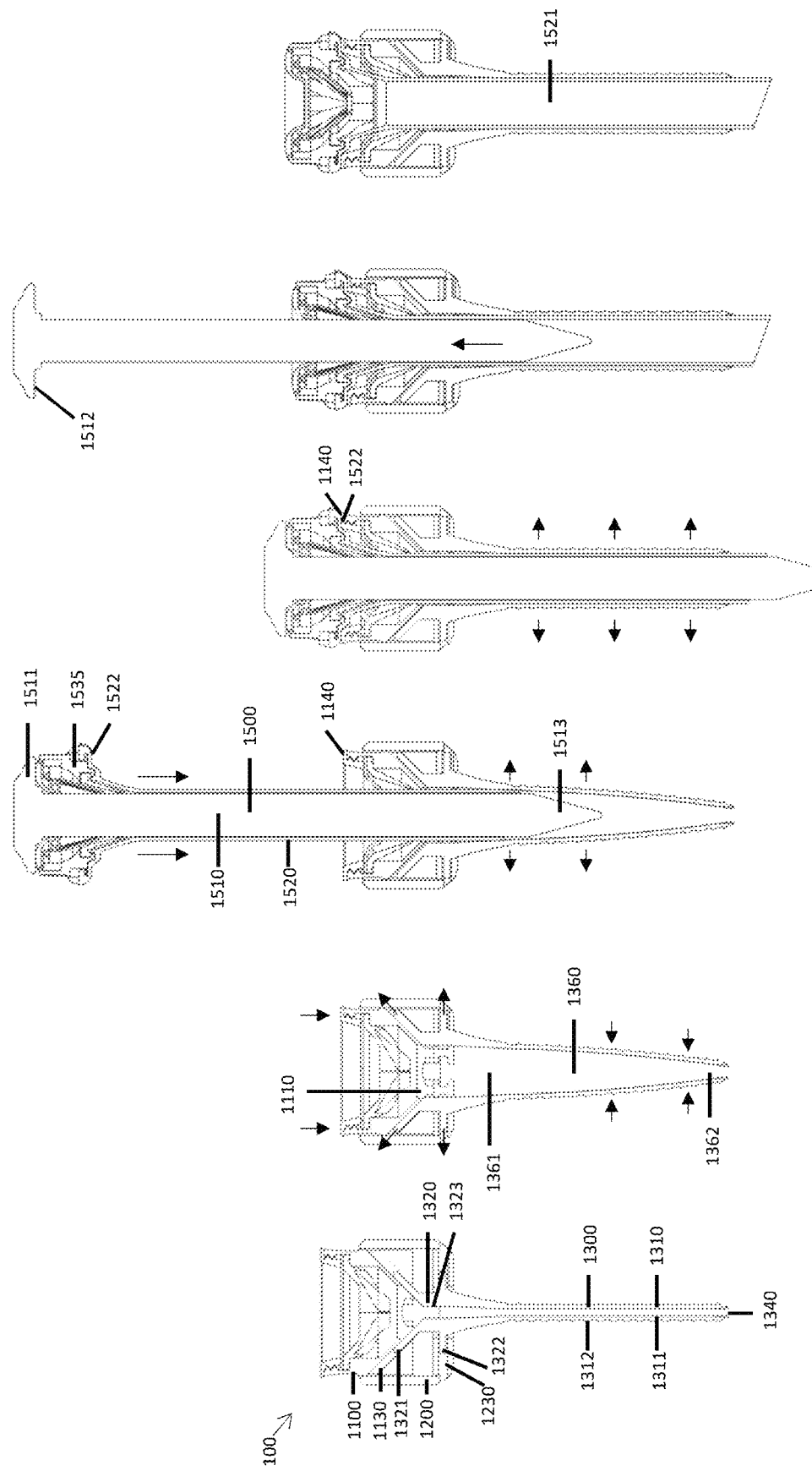

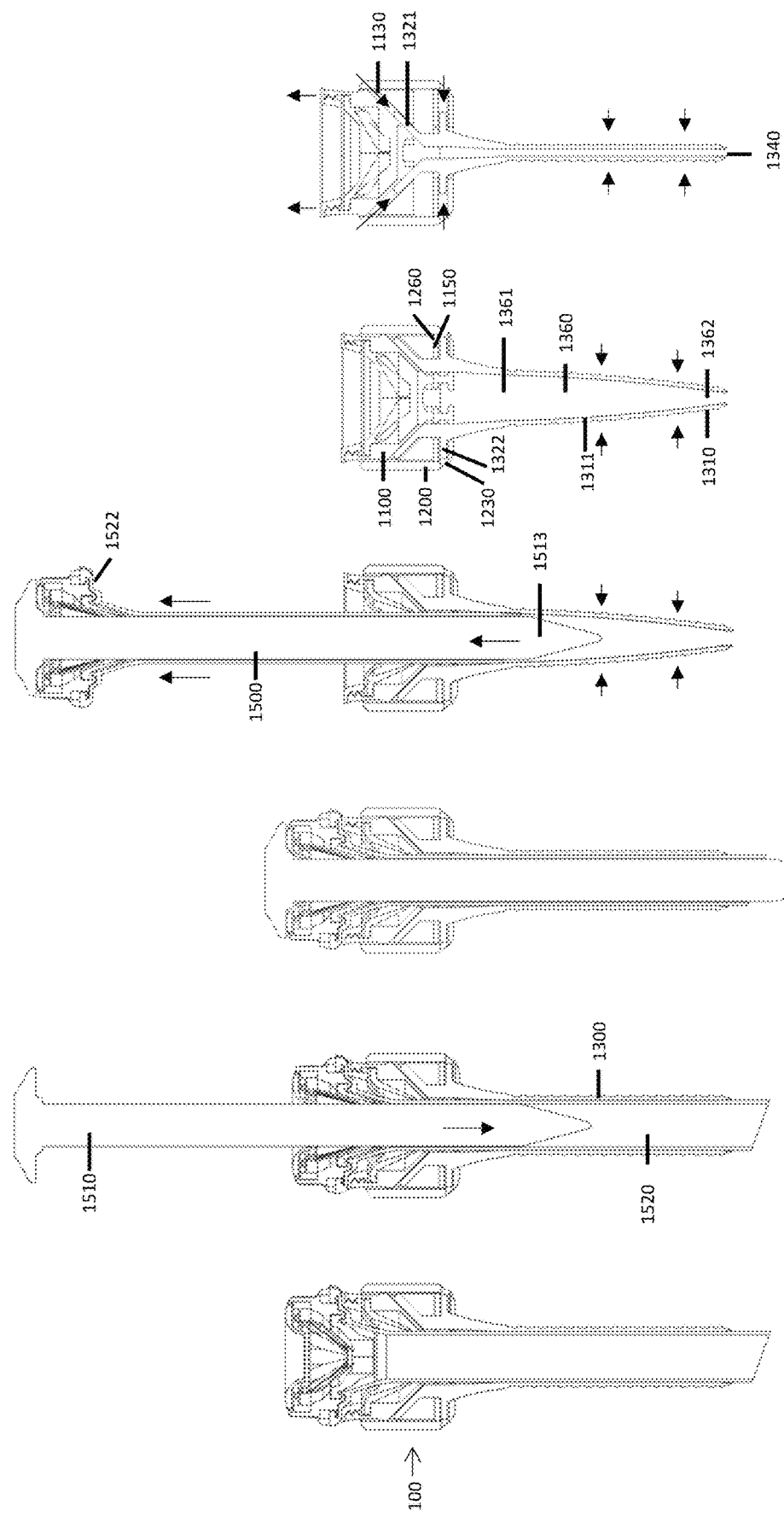

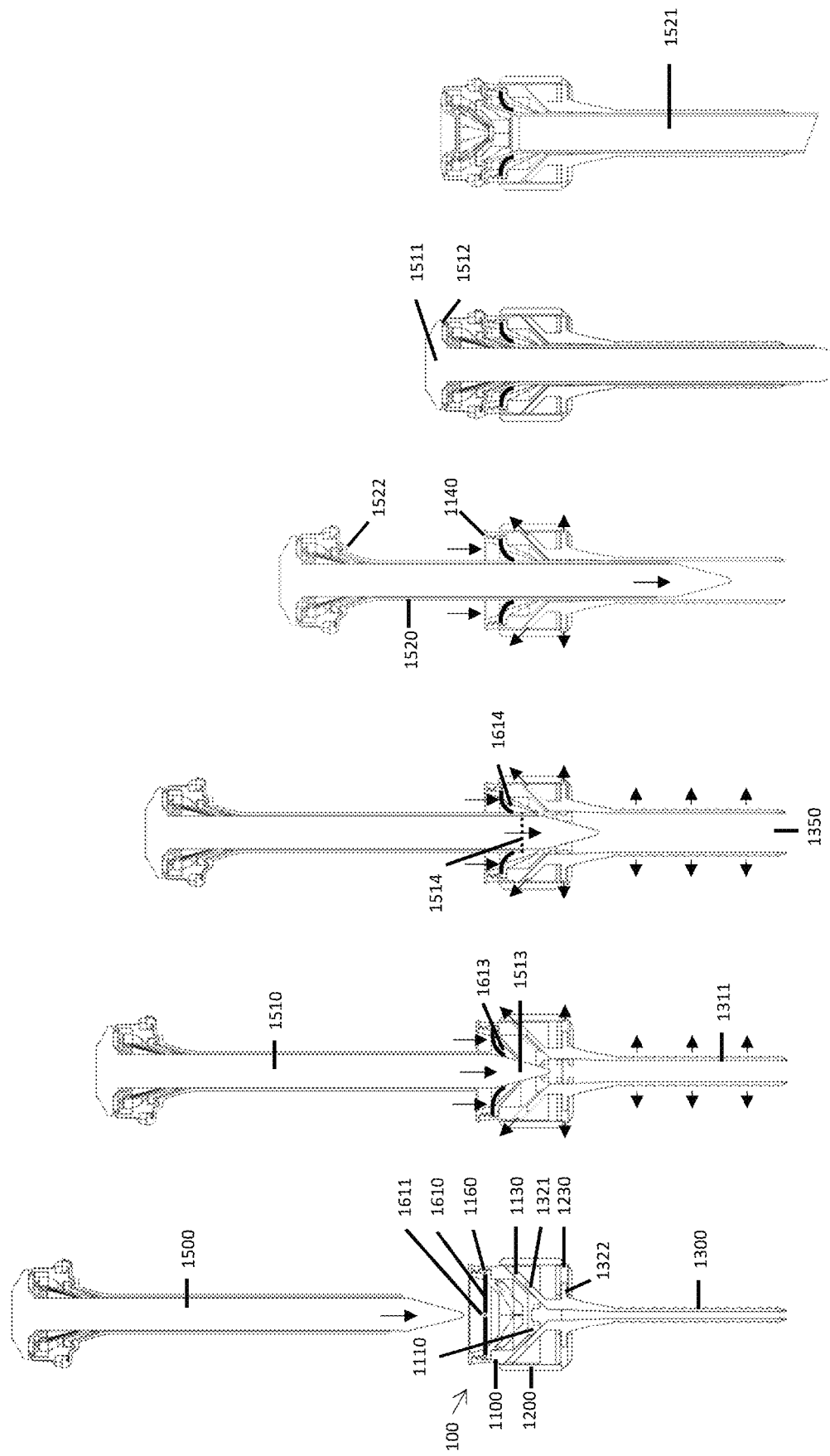

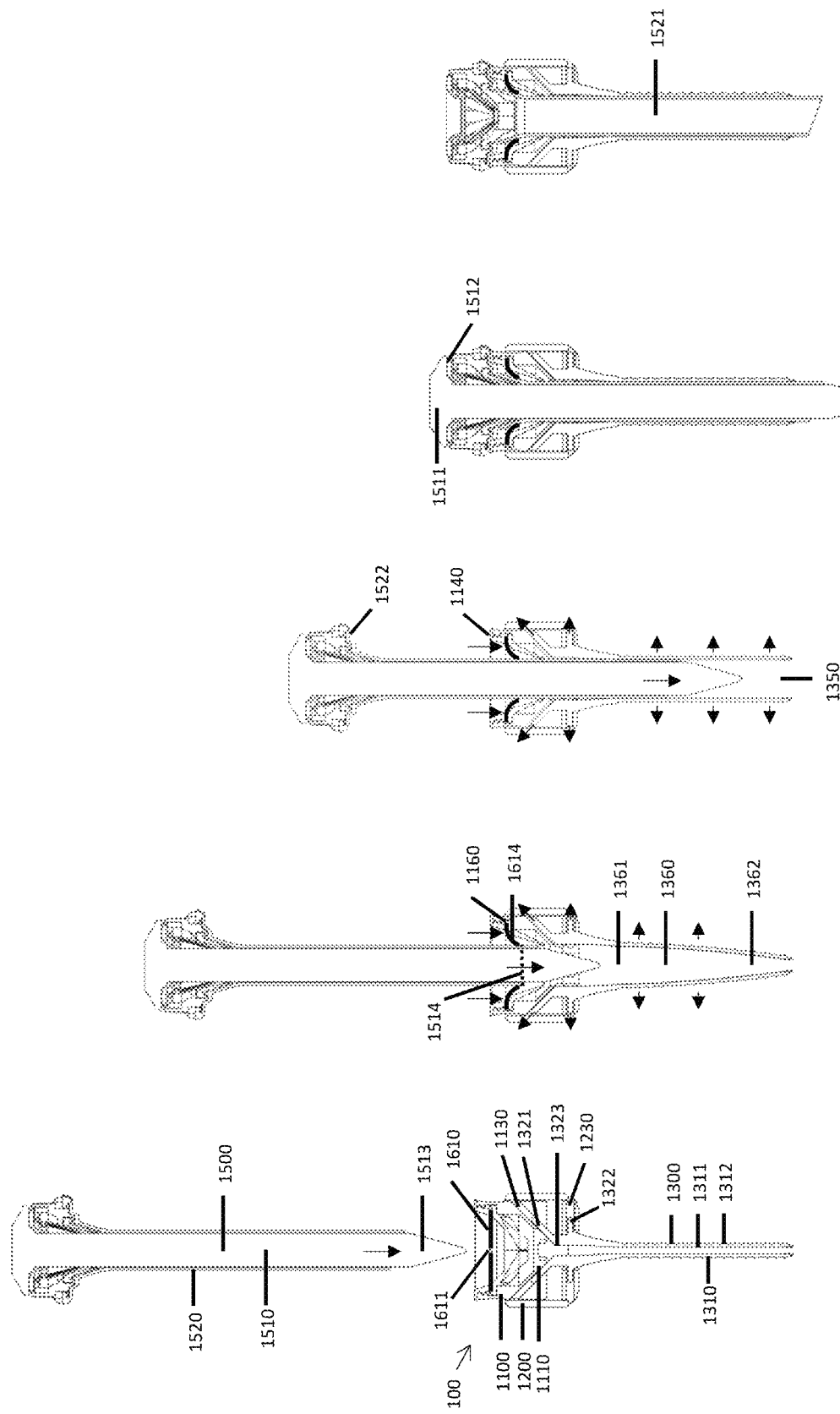

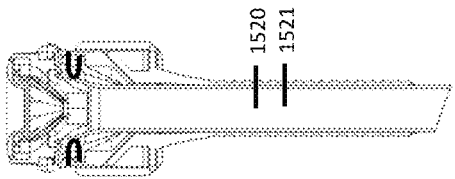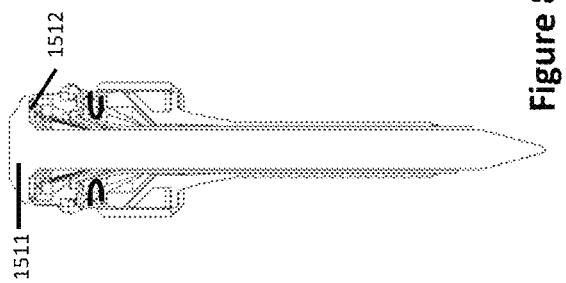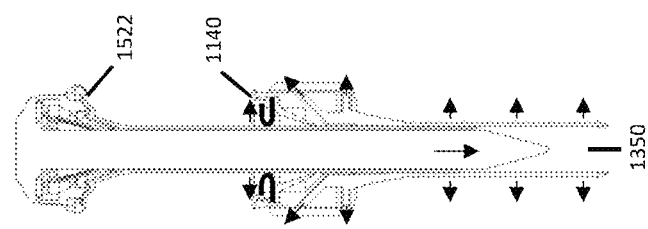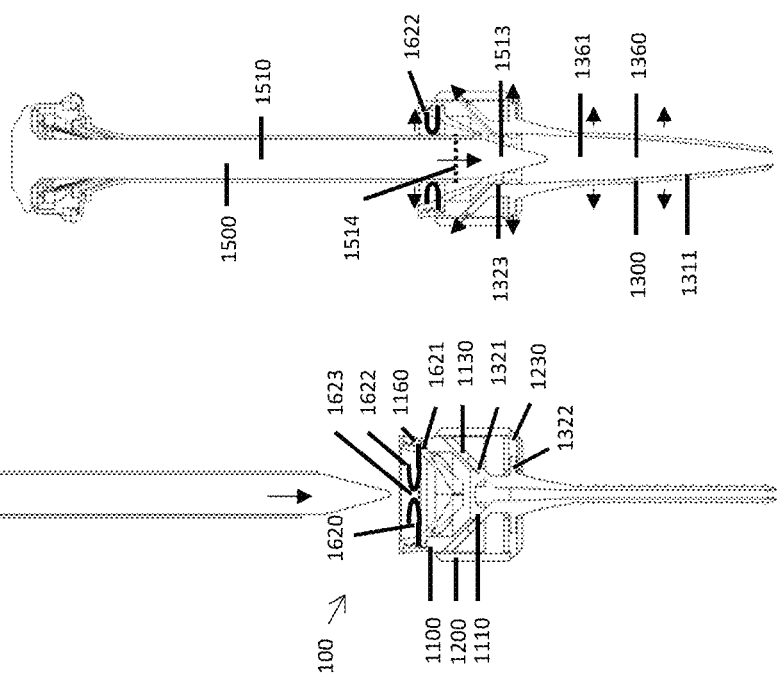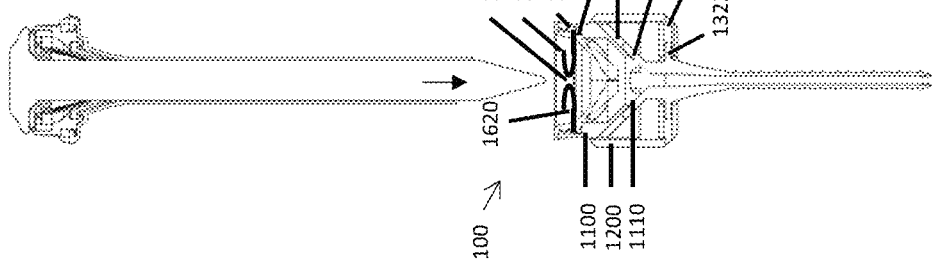

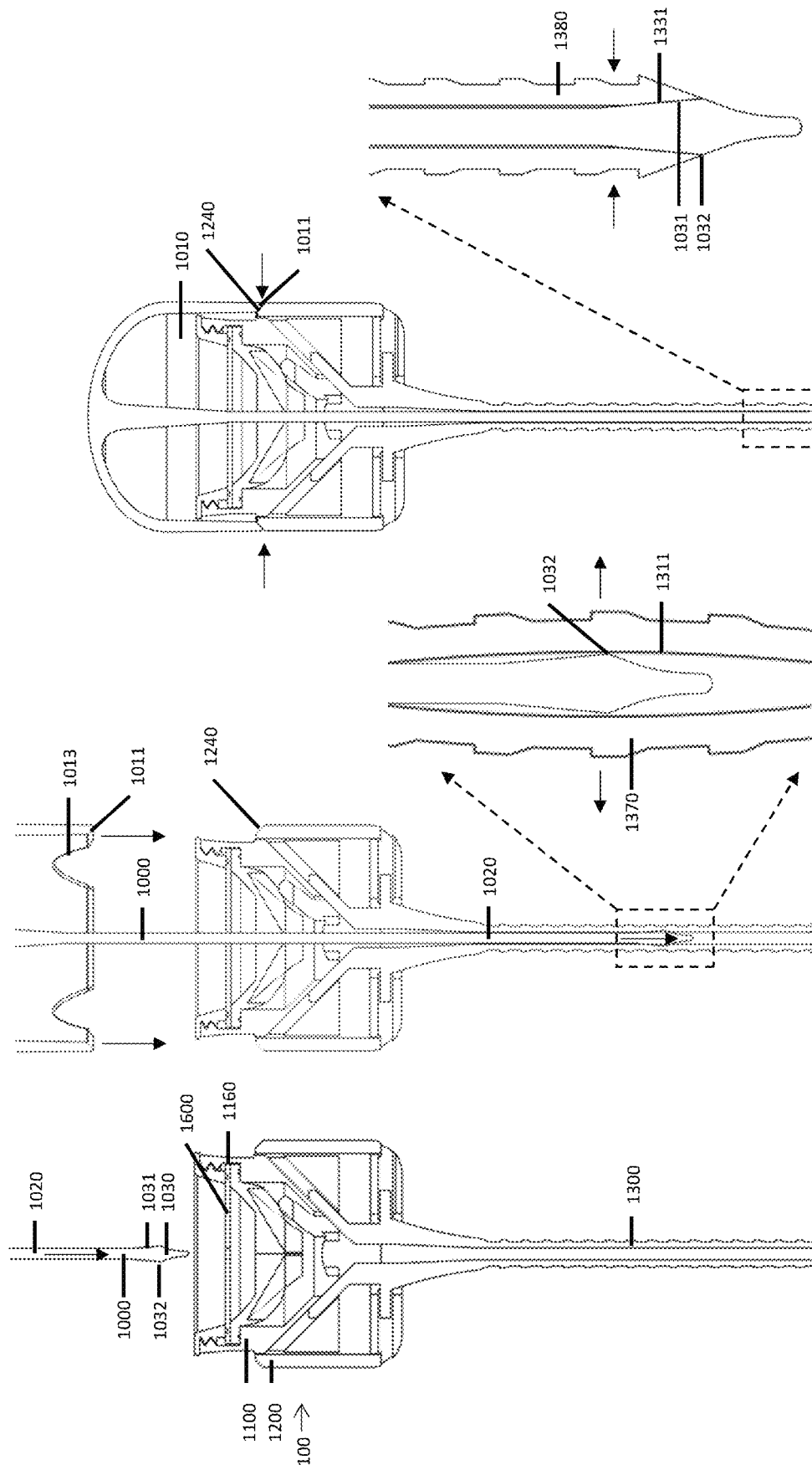

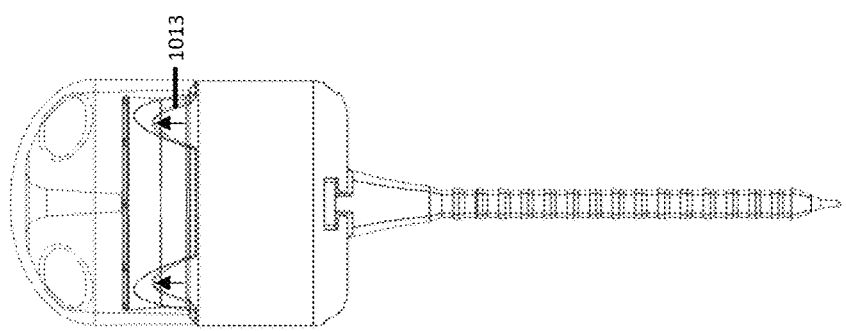
Figure 11E
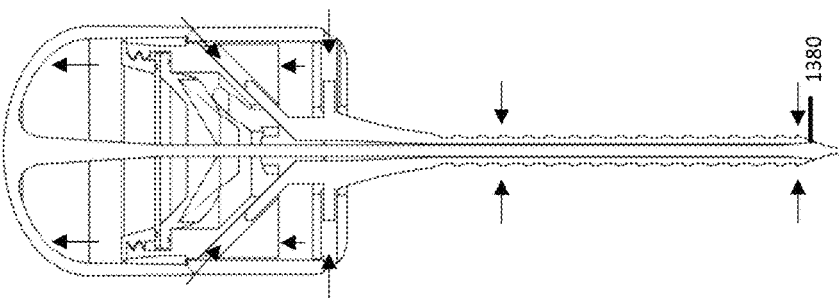
Figure 11D
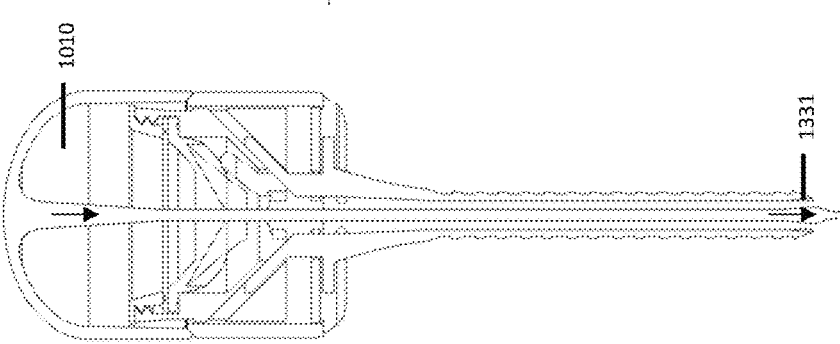
Figure 11C
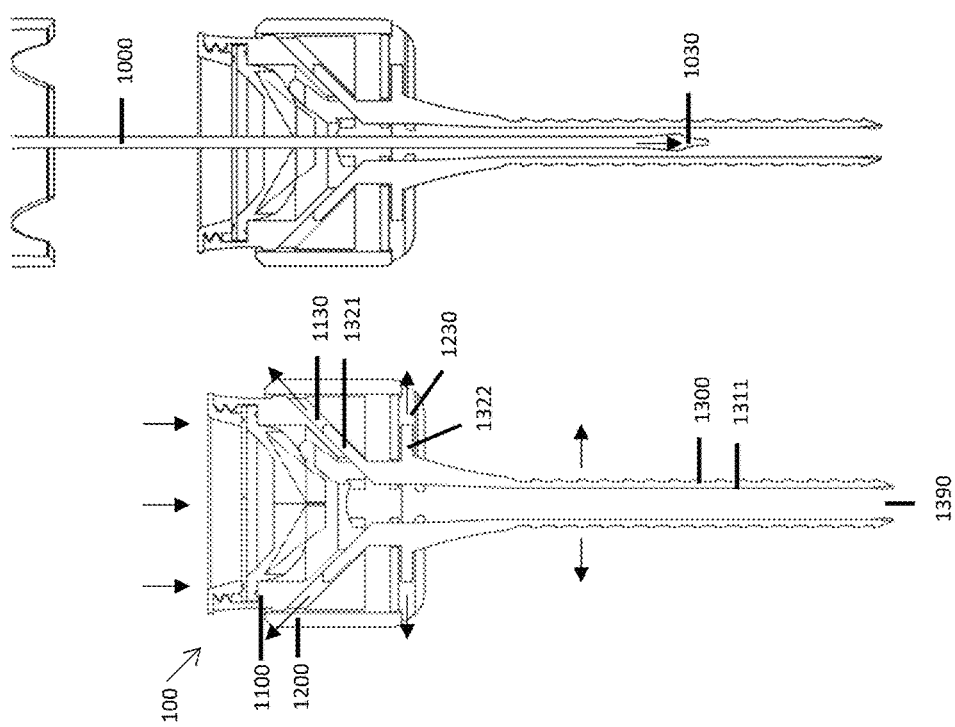
Figure 11B
Figure 11A

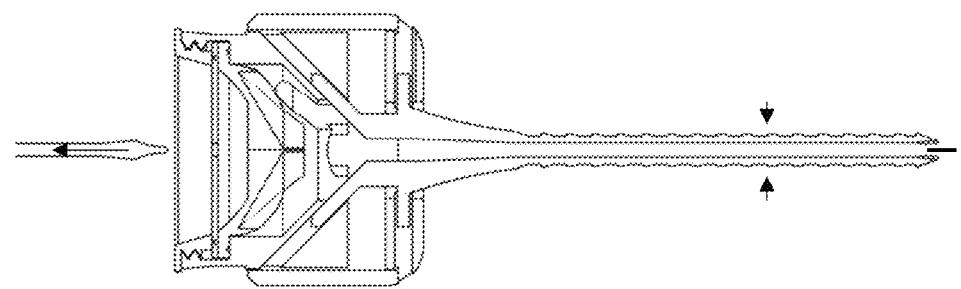
Figure 12D
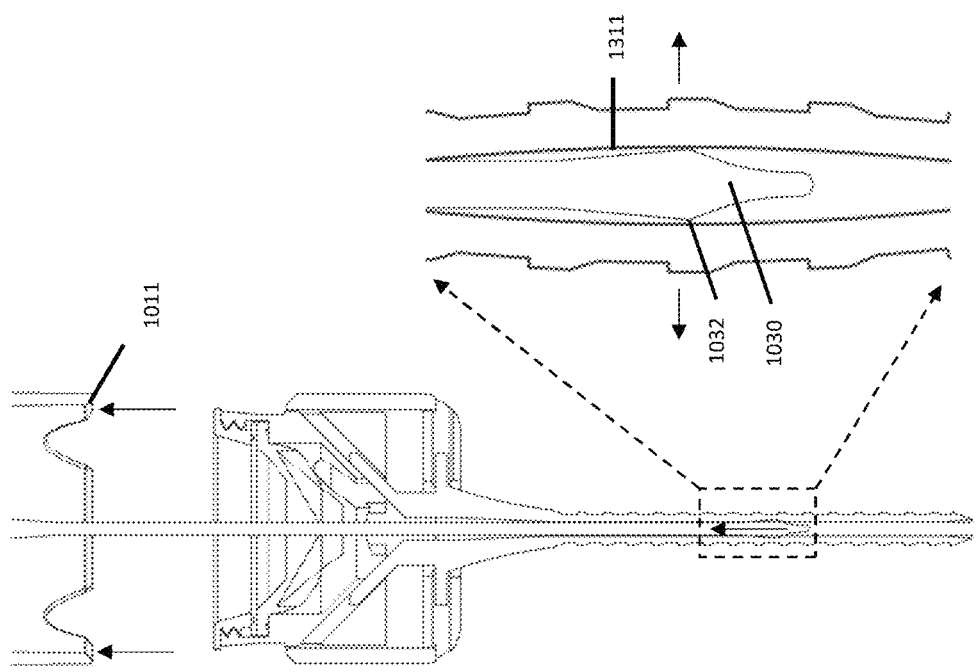
Figure 12C
Figure 12B
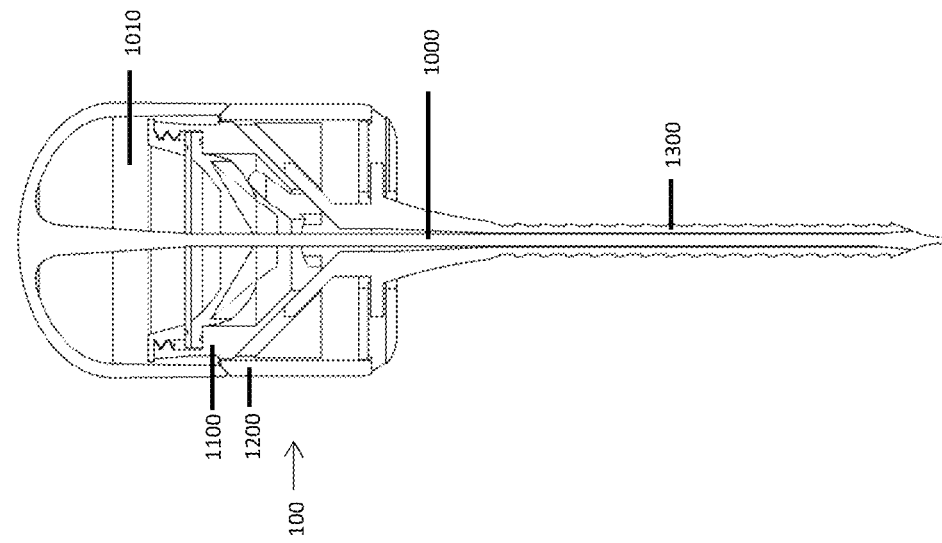
Figure 12A

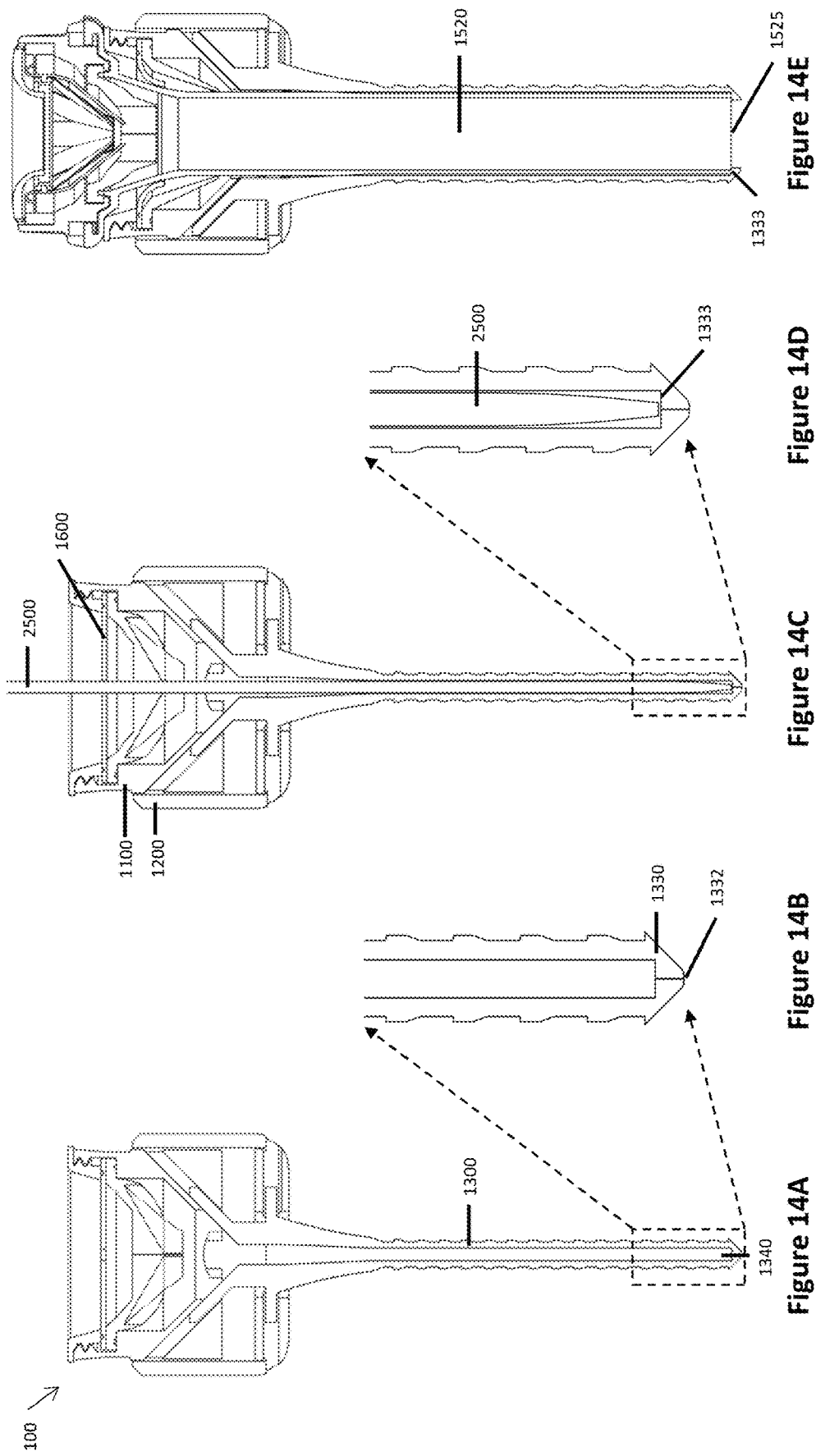

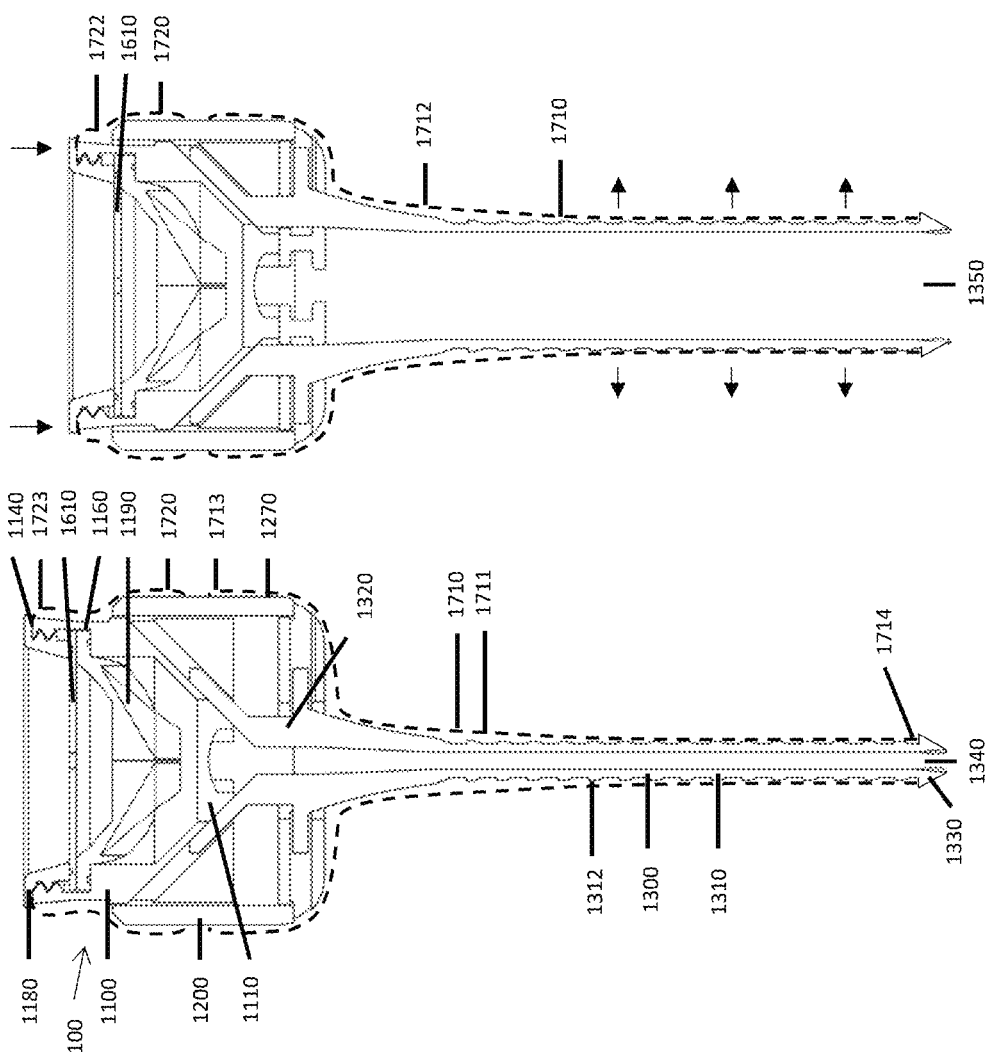

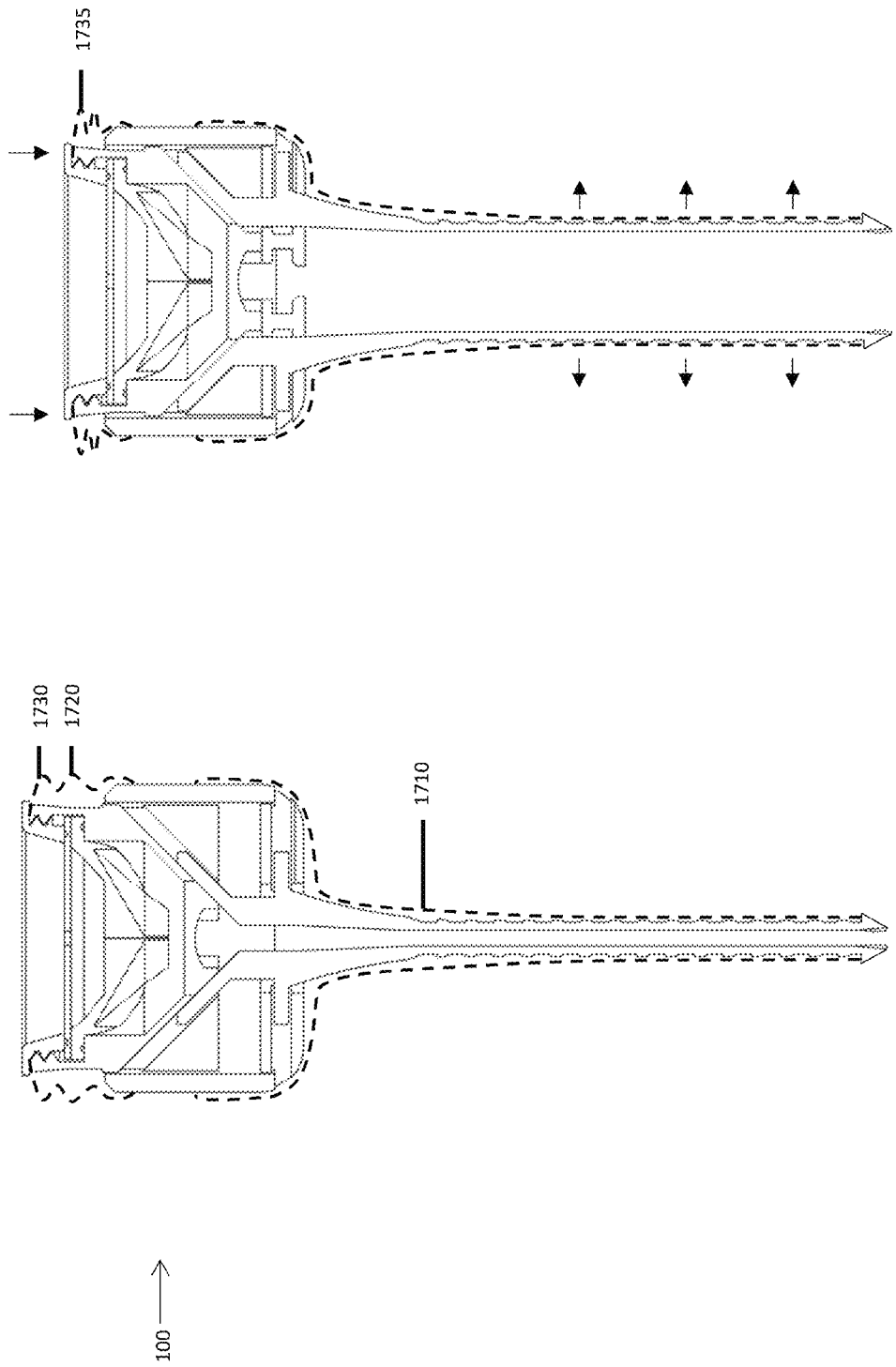

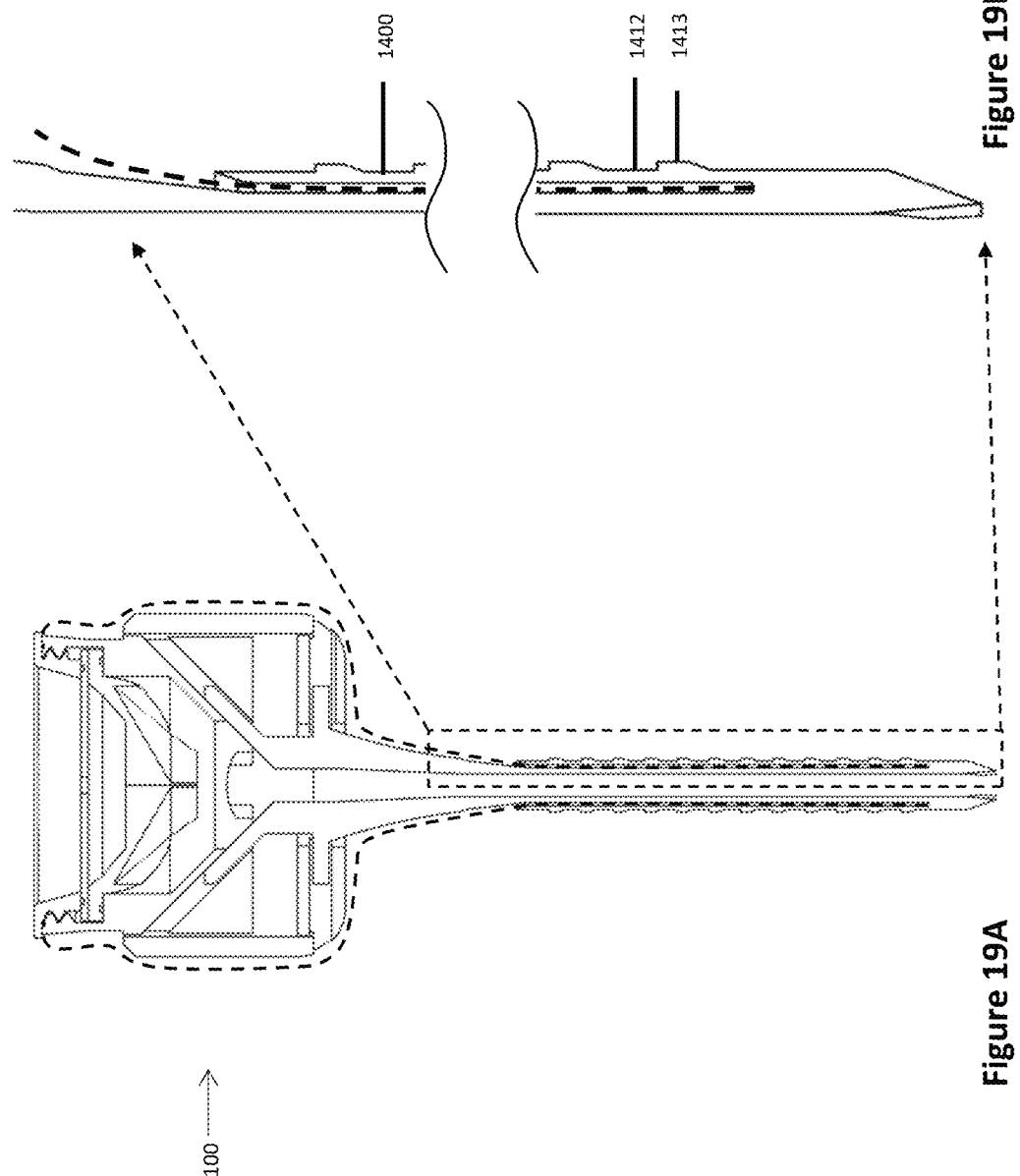

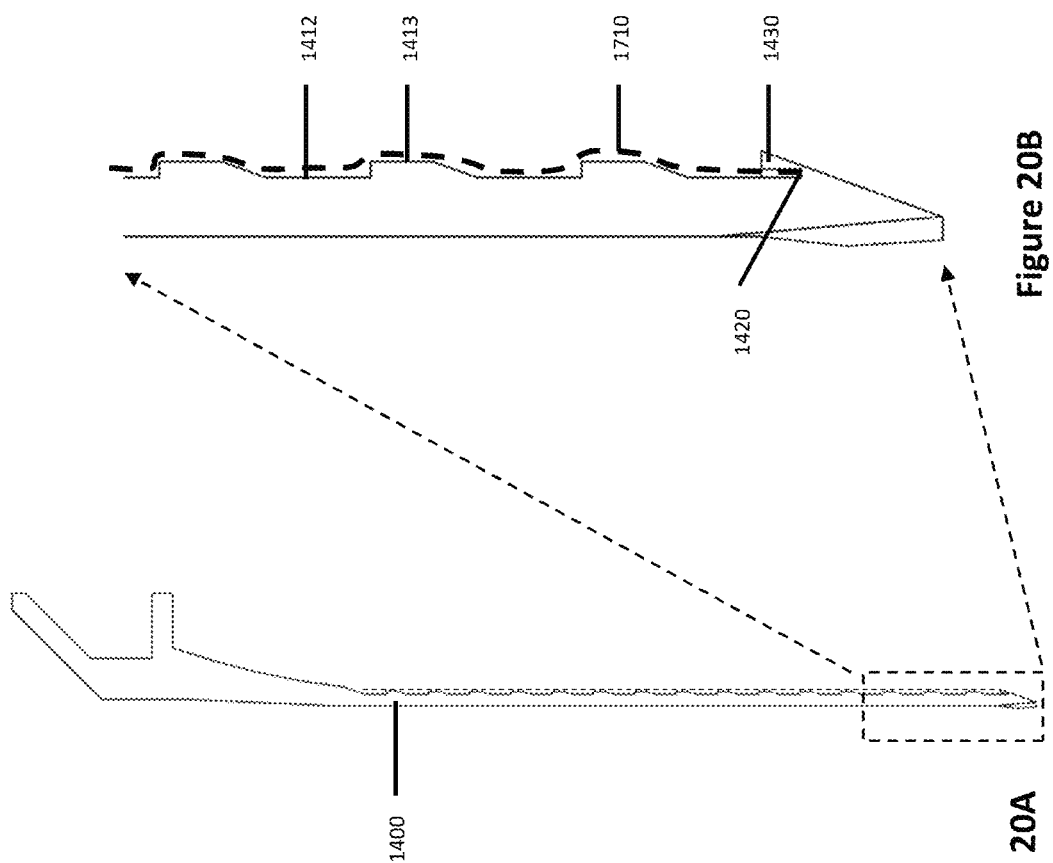

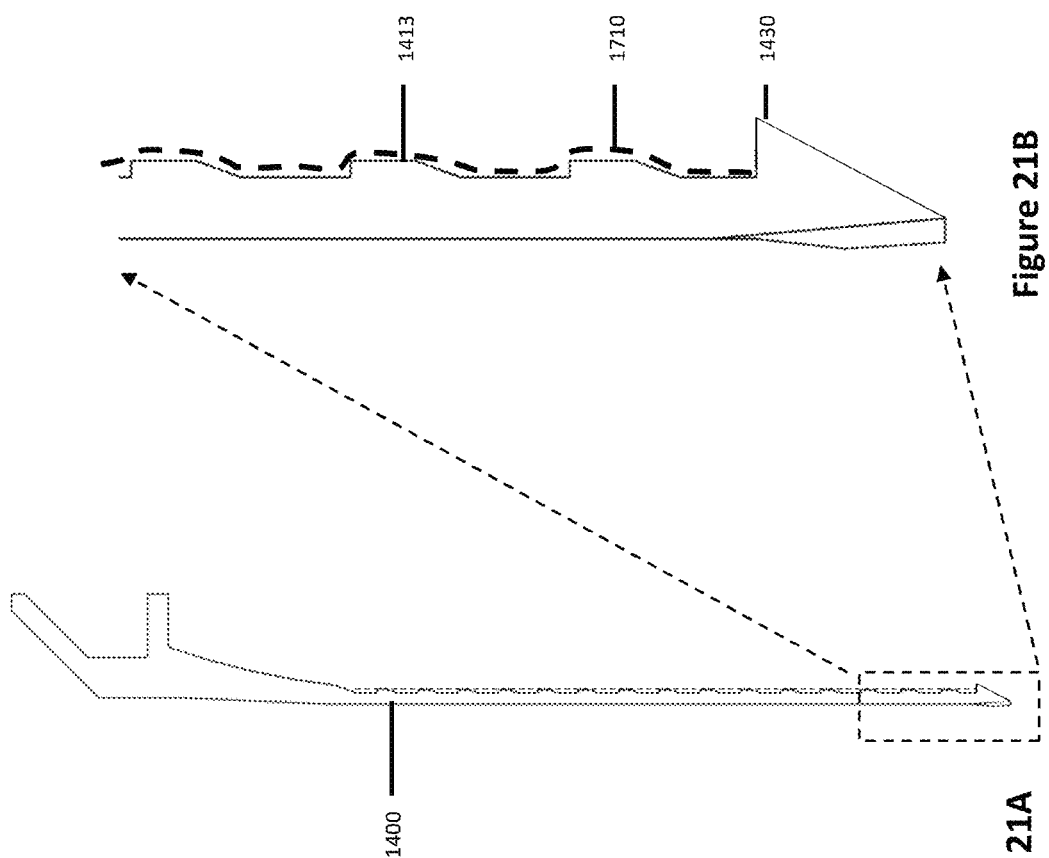

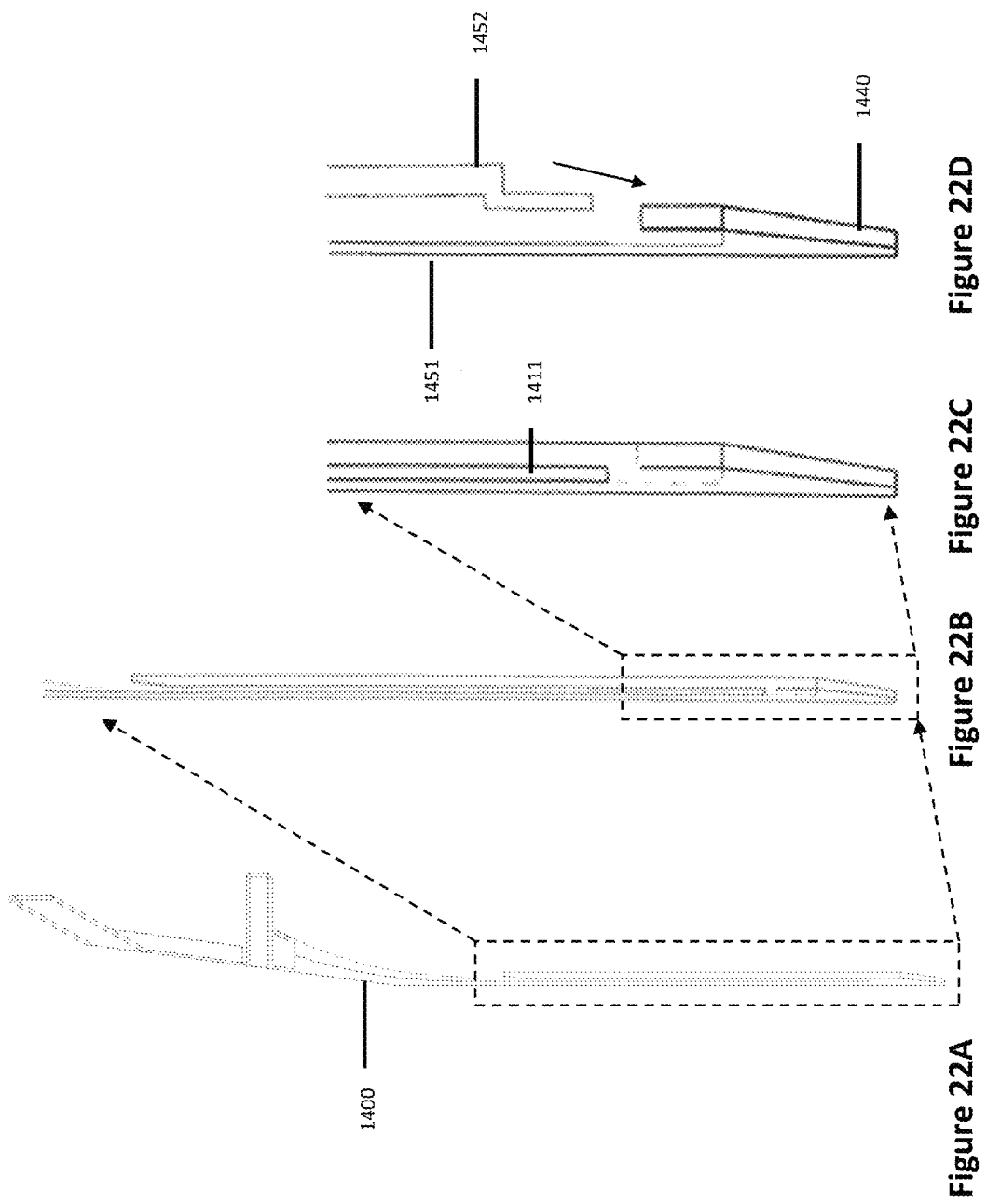

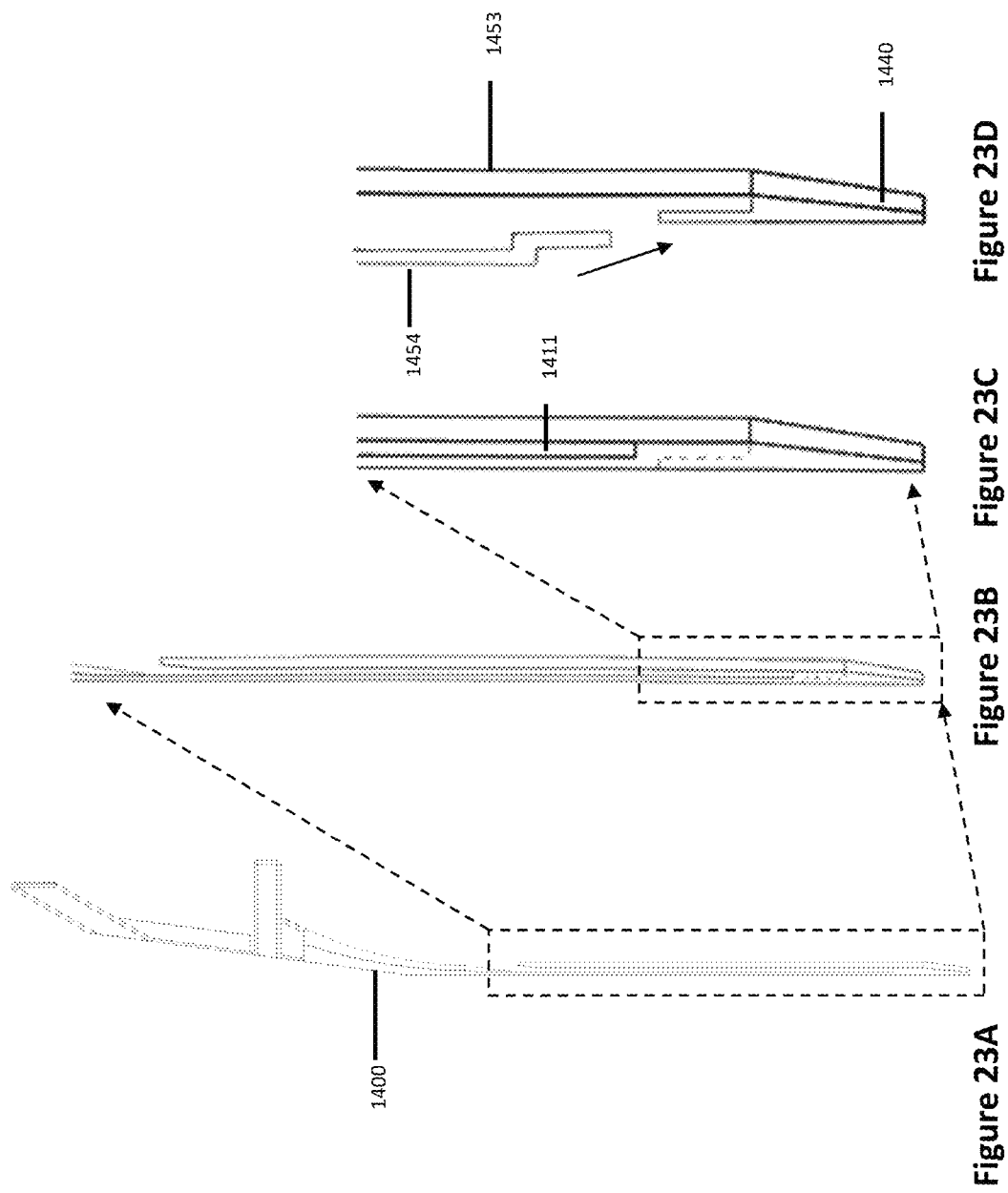

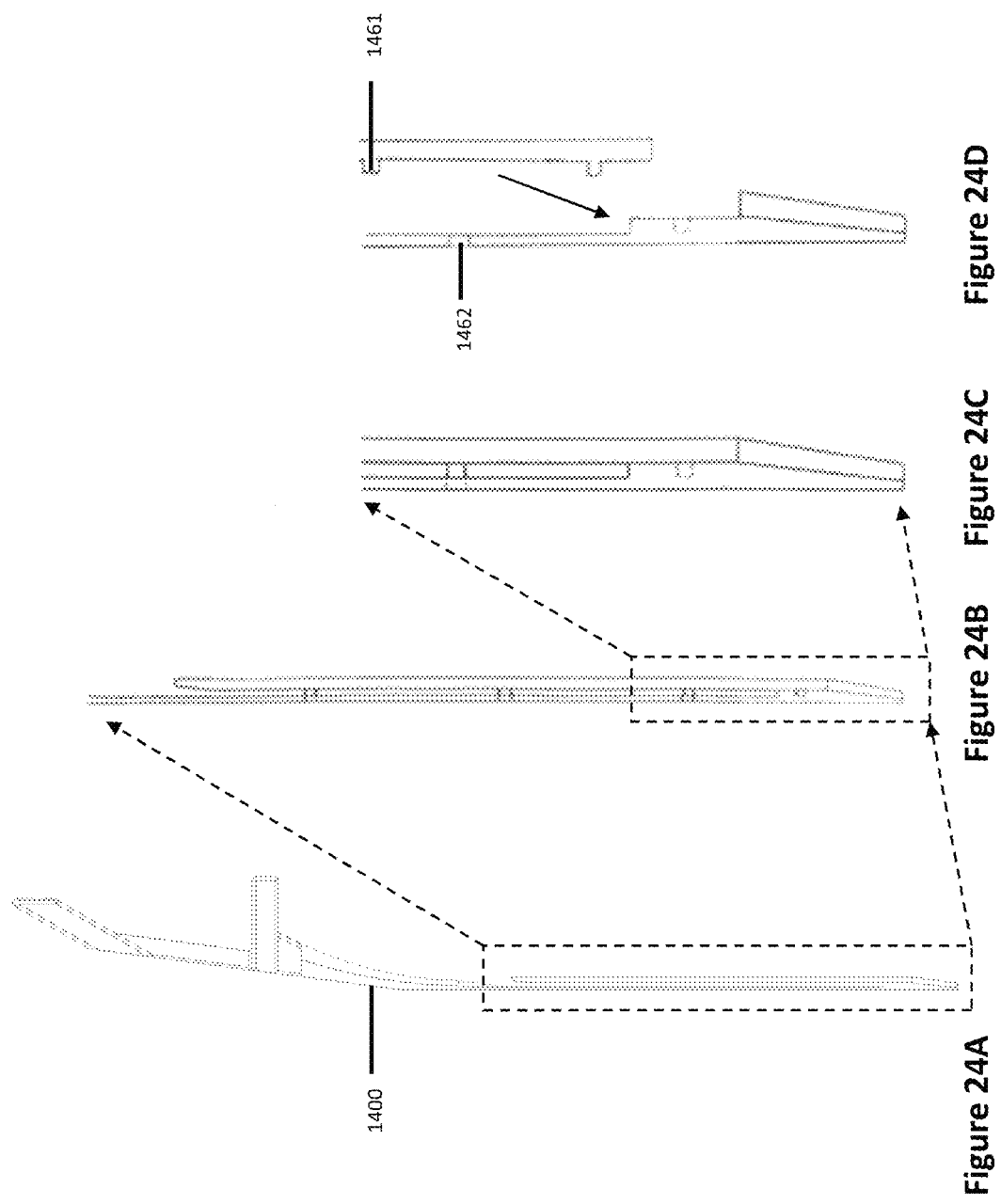

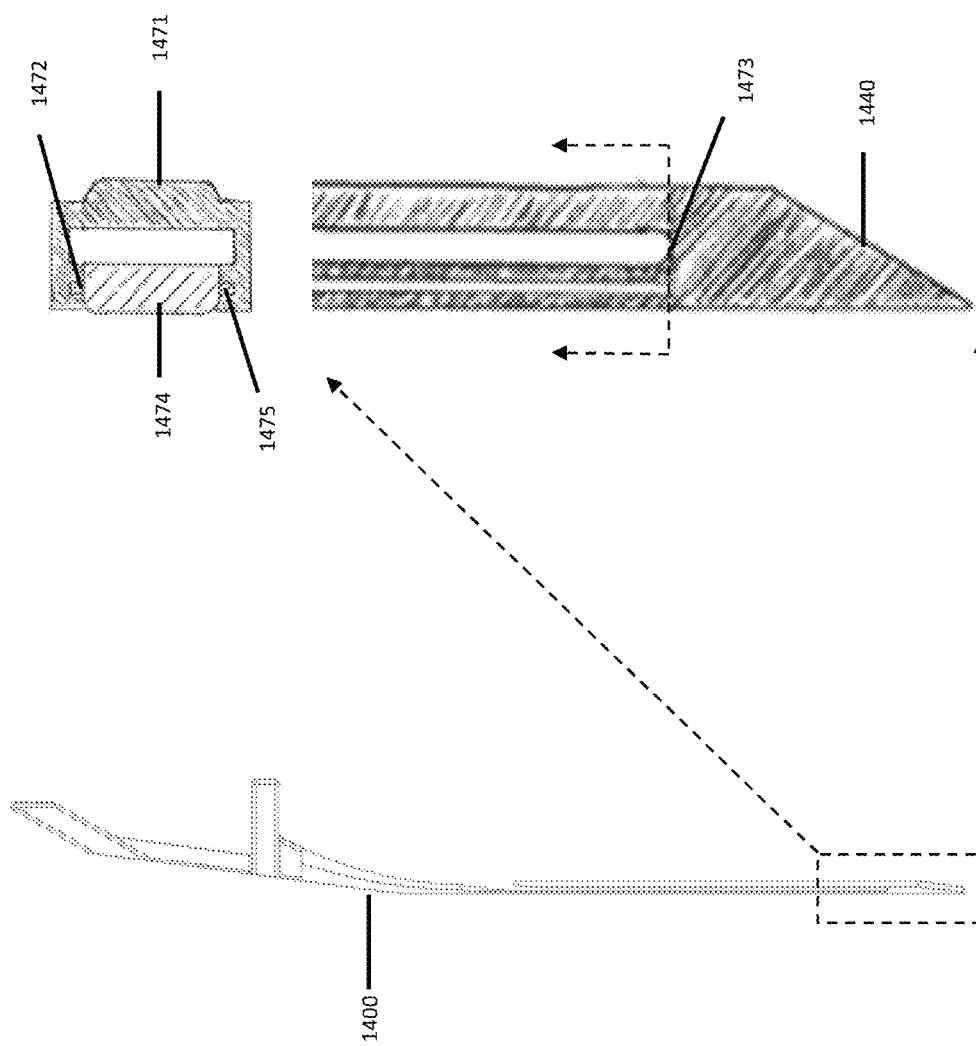

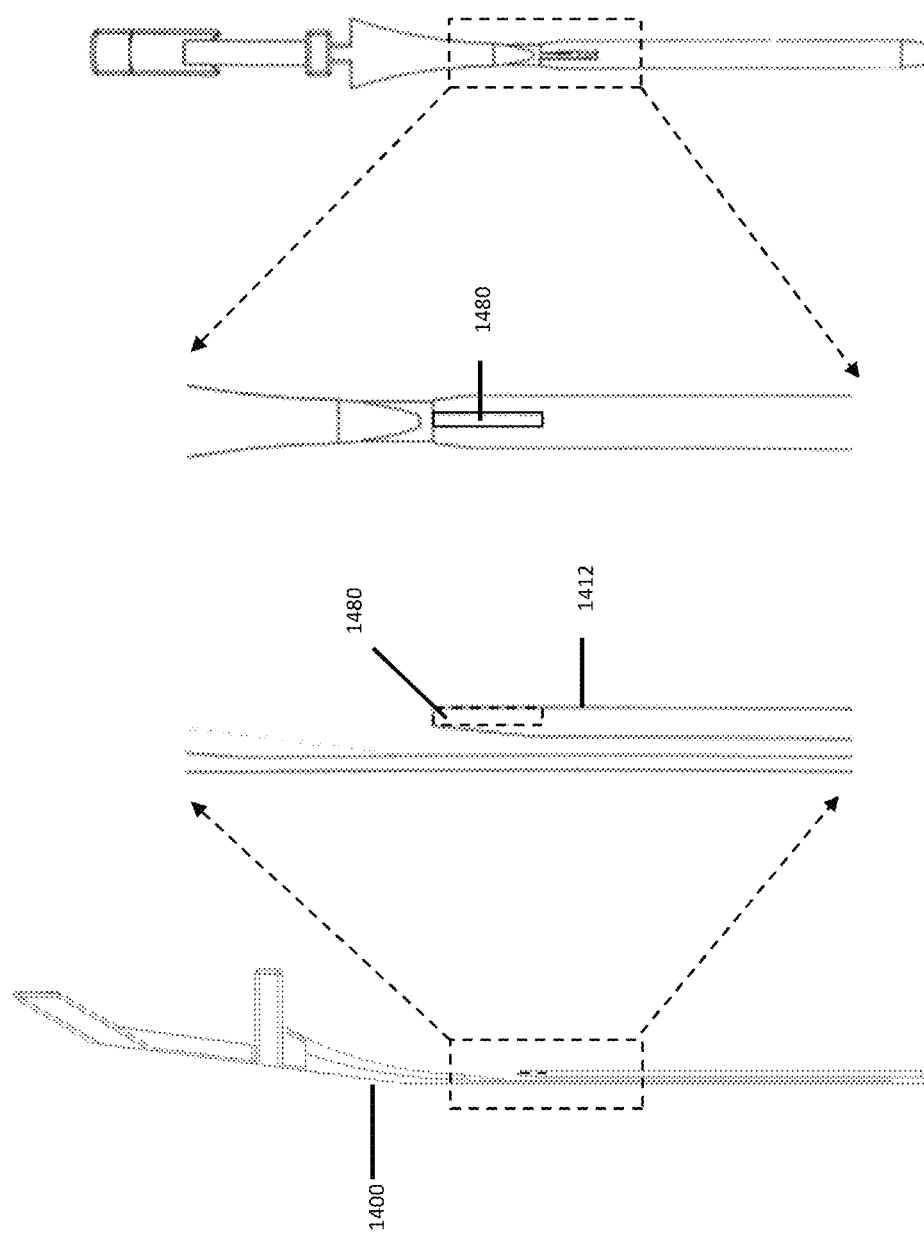

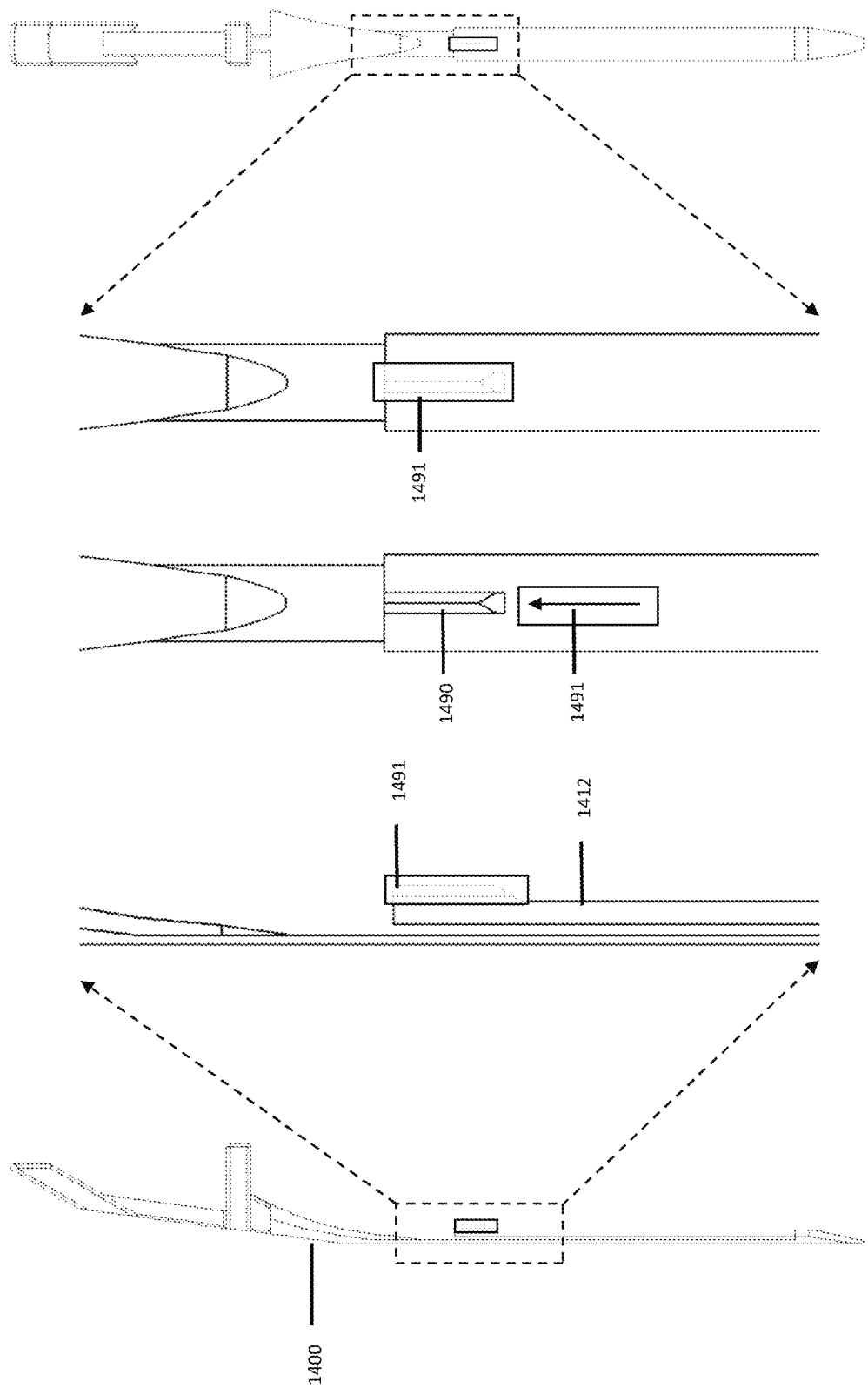

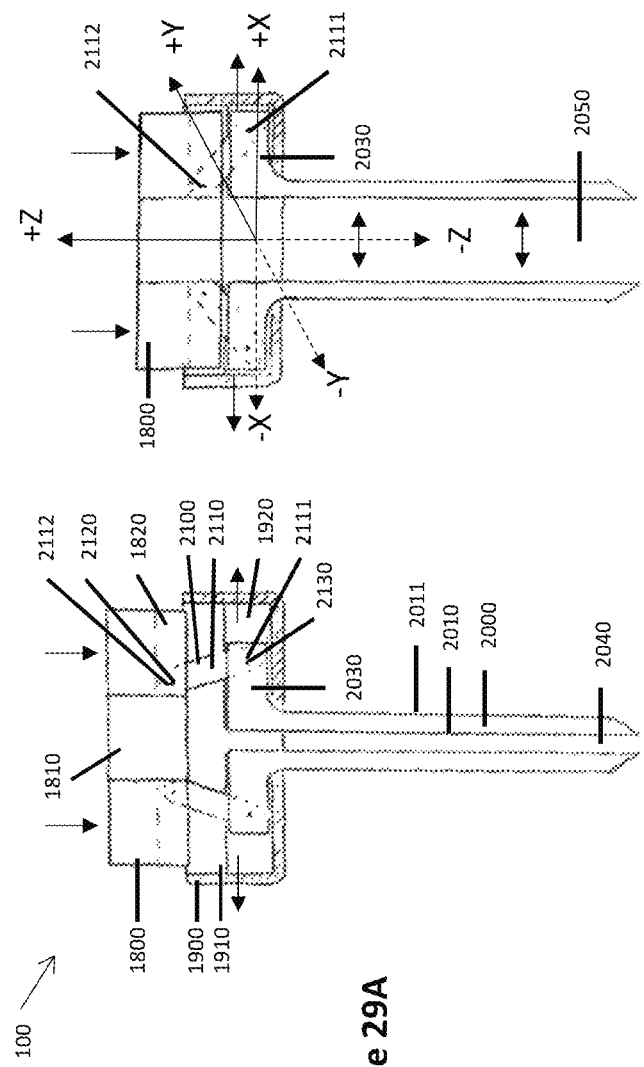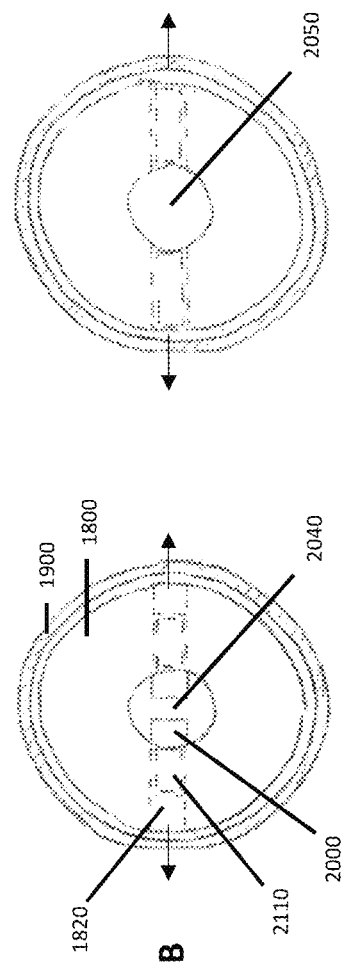

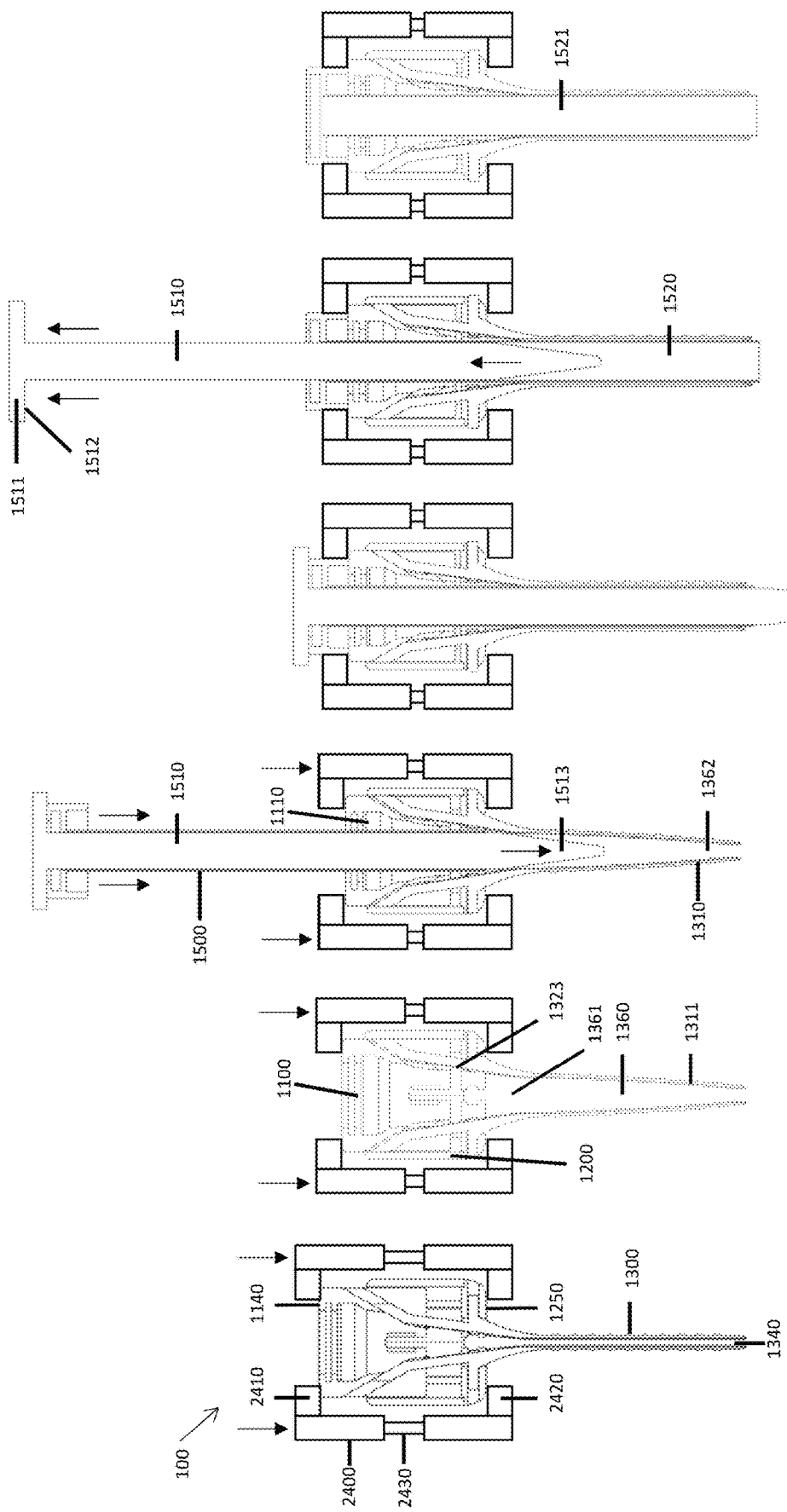

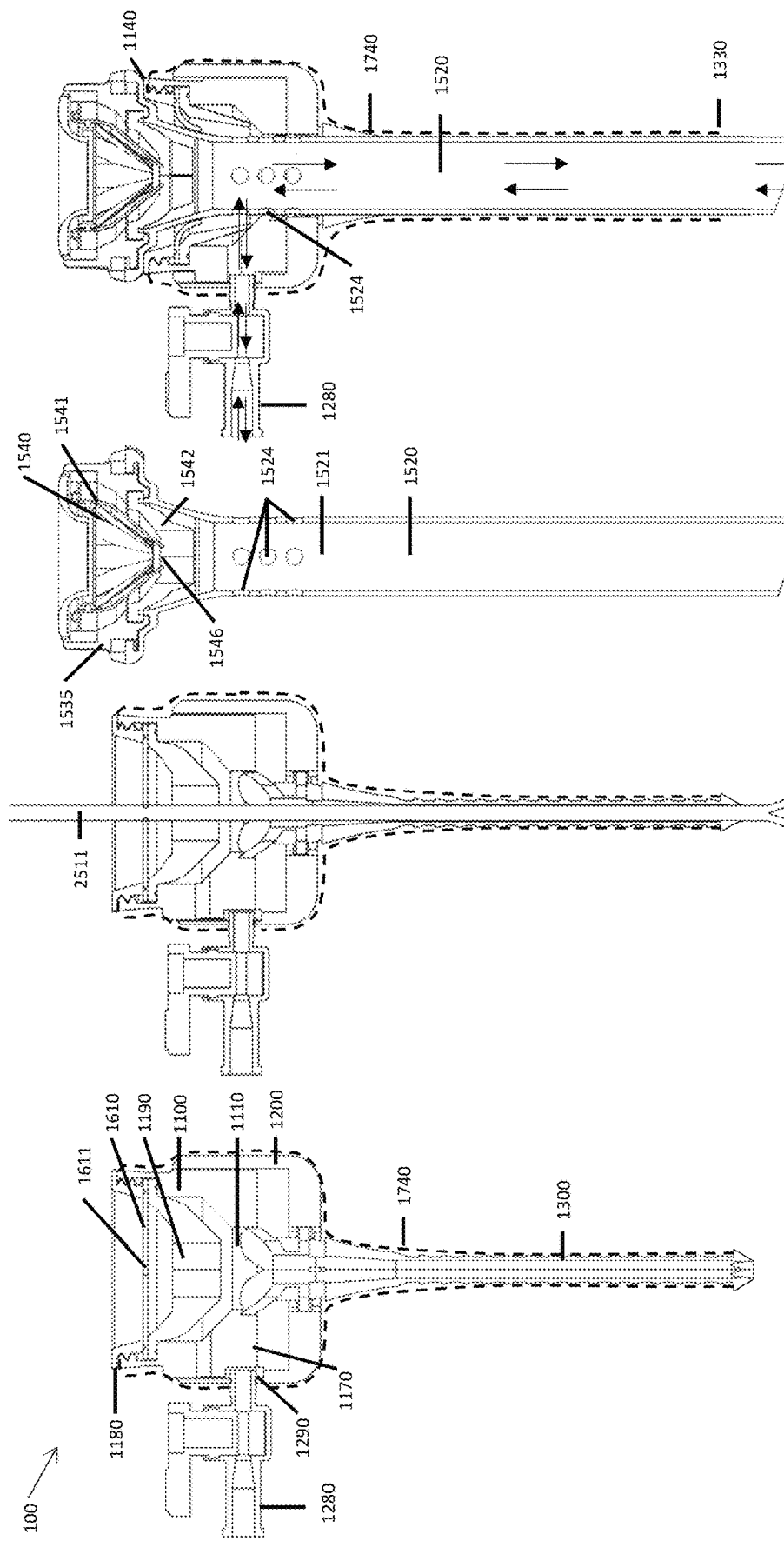

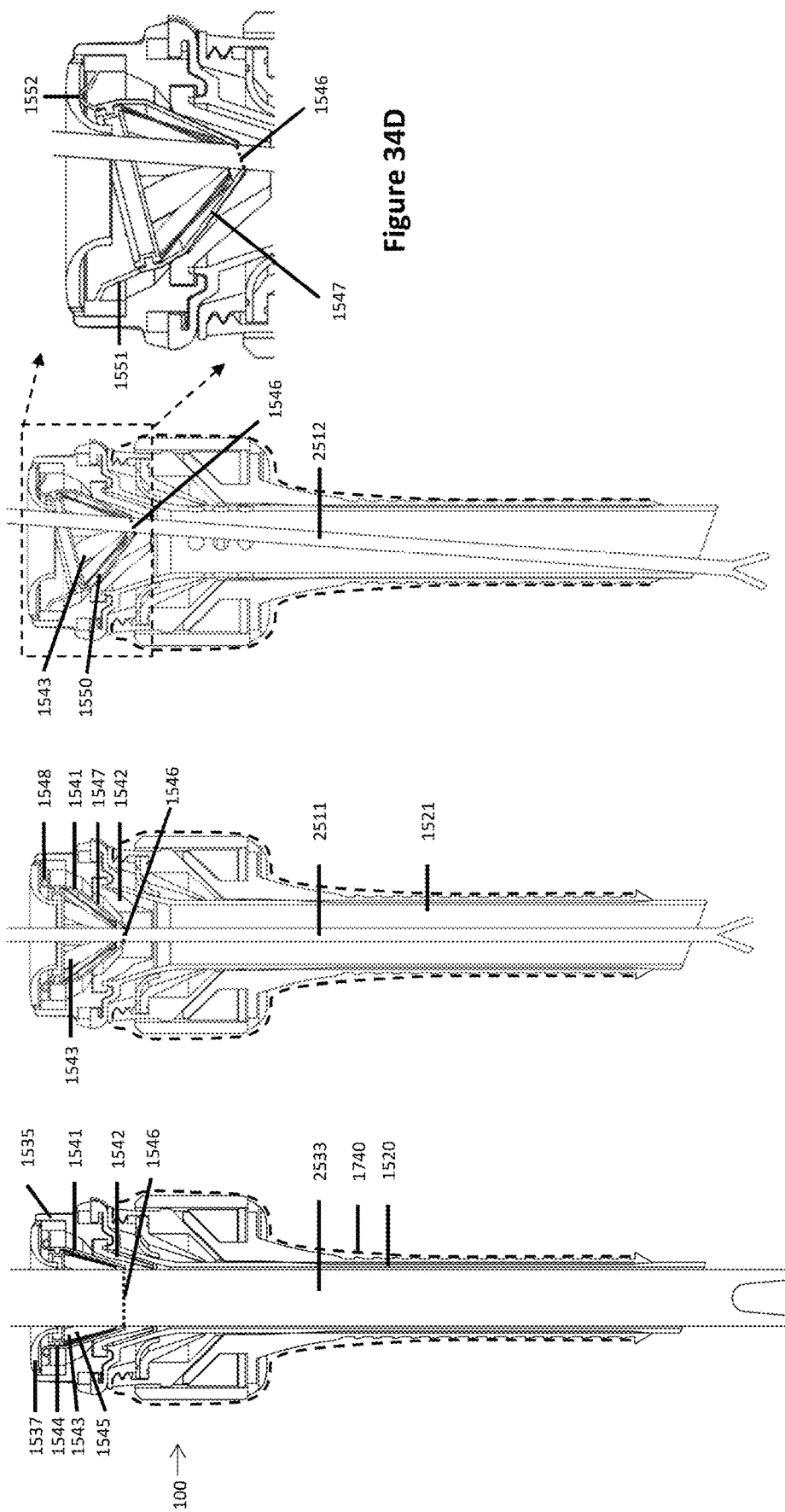

RADIALLY EXPANDABLE CANNULA DEVICES, AND SYSTEMS AND METHODS FOR USING THEM

RELATED APPLICATION DATA

This application is a continuation of co-pending International Application No. PCT/IB2021/000199, filed Mar. 12, 2021, which claims benefit of U.S. provisional application Ser. No. 62/989,520, filed Mar. 13, 2020, the entire disclosures of which are expressly incorporated by reference herein.

TECHNICAL FIELD

The technical field relates generally to methods and devices used in minimally invasive surgeries or key-hole surgeries. For example, the technical field relates to cannula devices and trocar devices for insertion in an incision.

BACKGROUND

In the majority of minimally invasive abdominal surgeries (laparoscopic surgeries), skin incisions are made on the surface of the abdominal wall, and several fixed-diameter ports (trocars) are inserted into the abdomen to facilitate instrument usage during the surgery. These ports are typically in the range of five to twelve millimeters (5-12 mm) in diameter. The fixed-diameter ports on the market have converged to very similar product offerings with little to no differentiation and come with a set of issues.

Generally, the force of trocar insertion into tissue is directly proportional to the diameter of the trocar. The larger the force of entry, the more dangerous and riskier it becomes to the patient, since the surgeon will have less control over its entry and the port can accidentally plunge into the patient and puncture an internal organ or major blood vessel. This forceful trocar entry remains the leading cause of complications in laparoscopic surgeries, contributing to approximately half of all complications that occur during laparoscopic surgeries.

In some scenarios, a need may arise to enlarge the diameter of a small port in order to use a larger instrument. These situations may be pre-planned or based on an emergency situation, such as sudden bleeding that requires usage of laparoscopic staplers, clip appliers or sutures, or difficult anatomy to navigate that requires repositioning of the endoscope or camera. In these situations, the small port would be removed, and a larger diameter port would be inserted through the same path to upsize.

Upsizing with fixed-diameter ports can prove to be an inefficient task for surgeons since larger ports may not be readily available in the operating theatre where a nurse may need to leave the room to obtain a larger device. Upsizing can also be dangerous for the patient as when the small trocar is removed, loss of abdominal pneumoperitoneum occurs and the surgical field of view is lost. Pneumoperitoneum must be re-established after inserting the larger trocar to re-establish the surgical field of view. Upsizing also creates an additional risk of injury to the patient since the abdominal tissue re-approximates after removing the small trocar, causing the original trocar path to be lost. This is especially challenging in obese patients, where the larger diameter port may be inserted through a different path all together, creating another wound in the patient and requiring an additional puncture that may lead to injury.

In other scenarios, the fixed-diameter ports may dislodge and slip out of the abdominal wall over time and use. This may also lead to a loss of pneumoperitoneum and may add an additional risk of re-entry injury.

With larger fixed-diameter ports, especially greater than ten millimeters (10 mm), the defect left in the tissue may be large and require manual suturing of the fascia or the use of a fascial closure (suturing) device to reduce the risk of developing post-operative incisional hernia. This consumes significant time at the end of surgery, where the patient must remain under general anaesthesia. For patients requiring fascial closure devices, this adds additional time and cost to the surgeries.

The differentiating features between the fixed-diameter ports are subtle and often aim to solve one problem while hindering another. For example, many fixed-diameter ports have threads around the cannula that improve fixation in the abdominal wall, however this causes higher insertion forces, and potentially larger defect size due to the threads. Other fixed-diameter ports have bladed tips which reduce insertion forces by cutting through tissue, however they could be more dangerous if they were to puncture an internal organ or major blood vessel with their blade. Other ports have blunt tips which increase insertion forces but are able to dilate tissue fibres instead of cutting them like the bladed trocars do, which may result in a smaller defect in the tissue afterwards.

One way to mitigate some of these problems is to use a dilating port. The first radially dilating port and currently the only one on the market is Innerdyne's (now Medtronic's) VersaStep port (U.S. Pat. No. 5,431,676 A, US 20060212062 A1, U.S. Pat. No. 7,896,897 B2). It includes a mesh sleeve with an outer polymeric coating, which is inserted into the abdomen with a Veress needle. The Veress needle is then removed, leaving a passage for a large member (dilator) to be inserted, expanding the mesh sleeve in the abdomen.

While the VersaStep port reduces initial insertion forces, it has been proven to perform poorly in other areas. Firstly, the dilator still requires large brute force to be inserted, as it must be inserted in a small path and break through the solid polymeric coating in order to expand the mesh sleeve. The FDA MAUDE database reports many incidences of pieces of the polymeric coating detaching from the mesh sleeve and not being able to be retrieved. In addition, both the polymeric coating and the mesh sleeve are made from smooth material and commonly slip out during surgeries. This requires re-entry which again adds injury risk. If the sleeve slips out of the body it cannot be easily re-entered since its smooth coating is detached. This requires the wasteful use of a new mesh sleeve unit. Surgeons can also accidentally penetrate the sides of the mesh sleeve and pierce abdominal tissue during entry of the dilators, because of the flexible nature of the mesh sleeve and lack of solid components that guide the entry of the dilators in a concentric fashion. Upsizing this system is also challenging because a small trocar must be removed from the mesh sleeve, while the surgeon must attempt to retain the sleeve in the body in order to keep the same path. The sleeve offers no protection against gas loss during the upsizing process either. Upsizing is also wasteful using this system because it requires opening a new unit of a larger diameter including a new mesh sleeve. In the event that the mesh sleeve fails to remain in the abdomen and slips out, a new sleeve must be utilized as well. Regardless of these limitations, this system remains an accepted approach for its less-invasive trocar entry, especially with pediatric procedures. However, the issues that arise prevent it from being a widely adopted option, thus there is still a need for a less invasive expandable port that performs well and addresses these gaps.

Problems also exist within a neurosurgical environment, where there exists a dichotomy between risk and benefit in brain tumour resection for example, where resection has been proven to increase survival rates, however surgeons are limited in their ability to intervene due to risks of neurological damage. Traditionally, open resection has been performed with flat retractors which apply high pressure on small surface areas which can damage brain tissue (by decreased perfusion and local ischemia), specifically white matter tracts, leading to poor outcomes. A limited number of tubular retractor access devices have been developed to combat these issues, where a fixed diameter (~13 mm) tubular retractor is entered into brain tissue. The circular/tubular profile of this device helps distributing pressure equally and radially onto the surrounding tissue, thereby reducing high pressure points and potential damage caused by the conventional flat retractors, however these retractors have not been widely adopted for deep-seated tumours as there are inherent safety risks associated with the large and fixed diameter entry which can still damage white matter tracts and thus important neurological function. As in laparoscopy, there exists a need in neurosurgery for a port that offers less invasive, and a single step radial expansion that reduces trauma to brain tissue.

Accordingly, devices, systems, and methods that facilitate accessing a subject's body, e.g., to introduce one or more instruments, would be useful.

SUMMARY

The present application is directed to devices, systems, and methods for accessing a subject's body, e.g., for accessing a laparoscopic or other surgical space, and more particularly to cannula and trocar devices for insertion in an incision to allow introduction of one or more instruments into the subject's body.

To combat one or more the issues described above, especially those pertaining to high applications of force/brute force, in one example, methods are provided for expanding a port by creating an internal conical taper (or guide) of elongate rigid members that facilitates less forceful and easily controllable entry of large diameter member into the smaller cannula; and the mechanism to create this conical taper leverages a novel mechanism which uses a vertical application of force on an internal housing to create such taper, all of which can be performed intuitively and efficiently in a surgical setting.

The vertical expansion mechanism is used in reverse to cause retraction and does not require the use of biasing elements such as springs to cause the elongate rigid members to return back to their initial position; this reduces the amount of force that is required to cause expansion in tissue.

The vertical application of force that creates an internal conical taper of elongate rigid members also allows for the larger member to be inserted in a continuous single step. The internal conical taper may be created in two ways: 1) manually or electromechanically by applying a vertical force downwards (distal) on a first housing in a second housing causing the proximal region of the elongate rigid members to increase in cross-sectional area and create an internal conical taper or guide, or 2) by inserting a large dilating member into a first housing where a resistive member is housed, where a large member applies a downwards (distal) force on the resistive member, actuating the expansion mechanism in the housing where the elongate rigid members create an internal conical taper (guide) at the proximal region of the cannula, and at the proximal region of the tissue. Thus, the interaction of the large member and resistive member facilitates a one-step motion of creating an internal conical taper while simultaneously inserting the large member to expand the port. Such mechanisms may also be actuated using electromechanical or robotic systems.

By creating an internal conical taper using a vertical application of force before inserting a large member, the insertion is less forceful, controllable and safer. It does not tug and shear the internal tissue as a twisting/torquing mechanism would, and instead expands radially such that the tissue is less impacted.

The rate of expansion/contraction may be controlled as the internal conical taper creates a gradual conical passage, preventing any sudden movements, and preventing the tissue from experiencing high pressure/force in a short period of time. A user can insert a large member at their speed of comfort. Given a fixed/known amount of force by a user or an electromechanical system in a given interval of time, the present designs may also be modified to control the size of the expansion, the degree and the size of the internal conical taper that is created and how fast it is created. This can be modified by changing the angles of the diagonal elongate rigid members, along with the overall length & diameter of the first housing, and diameter of the second housing. Additionally, and in other embodiments, the material selection of the resistive member (e.g., flat backup valve) and the sheath or cover (sealing elastic member) that surrounds the elongate rigid members can also be fine tuned to control the rate of expansion/retraction given a known amount of force to expand/retract.

The large member may also range in diameter, and there is no requirement to pre-determine the size before expansion. For example, a smaller member may be inserted first, upon which a user may realize they require a larger member, in which case they may remove the smaller member and insert a larger member seamlessly and without compromising the trocar functionality, loss of pneumoperitoneum, and place in the tissue.

In addition to the main expansion mechanism, additional embodiments may include one or more of:

an obturator with a distal tip that has complimentary geometry to the distal internal surface of the elongate rigid members, that creates a seamless internal and external interface with the elongate rigid members at the retracted state. This requires less force to penetrate the tissue and fully penetrate the fascial layers compared to conventional fixed diameter trocars and obturators. The tip shape can be blunt, sharp or have a Veress needle;

an embodiment where the distal region of the elongate rigid members come together to form a seamless and closed tip which allows the expandable cannula device to be used without an obturator;

a sealing elastic member around the device that creates a fluid seal preventing fluid transfer between the lumen of the cannula and the exterior environment, with and without instruments in the cannula, where the sealing elastic member can have different geometries and can be assembled onto the elongate rigid members, first and second housings in various ways;

an incision-making guide comprised of a slot or blade on the elongate rigid members;

an alternative expansion mechanism wherein the expansion of the elongate rigid members is actuated by a hinge system connecting the first housing to the elongate rigid members;

a mount that is fixated to the external surface of the second housing that can be attached to an arm of a robotic surgical system, with or without the ability of the mount to initiate expansion of the expandable cannula device using a mechanical mechanism;

an embodiment of the expandable cannula device with a stopcock, a sealing elastic member, a one-way valve and backup valve which can prevent gas leakage with and without instruments, and a fixed diameter cannula is shown with an array of holes, a backup valve and a one-way valve, which can also prevent gas leakage with and without instruments, wherein the valve systems and sealing elastic member of the expandable cannula device and fixed diameter cannula work together to prevent gas leakage from the entire device;

a fixed diameter cannula where its head contains a conical backup valve and a one-way valve that can be separated from the distal cylindrical body via a latch mechanism for the purpose of allowing the full diameter of the open passage for rapid desufflation of gas, which may be important during emergencies or if the CO2 pressure is too high which may cause embolisms for example, or for specimen retrieval;

small and large instruments inserted through the cylindrical passage of the fixed diameter cannula while retaining a gas-tight seal; and/or the expansion assembly with an obturator and a fixed diameter cannula without the insufflation holes that can be used as its own cannula device, and in similar fashion to conventional trocars.

In accordance with an exemplary embodiment, a cannula device is provided that includes a first housing defining a first throughbore aligned along a central axis; a second housing defining a second throughbore aligned with the first throughbore along the central axis, the second housing moveable in an axial direction along the central axis with respect to the first housing; a plurality of elongate members cooperatively defining a passage axially aligned with the first throughbore along the central axis between proximal ends and distal tips of the elongate members; and a plurality of guide elements on the proximal ends of the elongate members and the first and second housings configured to cooperate such that axial movement of the first housing with respect to the second housing along the central axis causes the proximal ends of the elongate members to move outwardly with respect to the central axis to move away from each other and increase a size of the passage, wherein the elongate members are configured such that, as the proximal ends move radially outwardly, if the distal tips are constrained, the elongate members define a tapered shape extending from the proximal ends towards the distal tips.

In accordance with another exemplary embodiment, a cannula device is provided that includes a first housing defining a first throughbore aligned along a central axis; a second housing defining a second throughbore aligned with the first throughbore along the central axis, the first housing moveable in an axial direction along the central axis at least partially into the second throughbore of the second housing; a plurality of elongate members cooperatively defining a passage axially aligned with the first throughbore along the central axis between proximal ends and distal tips of the elongate members; a plurality of guide elements on the proximal ends of the elongate members and the first and second housings configured to cooperate such that axial movement of the first housing with respect to the second housing along the central axis causes the proximal ends of the elongate members to move outwardly with respect to the central axis to move away from each other and increase a size of the passage; and a resistive member within the first housing adjacent an inlet communicating with the first throughbore, the resistive member configured to receive a secondary device therethrough when the secondary device is inserted into the inlet and first throughbore and couple axial movement of the first housing to axial movement of the secondary device.

In accordance with still another embodiment, a cannula device is provided for use with an obturator including an elongate shaft defining an outer diameter; and an obturator tip on a distal end of the shaft having a cross-section larger than the outer diameter, the cannula device including a first housing defining a first throughbore aligned along a central axis; a second housing defining a second throughbore aligned with the first throughbore along the central axis, the first housing moveable in an axial direction along the central axis with respect to the second housing; a plurality of elongate members cooperatively defining a passage axially aligned with the first throughbore along the central axis between proximal ends and distal tips of the elongate members; and a plurality of guide elements on the proximal ends of the elongate members and the first and second housings configured to cooperate such that axial movement of the first housing with respect to the second housing along the central axis causes the proximal ends of the elongate members to move outwardly with respect to the central axis to move away from each other and increase a size of the passage, wherein the distal tips of the elongate members include interior tapers from the passage to an outlet of the elongate members sized to receive a portion of the obturator tip when the shaft is positioned within the passage.

In accordance with yet another embodiment, a cannula device is provided that includes a first housing defining a first throughbore aligned along a central axis; a second housing defining a second throughbore aligned with the first throughbore along the central axis, the first housing moveable in an axial direction along the central axis with respect to the second housing; a plurality of elongate members cooperatively defining a passage axially aligned with the first throughbore along the central axis between proximal ends and distal tips of the elongate members; and a plurality of guide elements on the proximal ends of the elongate members and the first and second housings configured to cooperate such that axial movement of the first housing with respect to the second housing along the central axis causes the proximal ends of the elongate members to move outwardly with respect to the central axis to move away from each other to an expanded configuration and increase a size of the passage, wherein longitudinal side edges of the elongate members are disposed adjacent one another to enclose the passage when the first and second housings are in a first position before the elongate members move outwardly, and the side edges are spaced apart from one another when the first and second housings are in a second position where the elongate members are moved away from each other to increase a size of the passage, and wherein the distal tips of the elongate members taper inwardly to enclose the passage in the first position.

In accordance with still another embodiment, a cannula device is provided that includes a first housing defining a first throughbore aligned along a central axis; a second housing defining a second throughbore aligned with the first throughbore along the central axis, the first housing moveable in an axial direction along the central axis with respect to the second housing; a plurality of elongate members cooperatively defining a passage axially aligned with the first throughbore along the central axis between proximal ends and distal tips of the elongate members; a plurality of guide elements on the proximal ends of the elongate members and the first and second housings configured to cooperate such that axial movement of the first housing with respect to the second housing along the central axis causes the proximal ends of the elongate members to move outwardly with respect to the central axis to move away from each other and increase a size of the passage; and a membrane overlying the elongate members from the proximal ends at least partially towards the distal tips to provide a fluid-tight seal to prevent gas within the passage from escaping between the elongate members.

In accordance with yet another embodiment, a cannula device is provided that includes a first housing defining a first throughbore aligned along a central axis; a second housing defining a second throughbore aligned with the first throughbore along the central axis, the first housing moveable in an axial direction along the central axis with respect to the second housing; a plurality of elongate rigid members cooperatively defining a passage axially aligned with the first throughbore along the central axis between proximal ends and distal tips of the rigid members; and a plurality of linkages on the proximal ends of the rigid members and the first housing configured to cooperate such that axial movement of the first housing with respect to the second housing along the central axis causes the proximal ends of the rigid members to move outwardly with respect to the central axis to move away from each other and increase a size of the passage.

In accordance with still another embodiment, a cannula device is provided that includes a first housing defining a first throughbore aligned along a central axis; a second housing defining a second throughbore aligned with the first throughbore along the central axis, the first housing moveable in an axial direction along the central axis with respect to the second housing; a plurality of elongate members cooperatively defining a passage axially aligned with the first throughbore along the central axis between proximal ends and distal tips of the elongate members; and a plurality of guide elements on the proximal ends of the elongate members and the first and second housings configured to cooperate such that axial movement of the first housing in a first direction with respect to the second housing along the central axis causes the proximal ends of the elongate members to move outwardly with respect to the central axis to move away from each other and increase a size of the passage, and, after expanding the passage, axial movement of the first housing in a second direction opposite the first direction causes the proximal ends of the elongate members to move inwardly to decrease a size of the passage.

In accordance with another exemplary embodiment, a system is provided for introducing one or more instruments into a patient's body to perform a procedure that includes a cannula device including a. first and second housings defining a throughbore along a central axis, the first housing moveable in an axial direction along the central axis with respect to the second housing; b. a plurality of elongate members extending distally from the first and second housings, the elongate members cooperatively defining a passage axially aligned with the throughbore along the central axis between proximal ends and distal tips of the elongate members; and c. a plurality of guide elements on the proximal ends of the elongate members and the first and second housings configured to cooperate such that axial movement of the first housing with respect to the second housing along the central axis causes the proximal ends of the elongate members to move outwardly with respect to the central axis to move away from each other and increase a size of the passage, the distal tips of the elongate members include interior tapers from the passage to an outlet of the elongate members such that the outlet has a larger diameter than the passage; and an obturator including a. an elongate shaft configured to be inserted through the throughbore into the passage and defining an outer diameter; and b. an obturator tip on a distal end of the shaft having a cross-section larger than the outer diameter, the tapers of the distal tips sized to receive a portion of the obturator tip when the shaft is positioned within the passage.

In accordance with still another exemplary embodiment, a system is provided for introducing one or more instruments into a patient's body to perform a procedure that includes a cannula device including a. first and second housings defining a throughbore along a central axis, the first housing moveable in an axial direction along the central axis with respect to the second housing; b. a plurality of elongate members extending distally from the first and second housings, the elongate members cooperatively defining a passage axially aligned with the throughbore along the central axis between proximal ends and distal tips of the elongate members; and c. a plurality of guide elements on the proximal ends of the elongate members and the first and second housings configured to cooperate such that axial movement of the first housing with respect to the second housing along the central axis causes the proximal ends of the elongate members to move outwardly with respect to the central axis to move away from each other and increase a size of the passage, the distal tips of the elongate members include interior tapers from the passage to an outlet of the elongate members such that the outlet has a larger diameter than the passage; and a secondary device sized for insertion through the throughbore into the passage, the secondary device configured to engage the first housing to cause the first housing to move distally relative to the second housing to move the elongate members away from each other and increase the size of the passage.

In accordance with yet another embodiment, a system is provided for introducing one or more instruments into a patient's body to perform a procedure that includes a cannula device including a. first and second housings defining a throughbore along a central axis, the first housing moveable in an axial direction along the central axis with respect to the second housing; b. a plurality of elongate members extending distally from the first and second housings, the elongate members cooperatively defining a passage axially aligned with the throughbore along the central axis between proximal ends and distal tips of the elongate members; and c. a plurality of guide elements on the proximal ends of the elongate members and the first and second housings configured to cooperate such that axial movement of the first housing with respect to the second housing along the central axis causes the proximal ends of the elongate members to move outwardly with respect to the central axis to move away from each other and increase a size of the passage; an obturator removably received through the throughbore and passage with the rigid members in a reduced profile such that a distal tip of the obturator extends beyond the distal ends of the elongate members, the distal tip of the obturator sharpened to penetrate tissue to create an entry hole into the subject's body and facilitate insertion of the cannula device through the tissue; and a set of secondary members sized for insertion through the throughbore into the passage, each secondary member configured to engage the first housing to cause the first housing to move distally relative to the second housing to move the elongate members away from each other and increase the size of the passage.

In accordance with still another embodiment, a system is provided for introducing one or more instruments into a patient's body to perform a procedure that includes a cannula device including a. first and second housings defining a throughbore along a central axis, the first housing moveable in an axial direction along the central axis with respect to the second housing, one of the first and second housings comprising a side port communicating with the throughbore such that a source of pressurized gas connected to the side port can deliver gas through the one or more openings into the throughbore; b. a plurality of elongate members extending distally from the first and second housings, the elongate members cooperatively defining a passage axially aligned with the throughbore along the central axis between proximal ends and distal tips of the elongate members; and c. a plurality of guide elements on the proximal ends of the elongate members and the first and second housings configured to cooperate such that axial movement of the first housing with respect to the second housing along the central axis causes the proximal ends of the elongate members to move outwardly with respect to the central axis to move away from each other and increase a size of the passage; and an elongate tubular member comprising a proximal end, a distal end sized for insertion through the throughbore into the passage, and a lumen extending between the proximal and distal ends, the tubular member comprising one or more openings in a sidewall thereof communicating with the lumen such that pressurized gas introduced from the side port passes through the one or more openings into the lumen. In accordance with another exemplary embodiment, a method is provided for performing a medical procedure within a subject's body that includes connecting a cannula device to an arm of a robotic surgical system, the cannula device comprising first and second housings defining a throughbore along a central axis, the first housing moveable in an axial direction along the central axis with respect to the second housing, a plurality of elongate members extending distally from the first and second housings, the elongate members cooperatively defining a passage axially aligned with the throughbore along the central axis between proximal ends and distal tips of the elongate members; inserting distal tips of the elongate members through tissue into the subject's body using the arm; expanding the cannula device by moving the first housing relative to the second housing along the central axis, thereby causing proximal ends of the elongate members to move outwardly with respect to the central axis to move the elongate members away from each other and increase a size of the passage; and introducing one or more instruments through the expanded cannula device to perform the medical procedure within the subject's body.

The described mechanisms may further be appreciated in view of the Detailed Description of Example Embodiments, herein below.

Other aspects and features of the present invention will become apparent from consideration of the following description taken in conjunction with the accompanying drawings.

BRIEF DESCRIPTION OF THE DRAWINGS

The invention is best understood from the following detailed description when read in conjunction with the accompanying drawings. It is emphasized that, according to common practice, the various features and design elements of the drawings are not to-scale. On the contrary, the dimensions of the various features and design elements are arbitrarily expanded or reduced for clarity. Included in the drawings are the following figures:

FIGS. 1A-1D are isometric and cross-sectional side views of an example of an expandable cannula device in an initial (retracted) state (FIGS. 1A and 1C) and an expanded state (FIGS. 1B and 1D).

FIGS. 2A-2F are cross-sectional side views of an expandable cannula device, where the proximal region of the elongate rigid members is first expanded to create a larger cross-sectional lumen than the distal region, permitting a less forceful insertion of an expansion assembly, which itself expands the distal region of the lumen.

FIGS. 3A-3F are cross-sectional side views of the device of FIGS. 2A-2F but shown in reverse, depicting the removal of the expansion assembly followed by the retraction of the expanded cannula.

FIGS. 4A-4F are cross-sectional side views of another example of an expandable cannula device with a resistive member seated in the first housing, and also acting as a backup valve. The Figures illustrate the expansion assembly engaging with the resistive member, which in turn engages the expansion mechanism depicted in previous figures.

FIGS. 6A-6E are cross-sectional side views of the expandable cannula of FIGS. 4A-4F, where engaging the resistive member with the expansion assembly causes the proximal region of the elongate rigid members to expand and create a larger cross-sectional lumen than the distal region, permitting a less forceful insertion of an expansion assembly, which itself expands the distal region of the lumen.

FIGS. 8A-8E are cross-sectional side views of an alternative embodiment of an expandable cannula device similar to the device shown in FIGS. 6A-6E, wherein the resistive member includes a plurality of rigid strips which behave in a similar way to the resistive member shown in FIGS. 6A-7D when engaging with an expansion assembly.

FIGS. 10A-10E are cross-sectional side views of another embodiment of an expandable cannula device including tapers within distal tips that cooperate with an obturator such that once the obturator is inserted fully into the passage of the cannula device, the obturator tip cooperates with the recesses to create a seamless and smooth interface with the distal tips of the elongate rigid members, thus facilitating less forceful entry into tissue.

FIGS. 11A-11E are cross-sectional side views and full side views of an alternative method of inserting an obturator into a cannula device, similar to that shown in FIGS. 10A-10E, to create a seamless distal interface.

FIGS. 12A-12D are cross-sectional side views showing removal of the obturator from the expandable cannula device, in a reversed sequence of what is shown in FIGS. 10A-10E.

FIGS. 14A-14E are cross-sectional side views of an example of an 'obturator-less' cannula device including a plurality of elongate rigid members including distal tips that form a seamless interface to facilitate inserting a navigational member into the passage of the device prior to expansion, and where a fixed diameter cannula is shown inserted in the device depicting the expanded form.

FIGS. 15A-15B are cross-sectional side views of an example of an expandable cannula device including first and second elastic sealing members covering exterior surfaces of the cannula device in a retracted and expanded state.

FIGS. 15C-15D are cross-sectional side views of an alternative embodiment of assembling the first elastic sealing member at a proximal region of the first housing, using an O-ring approach to create a gas-tight seal.

FIGS. 16A-16B are cross-sectional side views of an alternative embodiment of an expandable cannula device including first and second elastic sealing members covering exterior surfaces of the cannula device in a retracted and expanded state, where the proximal section includes bellow-like features.

FIGS. 18A-18B, 19A-19B, and 20A-20B are cross-sectional side views and details of various embodiment of 'u-shaped' elongate rigid members wherein a distal end of a sealing elastic member is protected inside grooves of the 'u-shaped' features.

FIGS. 21A-21B are cross-sectional side view and detail, respectively, of an alternative embodiment of an elongate rigid member including a distal-most ridge is larger than proximal ridges spaced apart along a length of the rigid member, creating a proximal surface to which a distal end of an elastic sealing member is attached and protected from direct contact with tissue.

FIGS. 22A-22D, 23A-23D, 24A-24D, and 25A-25B are cross-sectional views of various alternative configurations for 'u-shaped' elongate rigid members.

FIGS. 26A-26D are side and front views of an exemplary embodiment of a 'u-shaped' elongate rigid member with an incision-making guide.

FIGS. 28A-28E are side and front views of an alternative embodiment of a 'u-shaped' elongate rigid member with a blade and a protective cover.

FIGS. 29A-29D are cross-sectional side and top views of another embodiment of an expandable cannula device, where elongate rigid members that are guided radially within a second housing and connected to a first housing via linkages or hinges that can initiate expansion and retraction of the cannula device via the movement of the first housing relative to the second housing.

FIGS. 31A-31F are cross-sectional side views of an alternative embodiment of an expandable cannula device that is attached to a robotic arm, wherein the robotic arm is configured to actuate movement of housings of the cannula device to expand and contract the expandable cannula device.

FIGS. 32A-32B are cross-sectional side views of an exemplary embodiment of expandable cannula device including a side port with a stopcock, a sealing elastic member, a one-way valve and a backup valve that collectively provide gas sealing protection during insufflation and desufflation of gas into an operable cavity of a subject into which the device is introduced, and when an instrument is inserted in the lumen of the expandable cannula device.

FIGS. 32C-32D are cross-sectional side views of an exemplary embodiment of a fixed diameter cannula including a one-way valve, a backup valve, and an array of holes that permit insufflation and desufflation of gas once the fixed diameter cannula is inserted into the lumen of the expandable cannula device.

FIGS. 34A-34D are cross-sectional side views of an exemplary embodiment of an expandable cannula device in its expanded state with a fixed diameter cannula, wherein instruments of different diameters are inserted and manipulated at different angles inside the lumen of the fixed diameter cannula, where the expandable cannula device and the fixed diameter cannula cooperatively prevent the loss of gas from their lumen.

DETAILED DESCRIPTION OF EXEMPLARY EMBODIMENTS

Figure 5E:
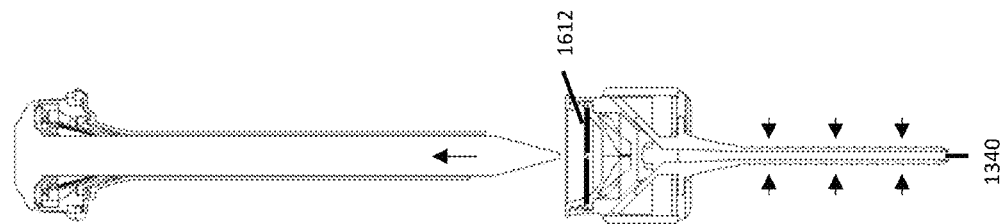
FIGS. 5A-5E are cross-sectional side views of the device of FIGS. 4A-4F but shown in reverse, depicting the removal of the expansion assembly followed by the automatic retraction of the expanded cannula as result of the engagement with the resistive member.

Before the exemplary embodiments are described, it is to be understood that the invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials are now described.

It must be noted that as used herein and in the appended claims, the singular forms "a," "an," and "the" include plural referents unless the context clearly dictates otherwise. Thus, for example, reference to "a compound" includes a plurality of such compounds and reference to "the polymer" includes reference to one or more polymers and equivalents thereof known to those skilled in the art, and so forth.

Throughout the detailed description, references to 'upwards' motion or locations usually refer to proximal motion or locations. Similarly, references to 'downwards' motion or location usually refers to distal motion or locations. Additionally, some references to the term 'vertical' may mean axial, and vice versa and can be discerned from the referenced figures.

Turning to FIGS. 1A-1D, an exemplary embodiment of an expandable cannula device 100 is shown, wherein a system of a cylindrical first housing 1100, a plurality of elongate rigid members 1300 and a second housing 1200 are operably connected such that specific axial motion causes the parts to remove relative to one another to expand the passage of the expandable cannula device 100 to be used as an access port in a surgical environment.

With particular reference to FIGS. 1A and 1B, an exemplary embodiment of an expandable cannula device 100 is shown comprising a cylindrical first housing 1100 defining a first throughbore 1110; a plurality of elongate rigid members 1300 cooperatively defining a passage/lumen 1340 axially aligned with the first throughbore 1110, the plurality of elongate rigid members 1300 connected to the first housing 1100; a cylindrical second housing 1200 defining a second throughbore 1210, the second housing 1200 moveable in an axial direction with respect to the first housing 1100, the second housing 1200 being operably connected to the elongate rigid members 1300 such that axial movement of the second housing 1200 with respect to the first housing 1100 causes the plurality of elongate rigid members 1300 to move away from each other and increase the cross-sectional area of the passage 1350, as shown in FIGS. 1B and 1D. The reverse axial movement of the second housing 1200 with respect to the first housing 1100 causes the plurality of elongate rigid members 1300 to move closer to each other and decrease the cross-sectional area of the passage 1340.

In this embodiment, the first housing 1100 and the second housing 1200 are axially aligned relative to each other, but in alternative embodiments may not be cylindrical in shape. For example, both or either one of the first housing 1100 or the second housing 1200 can be rectangular or triangular or polygonal in shape.

In some embodiments, the second housing 1200 surrounds the first housing 1100 and is guided axially by a plurality of tongues 1120 in the outer surface of the first housing 1100 and a plurality of complimentary grooves 1220 on the inner surface of the second housing 1200. The plurality of tongues 1120 and grooves 1220 allows for only uniaxial motion to occur between the first housing 1100 and second housing 1200. The first housing 1100 and second housing 1200 may be made of a strong plastic that may be injection molded.

In alternative embodiments, the plurality of tongues 1120 and grooves 1220 may be in the form of a singular tongue in the second housing 1200 and a singular complimentary groove in the first housing 1100 (or vice versa) wherein the complimentary shape comprises a lock and key mechanism, or is arbitrary, has a plurality of tongues in the first housing 1100 and a plurality of complimentary grooves in the second housing 1200, or an extruded flat surface in the second housing 1200 and a complimentary extruded cut surface in the first housing 1100 (or vice versa), or other guidance mechanisms and designs known in the art. Additional examples of guide elements that may be provided on the housings 1100, 1200 and/or elongate rigid members 1300 may be found in International Publication No. WO 2019/046940, the entire disclosure of which ix expressly incorporated by reference herein.

In alternative embodiments, the second housing 1200 may be manufactured in more than one piece which may be attached together to surround the first housing 1100.

With particular reference to FIGS. 1C and 1D, in some embodiments, the plurality of elongate rigid members 1300 include a distal internal surface 1311 and an outer surface 1312, a proximal diagonal rail 1321 and a distal horizontal rail 1322 perpendicular to the long axis of the elongate rigid member 1300, where the diagonal rail 1321 is complimentary to a diagonal groove 1130 in the first housing 1100, and the horizontal rail 1322 is complimentary to a horizontal groove 1230 in the second housing 1200. The distal internal surfaces 1311 of the plurality of elongate rigid members 1300 form the cross-sectional area of the cannula passage 1340.

The elongate rigid members 1300 must be made of a durable material with a high tensile strength such as stainless steel or plastic such that they cannot break under external radial and torsional forces. For example, the elongate rigid members 1300 may be substantially rigid in an axial direction between their proximal ends and the distal tips such that the elongate rigid members 1300 have sufficient column strength to facilitate introduction of the distal tips into a subject's body. Optionally, the elongate rigid members 1300 may be semi-rigid in a radial direction such that the elongate rigid members 1300 are deflectable perpendicular to the central axis locally, e.g., to allow the elongate members to define the tapered shape and/or to accommodate relatively larger obturator tips to be introduced between the elongate rigid members 1300, as described elsewhere herein.

In some embodiments, the external surface 1312 of the elongate rigid members 1300 may have surface modifications 1313 such as extrusions in the form of ridges or threads and/or other features spaced apart from one another along the lengths of the elongate rigid members 1300, which may improve the retention of the expandable cannula device 100 inside tissue. In alternative embodiments, there may be two or more elongate rigid members 1300, however, to simplify the illustration only two are shown in this embodiment.

A conventional cartesian coordinate system is shown for the purposes of describing the relative movements of the rightmost elongate rigid member 1300 shown in cross sectional FIGS. 1C-1D and the first housing 1100. For the purposes of illustration, the second housing 1200 is fixed in motion relative to the origin of the coordinate system, where the motion of the rightmost elongate rigid member 1300 and first housing 1100 is relative to the second housing 1200. However, it can be appreciated by a person versed in the art that, any combinations of relative motion are possible in this context (e.g., second housing moving with respect to a fixed first housing). In this embodiment, the first housing 1100 is concentric to the second housing 1200, where it moves vertically in the ±z direction, and where the rightmost elongate rigid member 1300 moves horizontally in the ±x direction.

This coordinate system will be referenced in other descriptions and figures in proceeding sections, referencing the rightmost elongate rigid member 1300 respectively in such figures and cross-sectional figures, and such that second housing 1200 remains fixed relative to the origin of the coordinate system. Since the movement of the other elongate rigid members 1300 happens in a similar but in different radial directions about the central axis of the expandable cannula device 100 and the rightmost elongate rigid member 1300, their motions will not be described in the same detail as someone who is versed in the art will be able to apply the same principles to understand their movements.

It is shown that the diagonal rail 1321 of the elongate rigid member 1300 is housed in the diagonal groove 1130 of the first housing 1100, and the horizontal rail 1322 of the elongate rigid member 1300 is housed in the horizontal groove 1230 of the second housing 1200. The material in between the diagonal rail 1321 and the horizontal rail 1322 of the elongate rigid member 1300 is rigid, such that they always maintain the geometry that is shown, and a fixed distance between each other. For example, the rightmost edge of the horizontal rail 1322 will always be vertically displaced from the rightmost edge of the diagonal rail 1321 by a fixed amount. It is also shown that the distal region 1310 of the elongate rigid member 1300 is also directly distal to the horizontal rail 1322 and the entirety of the elongate rigid member and all its features are made from solid material, such that the movement of one feature of this part along the z or x axes, means the movement of the entire elongate rigid member 1300 correspondingly.

When vertical force in the −z direction is applied on the first housing 1100 while it is in the second housing 1200, it causes the first housing 1100 to move downwards (distally) in the −z direction, causing it to be displaced downwards (distally) from its initial position. Since the diagonal rail 1321 is housed in the first housing 1100 and at the same time it must maintain a fixed distance away from the horizontal rail 1322, the vertical displacement in the −z direction of the first housing 1100, causes the diagonal rail 1321 to slide diagonally along the diagonal groove 1130 of the first housing 1100, and in an outwards direction. Simultaneously, and since there is a fixed distance away from the diagonal rail 1321 to the horizontal rail 1322 of the elongate rigid member 1300, this diagonal outwards motion causes the horizontal rail 1322 to slide horizontally outwards in the horizontal groove 1230 the +x direction. This in turn causes the entirety of the elongate rigid member 1300 to move outwards relative to its initial position, thus increasing the cross-sectional area of the passage created by the distal internal surfaces 1311 of the elongate rigid members 1300, expanding the passage 1350 of the expandable cannula device 100. The combination of these effects also creates a cam-follower mechanism or a double cam-follower mechanism.

FIG. 1D illustrates that the second housing 1200 remains fixed at an origin, while the first housing 1100 is displaced in the −z direction relative to the second housing 1200 until its furthest distal position, and the right elongate rigid member 1300 is displaced in the +x direction relative to the second housing 1200 to its rightmost position.

It can be appreciated by someone versed in the art that effects described herein occur simultaneously in the other elongate members 1300 that are shown in these figures, however, it will be a repetitive exercise to describe each in this coordinate system or a different coordinate system. For simple example, the left most elongate rigid member 1300 would be moving in the −x direction using the described coordinate system above.

Once the device is expanded, applying vertical force on the first housing 1100 in the +z direction causes the exact opposite set of motions to occur and therefore retract the elongate rigid members 1300 inwards and closer to each other and thus decreasing the cross-sectional area of the passage created by the distal internal surfaces 1311 of the elongate rigid members 1300 and retracting the expanded cannula 100.

In alternative embodiments, the size and shape of the diagonal rail 1321, diagonal groove 1130, horizontal rail 1322 and horizontal groove 1230 may differ, so long that their geometries are complimentary to allow smooth motion. The angle of the diagonal rail 1321 of the plurality of elongate rigid members 1300 and the angle of the diagonal groove 1130 in the first housing 1100 may also be increased or decreased to change the rate of vertical motion of the first housing 1100 in the second housing 1200, and thus the rate of expansion/retraction of the plurality of elongate rigid members 1300. Changing the rate of expansion/retraction may improve the surgical workflow, especially in situations where there is an emergency requiring a larger instrument to be inserted in the cannula device. It also allows for quicker & easier removal of the expandable cannula device after the surgery.

In this embodiment, the amount of downwards (distal) or upwards (proximal) vertical force applied in a given interval of time on the first housing 1100 can control the amount of expansion or retraction by controlling the cross-sectional area of the passage created by the distal internal surfaces 1311 of the elongate rigid members 1300, thereby expanding or retracting the passage 1350 of the expandable cannula device 100.

Additionally, the expansion and retraction described herein is occurring in a smooth, continuous, and analog-like manner that is not finite or stepwise (i.e., from inner diameter A to inner diameter B), which may be appreciated by someone versed in the art.

In alternative embodiments, the height, and inner and outer cross-sectional areas of the first housing 1100 and second housing 1200 may be increased or decreased to accommodate for a change in angle of the plurality of diagonal grooves 1130 in the first housing 1100 or a change in inner and outer cross-sectional area of the passage required. In alternate embodiments, the height and/or outer cross-sectional area of the first housing 1100 and second housing 1200 may remain the same and may accommodate for a change in angle of the plurality of diagonal grooves 1130 in the first housing 1100.

Turning to FIGS. 2A-2F, an exemplary method is shown for using the expandable cannula device 100 (shown in FIGS. 1A-1D), wherein vertical movement of the first housing 1100 relative to the second housing 1200 causes the proximal region 1320 of the elongate rigid members 1300 to move away from each other creating a larger proximal cross-sectional lumen 1361, such that an expansion assembly 1500 can be inserted to expand the expandable cannula device 100 for use in a surgical environment.

With particular reference to FIGS. 2A-2B, vertical movement of the first housing 1100 relative to the second housing 1200 causes the proximal region 1320 of the elongate rigid members 1300 to move away from each other creating a larger proximal cross-sectional lumen 1361, while the distal region 1310 of the elongate rigid members 1300 remain closer together with a smaller distal cross-sectional lumen 1362, creating a gradually tapered lumen 1360 (or a gradually tapered conical lumen 1360) throughout the passage 1360, wherein the gradually tapered lumen 1360 comprises a larger proximal cross-sectional lumen 1361, and a smaller distal cross-sectional lumen 1362. The gradually tapered lumen 1360 effect may occur if the elongate rigid members 1300 are under pressure from surrounding tissue, or external members (such as the sealing elastic member 1740 which is described in the proceeding sections). This may likely occur, especially if the elongate rigid members are made from rigid but flexible plastics or metals that can bend or deflect like a cantilever when subjected to external pressure. Nonetheless, this mechanism creates an interior passage within the elongate rigid members 1300 of the cannula device 100 that has a tapered conical shape 1360 which allows for a smoother entry of a large expansion assembly 1500 into the expandable cannula device 100, with less force by avoiding the direct contact with the proximal portions of the elongate rigid members 1300. The reduction of the friction of the expansion assembly 1500 with the elongate rigid member 1300 during its entry, reduces the large and uncontrollable force by the user that otherwise is needed to overcome the resistance due to the friction. In other devices, which are described in the existing art, this excessive force may cause serious harm or injury to the patient or may break the device and/or perforate the tissue of the patient accidentally due to this excessive force.

In this embodiment, external forces are applied onto the external surface 1312 of the elongate rigid members 1300. This may occur when the expandable cannula device 100 is be inserted in resilient tissue, wherein the tissue would apply force on the external surface 1312 of the distal region 1310 of the elongate rigid members 1300, causing the distal passage cross-sectional area 1362 to remain smaller than the proximal passage cross-sectional area 1361.

As previously described and with reference to the coordinate system in FIG. 1C and the rightmost elongate rigid member 1300 shown in this cross sectional figure, vertical force in the −z direction applied on the first housing 1100 in the second housing 1200 causes the first housing to move downwards (distally) in the −z direction, where the vertical force in the −z direction causes the rightmost elongate rigid member 1300 to move outwards to the right in the +x direction, where the diagonal rail 1321 of the elongate rigid member 1300 moves outwards along the diagonal groove 1130 in the first housing 1100, and where the horizontal rail 1322 moves outwards along the horizontal groove 1230 in the second housing 1200. The plurality of elongate rigid members 1300 follow, where the proximal region of the internal surface 1323 of the elongate rigid members 1300 creates a larger passage cross-sectional area 1361 than the distal internal surface 1311 of the elongate rigid members 1300, shown by a gradual taper of decreasing cross-sectional area (internal conical taper) 1360 throughout the passage.

In an alternative embodiment, the expandable cannula device 100 may have an elastic cover (such as the sealing elastic member 1740 which is described in proceeding sections) surrounding the elongate rigid members 1300 and second housing 1200, wherein the elastic cover may apply force on the external surface of the distal region of the elongate rigid members 1300, causing the distal passage cross-sectional area 1362 to remain smaller than the proximal passage cross-sectional area 1361. In an alternative embodiment, the expandable cannula device 100 may have both an elastic cover and be inserted in tissue.

With particular reference to FIG. 2C, in this exemplary embodiment, an expansion assembly 1500 including an obturator 1510 with an obturator head, handle, or hub 1511 and a distal tip 1513, and a fixed diameter cannula 1520 with a head, handle, or hub 1535 wherein the obturator 1510 can be inserted and removed from the fixed diameter cannula 1520, and wherein the entire expansion assembly 1500 can be inserted into the expandable cannula device 100. The purpose of inserting the fixed diameter cannula 1520 into the passage of the expanded cannula device 100, is to create a fully enclosed lumen inside the expanded region that was created by the elongate rigid members 1300. This fully enclosed lumen of the fixed diameter cannula 1520 allows for safe passage of instruments into the patient without the possibility of such instrument penetrating the tissue of the patient from the space in between the expanded elongate rigid members 1300. In this embodiment, an expansion assembly 1500 is inserted downwards (distally) through the throughbore 1110 of the first housing 1100 and the passage 1340 created by the distal internal surfaces 1311 of the elongate rigid members 1300. The distal tip 1513 of the obturator 1510 in the expansion assembly 1500 initiates contact with the distal internal surface 1311 of the elongate rigid members 1300 at the distal region of the conical taper 1362 and causes the distal region 1310 of the elongate rigid members 1300 to expand such that the distal internal surfaces 1311 of the elongate rigid members 1300 surround the expansion assembly 1500. It can be appreciated by someone versed in the art, that since the contact area between the expansion assembly 1500 and the distal internal surface 1311 of the elongate rigid members 1300 is minimized due to the internal taper 1360, lesser force is required to expand the distal region 1310 of the elongate rigid members 1300 than if the internal taper 1360 was not created.

In alternative embodiments, the cross-sectional area of the expansion assembly 1500 may be larger or smaller than depicted and range from 2.5 mm (or less) to over 15 mm in diameter to accommodate different instruments comprising different sizes. The fixed diameter cannula 1520 may have an angled cut at its distal end, which would be flush with the obturator 1510, to reduce resistance of the fixed diameter cannula 1520 while being inserted in the expandable cannula 100.

In an alternative embodiment, the elongate rigid members 1300 may be made of a flexible plastic allows them to remain tapered only in the proximal region and non tapered in the distal region 1310, where the expansion assembly 1500 will cause the elongate rigid members 1300 to expand only when the distal tip 1513 of the expansion assembly 1500 passes through each axial cross-sectional area of the elongate rigid members 1300.

In alternative embodiments, the obturator 1510 and fixed diameter cannula 1520 may be made of a variety of different materials that have a high tensile strength and will not break under high pressure, such as an injection molded plastic, or a metal.

With particular reference to FIG. 2D, in this exemplary embodiment, the expansion assembly 1500 is inserted completely, as dictated by the distal surface of the head 1522 coming into contact with the proximal surface 1140 of the first housing 1100, causing the elongate rigid members 1300 to straighten and no longer be tapered.

In other embodiments, this expanded cannula device 100, can be used to be entered into the patient as a conventional trocar.

In alternative embodiments, the distal tip 1513 of the obturator 1510 may have different shapes and/or configurations, e.g., a sharp or bladed tip, or a blunt tip of a different taper angle, and/or the obturator 1510 may be hollow. In other embodiments, the hollow obturator 1510 may have an optically clear tip 1513, and can be used as conventional optical obturator, for use along with an endoscope.

With particular reference to FIG. 2E-2F, in this exemplary embodiment, the obturator 1510 is removed from the fixed diameter cannula 1520 to allow for instruments to be inserted through the hollow passage 1521 in the fixed diameter cannula 1520. The obturator 1510 is removed by applying a vertical force upwards (proximally) on the distal surface 1512 of the obturator head 1511 such that the fixed diameter cannula 1520 remains in place in the expandable cannula by the elongate rigid members 1300.

In alternative embodiments, a valve system may be provided that includes one or more seals and/or valves, e.g., a one-way valve 1190 and/or a resistive member 1610 (described further elsewhere herein), located in the proximal region of the throughbore 1110 in the first housing 1100 to prevent gas loss through the first housing 1100 during a procedure.

Turning to FIGS. 3A-3F, operation of the previously described expandable cannula device 100 (in FIG. 2) is shown in reverse, wherein the same mechanism of expanding the elongate rigid members 1300 may be used for retracting/contracting/compressing the elongate rigid members 1300 back to their smallest cross-sectional area.

With particular reference to FIGS. 3A-3C, in this exemplary embodiment, the obturator 1510 is inserted back through the fixed diameter cannula 1520 which is located in the expandable cannula device 100 surrounded by the expanded elongate rigid members 1300.

With particular reference to FIG. 3D-3E, the obturator 1510 and fixed diameter cannula 1520 are removed simultaneously by applying an upwards (proximal) force on the distal surface of the fixed diameter cannula head 1522, causing the elongate rigid members 1300 to move together again starting at the distal region 1310 and create a gradually tapered lumen 1360 (or gradually tapered conical lumen 1360) following the distal tip 1513 of the obturator 1510 as the expansion assembly 1500 is removed.

The distal surface 1150 of the first housing 1100 remains close to the internal proximal surface 1260 of the second housing 1200 and the horizontal rails 1322 of the elongate rigid members 1300 remain horizontally outwards (the right elongate rigid member 1300 in the +x direction) in the horizontal grooves 1230 in the second housing 1200, where the proximal region 1361 of the distal internal surface 1311 of the elongate rigid members 1300 maintains a larger passage cross-sectional area than the distal region 1362 of the elongate rigid members 1300 which has retracted, shown by a gradual conical taper of decreasing cross-sectional area 1360 throughout the passage.

With particular reference to FIG. 3F, and with particular reference to the coordinate system in FIG. 1C and the rightmost elongate rigid member 1300 shown in this cross section figure, the elongate rigid members 1300 are retracted to create the smallest internal passage cross-sectional area 1340, vertical force in the +z direction is applied on the first housing 1100 relative to the second housing 1200, which causes the first housing to move upwards (proximally) in the +z direction, and causes the rightmost elongate rigid member 1300 to move inwards to the left in the −x direction, where the diagonal rail 1321 of the elongate rigid member 1300 moves inwards along the diagonal groove 1130 in the first housing 1100, and where the horizontal rail 1322 moves inwards along the horizontal groove 1230 in the second housing 1200. This decreases the cross-sectional area of the passage created by the distal internal surfaces 1311 of the plurality of elongate rigid members 1300 and retracts the passage. The expandable cannula device 100 can be removed from tissue at this small cross-sectional area 1340 to reduce damage In an alternative embodiment (not shown), the fixed diameter cannula 1520 may be removed without the obturator 1510 having to be inserted first.

In an alternative embodiment, the expandable cannula device 100 is not retracted before removal from tissue.

In an alternative embodiment, the expandable cannula device 100 may have an elastic cover (such as the sealing elastic member 1740 which is described in proceeding section) surrounding the elongate rigid members 1300 and second housing 1200, wherein the elastic cover in tension applies an inwards force on the external surface of the elongate rigid members 1300, causing the elongate rigid members 1300 to retract as described above.

Turning to FIGS. 4A-4F, another exemplary embodiment of an expandable cannula device 100 (generally similar to that shown in FIGS. 1A-1D) is shown, wherein the first housing 1100 includes a resistive member 1610, and wherein an expansion assembly 1500 can initiate the vertical movement of the first housing 1100 with respect to the second housing 1200, thus causing the elongate rigid members 1300 to move away from each other or move towards each other. This mechanism may be used to reduce the force of inserting an expansion assembly into the first housing 1100 and the distal part of the passage to improve safety, while also streamlining the expansion in a one-step process, which may be very useful in emergency situations that require a quick reaction and response.

With particular reference to FIG. 4A, in this exemplary embodiment, the first housing 1100 comprises a resistive member 1610 housed concentrically in a revolved cavity 1160 in the proximal region of the throughbore 1110, above the highest point of the diagonal rails 1321 of the elongate rigid members 1300. The resistive member 1610 includes a backup valve, which is common in the laparoscopic trocars on the market. It serves to reduce or prevent gas loss from the proximal end of the passage through the throughbore of the first housing 1100, when an instrument is inserted and manipulated through the unexpanded device that is shown in FIG. 4A. The resistive member 1610 (backup valve) is made from an elastic member with a concentric hole 1611 and is capable of stretching to fit expansion assembly 1500 inside and retracting back to its original hole cross-sectional area after the expansion assembly 1500 is removed, wherein the concentric hole 1611 comprises a cross-sectional area that is smaller than the cross-sectional area of members, and instruments that would be inserted through it.

In an exemplary embodiment, the elastic member 1610 may be made of a thin polymer such as polyisoprene or silicone which can be made from sheet polymer where the hole 1611 can be punched. In an alternative embodiment, the resistive member 1610 may also be in the form of a flexible but not stretchable member, valve, spring or bracket. In an alternative embodiment, there may be more than one resistive member 1610. In an alternative embodiment, changing the geometry and material of the resistive member 1610 can change the rate and ease of expansion and retraction.

In an alternative embodiment, the cavity 1160 in which the resistive member 1610 is housed may also be in the form of a rectangular cut and can be located anywhere in the first housing 1100 above the diagonal grooves 1130.

With particular reference to FIG. 4B, in this exemplary embodiment, the expansion assembly 1500 engages with the resistive member 1610 to effect vertical movement of the first housing 1100 with respect to the second housing 1200, and therefore causing the elongate rigid members to move away from each other.

In this embodiment, an expansion assembly 1500 is guided towards the throughbore 1110 in the first housing 1100, where the distal tip 1513 of the obturator 1510 applies a downwards (distal) force on the resistive member 1610, where the hole 1611 in the resistive member 1610 begins to expand to accommodate the increasing cross-sectional area of the distal tip 1513 of the obturator 1510 and the material of the resistive member 1610 begins to stretch distally to create a partially expanded tapered passage 1613. Simultaneously, because the resistive member 1610 is housed in the cavity 1160 in the proximal region of the first housing 1100, the downwards (distal) application of force on the resistive member 1610 in the −z direction causes downward vertical movement of the first housing 1100 relative to the second housing 1200. This causes the rightmost elongate rigid member 1300 to move outwards to the right in the +x direction, where the diagonal rail 1321 of the elongate rigid member 1300 moves outwards along the diagonal groove 1130 in the first housing 1100, and where the horizontal rail 1322 moves outwards along the horizontal groove 1230 in the second housing 1200. The same outwards motion occurs for the other elongate rigid members 1300, where they are moving away from each other, thus increasing the cross-sectional area of the passage created by the distal internal surfaces 1311 of the elongate rigid members 1300, expanding the passage 1350 of the expandable cannula device 100.

With particular reference to FIGS. 4C-4D, as the expansion assembly 1500 is inserted further to the point of its largest possible cross-sectional area 1514, the hole 1611 in the resistive member 1610 stretches to a cross-sectional area equal to the outer cross-sectional area of the expansion assembly 1500, and the material is stretched to a distal position 1614, at which point the horizontal rails 1322 and diagonal rails 1321 of the elongate rigid members 1300 are displaced/expanded and the cross-sectional area of the passage created by the distal internal surfaces 1311 of the elongate rigid members 1300 is expanded such that the passage they create is sufficiently large in cross section to allow for the entry of the expansion assembly 1500. This creates an open passage 1350 for the expansion assembly 1500 to be inserted until the distal surface of the fixed diameter cannula head 1522 comes in contact with the proximal surface 1140 of the first housing 1100.

In an alternative embodiment, the same effect described above can be generated with the fixed diameter cannula 1520 alone and without an obturator 1510.

With particular reference to FIGS. 4E-4F, in this exemplary embodiment, the obturator 1510 is separated from the fixed diameter cannula 1520 to allow for instruments to be inserted through the hollow passage 1521 in the fixed diameter cannula 1520. The obturator 1510 is removed by applying a vertical force upwards (proximally) on the distal surface 1512 of the obturator head 1511 such that the fixed diameter cannula 1520 remains in place by the elongate rigid members 1300.

Turning to FIGS. 5A-5E, the previously described expandable cannula device 100 (from FIGS. 4A-4F) is shown being manipulated in reverse, wherein the same mechanism of expanding the elongate rigid members 1300 using a resistive member 1610 may be used for retracting/compressing the elongate rigid members 1300 back to their smallest cross-sectional area 1340.

Figure 5D:
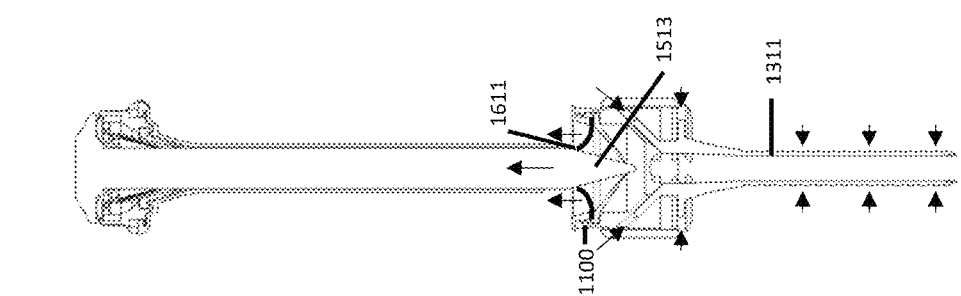
Figure 5C:
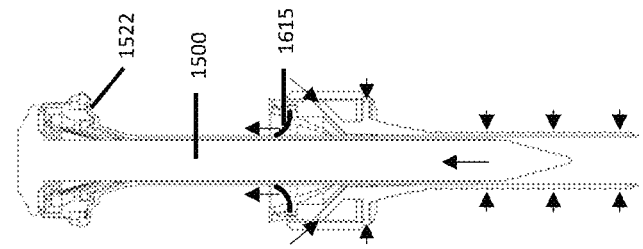
Figure 5B:
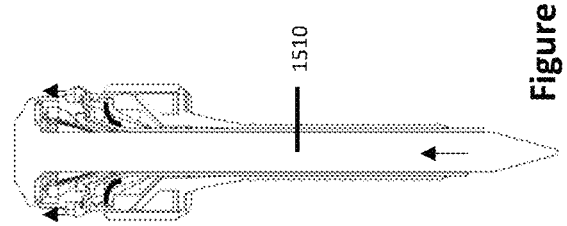
Figure 5A:
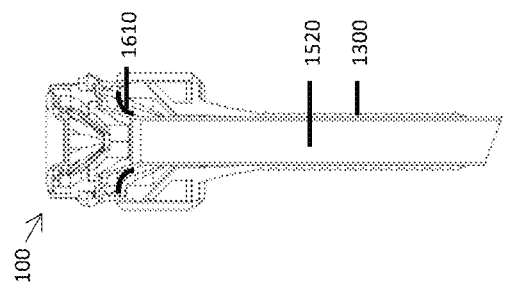

With particular reference to FIGS. 5A-5B, in this exemplary embodiment, the obturator 1510 is inserted back through the fixed diameter cannula 1520 which is located in the expandable cannula device 100 surrounded by the elongate rigid members 1300.

With particular reference to FIG. 5C, the obturator 1510 and fixed diameter cannula 1520 begin to be removed simultaneously by applying an upwards (proximal) force on the distal surface of the fixed diameter cannula head 1522, causing the resistive member 1610 to follow the expansion assembly 1500 and stretch proximally to create an opposite tapered passage 1615.

With particular reference to FIG. 5D, as the distal tip 1513 of the obturator 1510 moves upwards (proximally) in the +z direction through the hole 1611 in the resistive member 1610 and is no longer in contact with the distal internal surface 1311 of the elongate rigid members 1300, the hole 1611 cross-sectional area of the resistive member 1610 shrinks to accommodate the tapered obturator tip 1513 which is being removed, at which point the first housing 1100 moves axially (vertically) upwards (proximally) in the +z direction due to the upwards (proximally) force created by the expansion assembly 1500 and resistive member 1610 following the direction of the expansion assembly 1500, where the elongate rigid members 1300 move together again, and the cross-sectional area of the passage created by the distal internal surfaces 1311 of the elongate rigid members 1300 decreases.

With particular reference to FIG. 5E, when the expansion assembly 1500 is completely removed, the resistive member 1610 retracts back to its original hole cross-sectional area and is no longer stretched distally or proximally 1612, and the elongate rigid members 1300 retract back to their smallest cross-sectional area 1340.

In another embodiment, the same effect described above can be generated by removing the fixed diameter cannula 1520 alone and without an obturator 1510, in order to retract the expandable cannula device 100.

Turning to FIGS. 6A-6E, the previously described expandable cannula device 100 (of FIGS. 4A-4F) is shown, wherein a resistive member 1610 in the first housing 1100 and an expansion assembly 1500 can initiate the vertical movement of the first housing 1100 with respect to the second housing 1200, causing the internal surfaces 1323 of the proximal region of the elongate rigid members 1300 to move away from each other creating a larger proximal cross-sectional area 1361, while the distal region of the elongate rigid members 1300 remain closer together with a smaller distal cross-sectional area 1362, creating a gradual conical taper of decreasing cross-sectional area 1360 throughout the passage to initiate a smooth expansion.

With particular reference to FIGS. 6A-6C, as previously described and with reference to the coordinate system in FIG. 1C and the rightmost elongate rigid member 1300 shown in the cross section figures, an expansion assembly 1500 is guided towards the throughbore 1110 in the first housing 1100, where the distal tip 1513 of the obturator 1510 applies a downwards (distal) force on the resistive member 1610, where the hole 1611 in the resistive member 1610 expands to accommodate the cross-sectional area of the distal tip 1513 of the obturator 1510 and the material of the resistive member 1610 stretches distally to create a fully expanded tapered passage 1614. Simultaneously, because the resistive member 1610 is housed in the cavity 1160 in the proximal region of the first housing 1100, the application of downwards (distal) force on the resistive member 1610 in the −z direction causes downward vertical movement of the first housing 1100 relative to the second housing 1200. This causes the rightmost elongate rigid member 1300 to move outwards to the right in the +x direction, where the diagonal rail 1321 of the elongate rigid member 1300 moves outwards along the diagonal groove 1130 in the first housing 1100, and where the horizontal rail 1322 moves outwards along the horizontal groove 1230 in the second housing 1200. The plurality of elongate rigid members 1300 follow, where the proximal region of the internal surface 1323 of the elongate rigid members 1300 creates a larger passage cross-sectional area 1361 than the distal internal surface 1311 of the elongate rigid members 1300, shown by a gradual taper of decreasing cross-sectional area 1360 throughout the passage.

In an alternative embodiment, the expandable cannula device 100 may be inserted in tissue, wherein the tissue may apply force on the external surface 1312 of the distal region 1310 of the elongate rigid members 1300, causing the distal passage cross-sectional area 1362 to remain smaller than the proximal passage cross-sectional area 1361.

In an alternative embodiment, the expandable cannula device 100 may have an elastic cover surrounding the elongate rigid members 1300 and second housing 1200, wherein the elastic cover may apply force on the external surface of the distal region of the elongate rigid members 1300, causing the passage cross-sectional area to remain smaller than the proximal passage cross-sectional area.

In an alternative embodiment, the expandable cannula device 100 may have both an elastic cover and be inserted in tissue.

As the expansion assembly 1500 is inserted further to the point of its largest possible cross-sectional area 1514, the hole 1611 in the resistive member 1610 reaches its largest cross-sectional area (equal to the outer cross-sectional area of the expansion assembly 1500), and the material is stretched to a distal position 1614, at which point the horizontal rails 1322 and diagonal rails 1321 of the elongate rigid members 1300 displace from their contracted state, and the cross-sectional area of the passage created by the distal internal surfaces 1311 of the elongate rigid members 1300 is expanded. This creates an open passage 1350 for the expansion assembly 1500 to be inserted until the distal surface of the fixed diameter cannula head 1522 comes in contact with the proximal surface 1140 of the first housing 1100.

In an alternative embodiment, the same effect described above can be generated with the fixed diameter cannula 1520 alone and without an obturator 1510.

With particular reference to FIGS. 6D-6E, in this exemplary embodiment, the obturator 1510 is separated from the fixed diameter cannula 1520 to allow for instruments to be inserted through the hollow passage 1521 in the fixed diameter cannula 1520. The obturator 1510 is removed by applying a vertical force upwards (proximal) on the distal surface 1512 of the obturator head 1511 such that the fixed diameter cannula 1520 remains in place by the elongate rigid members 1300.

Turning to FIGS. 7A-7D the previously described expandable cannula device 100 (of FIGS. 6A-6E) is shown being manipulated in reverse, wherein the same mechanism of expanding the elongate rigid members 1300 using a resistive member 1610 may be used for retracting/compressing the elongate rigid members 1300 back to their smallest cross-sectional area.

Figure 7A:
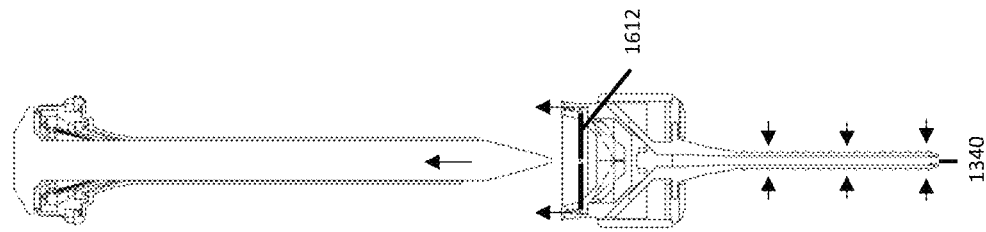
FIGS. 7A-7D are cross-sectional side views of the device shown in FIGS. 6A-6E but shown in reverse, depicting the removal of the expansion assembly followed by the automatic retraction of the expanded cannula as result of the engagement with the resistive member.
Figure 7B:
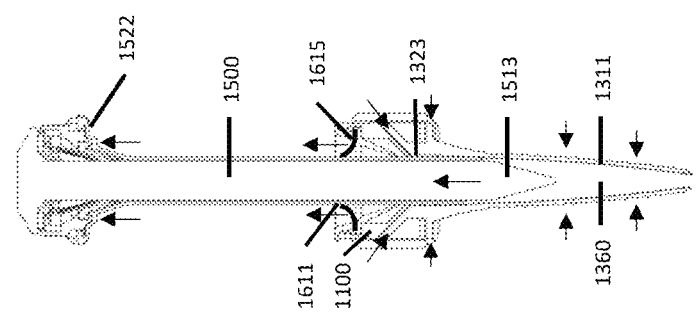

With particular reference to FIGS. 7A-7B, in this exemplary embodiment, the obturator 1510 is inserted back through the fixed diameter cannula 1520 which is located in the expandable cannula device 100 surrounded by the elongate rigid members 1300.

Figure 7C:
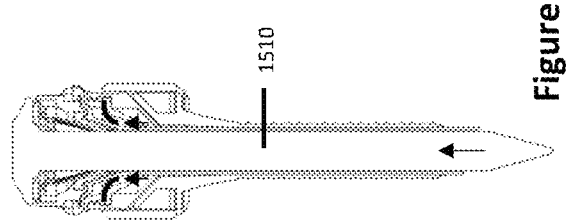

With particular reference to FIG. 7C, the obturator 1510 and fixed diameter cannula 1520 begin to be removed simultaneously by applying an upwards (proximal) force on the distal surface of the fixed diameter cannula head 1522, causing the resistive member 1610 to follow the expansion assembly 1500 and stretch proximally to create an opposite taper 1615.

As the distal tip 1513 of the obturator 1510 moves upwards (proximally) in the +z direction through the hole 1611 in the resistive member 1610 and is no longer in contact with the distal internal surface 1311 of the elongate rigid members 1300, the hole 1611 cross-sectional area of the resistive member 1610 shrinks to accommodate the decreasing taper of the obturator distal tip 1513 which is being removed, at which point the first housing 1100 moves vertically upwards (proximally) in the +z direction due to the upwards (proximal) force created by the expansion assembly 1500 and resistive member 1610 following the direction of the expansion assembly 1500. The proximal region of the internal surface 1323 of the elongate rigid members 1300 maintains a larger passage cross-sectional area than the distal region of the elongate rigid members 1300 which has retracted, shown by a gradual taper of decreasing cross-sectional area 1360 throughout the passage.

Figure 7D:
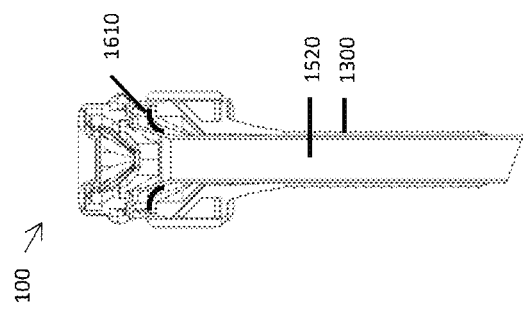

With particular reference to FIG. 7D, when the expansion assembly 1500 is completely removed, the resistive member 1610 retracts back to its original hole cross-sectional area and is no longer stretched distally or proximally 1612, and the elongate rigid members 1300 retract back to their smallest cross-sectional area 1340.

In another embodiment, the same effect described above can be generated by removing the fixed diameter cannula 1520 alone and without an obturator 1510, in order to retract the expandable cannula device 100.

In other embodiments, the functionality of the resistive member 1610 described in FIGS. 4A-7D can be achieved via the one-way valve 1190, e.g., as described further elsewhere herein, or by the combinations of the resistive member 1610 and the one-way valve 1190.

Turning to FIGS. 8A-8D, an alternative exemplary embodiment of an expandable cannula device 100 (generally similar to that shown FIGS. 6A-6E) is shown, except that the resistive member 1600 includes at least one or a plurality of rigid strips 1620, e.g., that behave similar to flexible metal strips that are commonly found in battery cases as the (negative leads contact points) or car-power adapter heads.

With particular reference to FIG. 8A, in this embodiment, the rigid strips 1620 are bent in a horizontal u-shape where the distal end 1621 is pinned in the cavity 1160 in the proximal region of the throughbore 1110 in the first housing 1100, and the proximal end 1622 is free such that under horizontal compression the rigid strip 1620 can deform and the proximal end 1622 can move radially outwards towards the wall of the cavity 1160 in the first housing 1100 to expand the passage 1623 created by the rigid strips 1620, and upon release of compression the rigid strip 1620 can return back to its original shape and create a small passage 1623 created by the rigid strips 1620.

In this embodiment, the plurality of rigid strips 1620 are initially positioned such that the internal surfaces of the rigid strips 1620 form a small passage 1623 into the throughbore 1110 of the first housing 1100.

The rigid strips 1620 can be made of a rigid metal that is not ductile such that there is no plastic deformation but is still flexible.

In an alternative embodiment, the passage created by the internal surfaces 1623 of the rigid strips 1620 may be any polygonal shape depending on the number of rigid strips 1620.

With particular reference to FIGS. 8B-8C, as previously described and with reference to the coordinate system in FIG. 1C, the rightmost elongate rigid member 1300 shown in the cross section figures and with reference particularly to the rightmost rigid strip 1620, an expansion assembly 1500 is guided towards the throughbore 1110 in the first housing 1100, where the distal tip 1513 of the obturator 1510 applies a downwards (distal) force in the −z direction on the rigid strips 1620, which pushes the right rigid strip 1620 in the +x direction, deforming it horizontally and forcing the free end 1622 to move radially outwards towards the wall of the cavity in the first housing 1100. The other rigid strips 1620 behave in a similar way respectively, thus fully expanding the passage 1623 created by the rigid strips 1620. to accommodate the gradually increasing cross-sectional area of the distal obturator tip 1513. Simultaneously, because the rigid strips 1620 are housed in the cavity 1160 in the proximal region of the first housing 1100, the application of force on the rigid strips 1620 in the −z direction causes downward vertical movement of the first housing 1100 relative to the second housing 1200, which causes the rightmost elongate rigid member 1300 to move outwards to the right in the +x direction, where the diagonal rail 1321 of the elongate rigid member 1300 moves outwards along the diagonal groove 1130 in the first housing 1100, and where the horizontal rail 1322 moves outwards along the horizontal groove 1230 in the second housing 1200. The plurality of elongate rigid members 1300 follow, where the proximal region of the internal surface 1323 of the elongate rigid members 1300 creates a larger passage cross-sectional area 1361 than the distal internal surface 1311 of the elongate rigid members 1300, shown by a gradual taper of decreasing cross-sectional area 1360 throughout the passage.

As the expansion assembly 1500 is inserted further to the point of its largest possible cross-sectional area 1514, the rigid strips 1620 are deformed to their maximum outwards position, therefore creating an inner passage 1623 equal to the outer cross-sectional area of the expansion assembly 1500, at which point the horizontal rails 1322 and diagonal rails 1321 of the elongate rigid members 1300 displace and the cross-sectional area of the passage created by the distal internal surfaces 1311 of the elongate rigid members 1300 is expanded. This creates an open passage 1350 for the expansion assembly 1500 to be inserted until the distal surface of the fixed diameter cannula head 1522 comes in contact with the proximal surface 1140 of the first housing 1100.

With particular reference to FIG. 8D-8E, in this embodiment, the obturator 1510 is separated from the fixed diameter cannula 1520 to allow for instruments to be inserted through the hollow passage 1521 in the fixed diameter cannula 1520. The obturator 1510 is removed by applying a vertical force upwards (proximally) on the distal surface 1512 of the obturator head 1511 such that the fixed diameter cannula 1520 remains in place in the expandable cannula by the elongate rigid members 1300.

Turning to FIGS. 9A-9D, the previously described expandable cannula device 100 (of FIGS. 8A-8E) is shown being manipulated in reverse, wherein the same mechanism of expanding the elongate rigid members 1300 using a plurality of rigid strips 1620 may be used for retracting/compressing the elongate rigid members 1300 back to their smallest cross-sectional area.

Figure 9D:
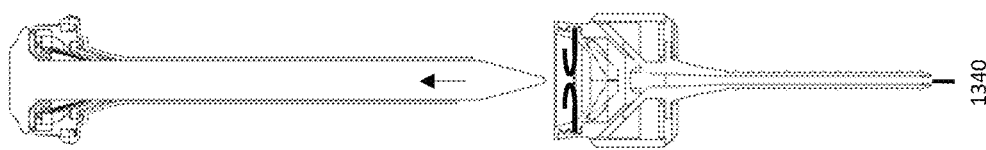
FIGS. 9A-9D are cross-sectional side views of the device of FIGS. 8A-8E but shown in reverse, depicting the removal of the expansion assembly followed by the retraction of the expanded cannula.
Figure 9C:
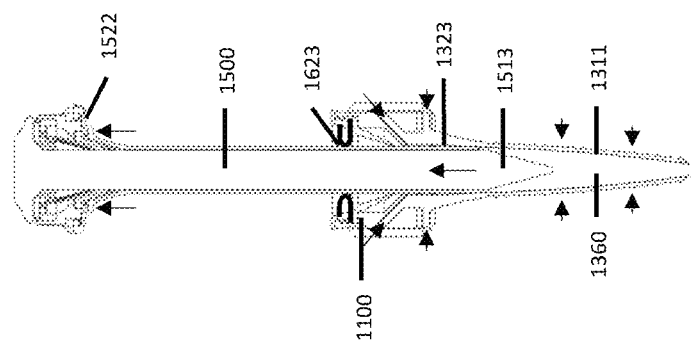
Figure 9B:
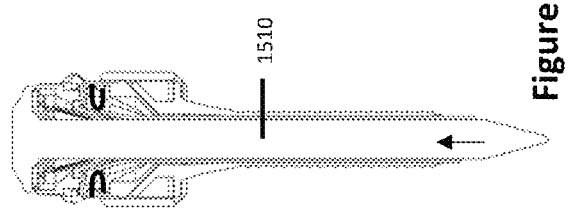
Figure 9A:
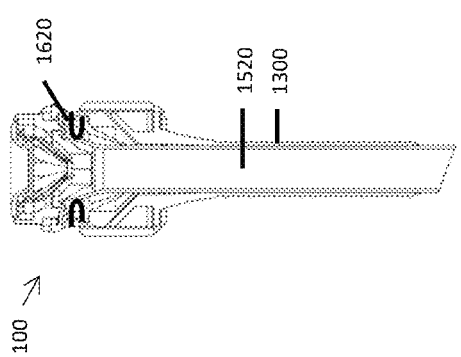

With particular reference to FIGS. 9A-9B, in this exemplary embodiment, the obturator 1510 is inserted back through the fixed diameter cannula 1520 which is located in the expandable cannula device 100 surrounded by the elongate rigid members 1300.

With particular reference to FIG. 9C, the obturator 1510 and fixed diameter cannula 1520 begin to be removed simultaneously by applying an upwards (proximal) force on the distal surface of the fixed diameter cannula head 1522, while the rigid strips 1620 remain and apply a horizontal force on the expansion assembly 1500.

As the distal tip 1513 of the obturator 1510 moves upwards (proximally) in the +z direction through the passage 1623 created by the plurality of rigid strips 1620 and is no longer in contact with the distal internal surface 1311 of the elongate rigid members 1300, the rigid strips 1620 gradually retract inwards to accommodate the decreasing taper of the distal obturator tip 1513 which is being removed. The force on the expansion assembly 1500 by the rigid strips 1620 causes the first housing 1100 to move vertically upwards (proximally) in the +z direction, following the direction of the expansion assembly 1500. The proximal region of the internal surface 1323 of the elongate rigid members 1300 maintains a larger passage cross-sectional area than the distal region of the elongate rigid members 1300 which has retracted, shown by a gradual taper of decreasing cross-sectional area 1360 throughout the passage.

With particular reference to FIG. 9D, when the expansion assembly 1500 is completely removed, the rigid strips 1620 retract back to their original shape where the passage created by the internal surfaces of the rigid strips 1620 is back to its smallest passage 1623, and the elongate rigid members 1300 retract back to their smallest cross-sectional area 1340.

In another embodiment, the same effect described above can be generated by removing the fixed diameter cannula 1520 alone and without an obturator 1510, in order to retract the expandable cannula device 100.

Turning to FIGS. 10A-10E, another exemplary embodiment of an expandable cannula device 100 (generally similar to the device of FIGS. 1A-1D) is shown, wherein an obturator 1000 with a distal tip 1030 that has complimentary geometry to the distal tip internal surface 1331 of the elongate rigid members 1300, e.g., to create a substantially seamless internal and external interface with the elongate rigid members 1300 at the retracted state. Current obturators and cannulas do not have seamless interfaces and thus may lead to higher insertion forces, wherein the cannula may tug and drag the tissue in which it is being inserted in causing further trauma. Sometimes they may not penetrate the tissue or fascial layer fully either. The seamless interface created in this embodiment may greatly reduce the insertion force and damage to the tissue and would be appreciated by as novel and non-obvious by person versed in the art.

With particular reference to FIG. 10A, in this exemplary embodiment, the obturator 1000 includes a solid shaft 1020 with a smaller or same cross-sectional area to the inner cross-sectional area of the passage 1340 created by the elongate rigid members 1300 at the retracted state, which extends distally to a tapered distal tip 1030, where the proximal part of the tapered tip 1030 increases in cross-sectional area to a point where the cross-section 1032 is equivalent in area to the cross-section defined by the most distal region 1330 of the elongate rigid members 1300 at their unexpanded (retracted) state 1340. The obturator tip 1030 keeps extending distally past the cross-section 1032 but with a decreasing cross-sectional area until it terminates to create a desired tip shape, which can be sharp, blunt, dolphin-nosed, or may comprise a Veress needle or other alternatives (as shown in FIGS. 13 A-C).

In this embodiment, the distal tip internal surface 1331 of the elongate rigid members 1300 is tapered outwards on the distal end where the angled taper is parallel to that of the obturator tip 1031, such that the most distal tips 1330 of the elongate rigid members 1300 create a larger inner cross-sectional area than the region proximal to the taper.

In an alternative embodiment, the first housing 1100 may house a resistive member 1600 in the cavity 1160.

With particular reference to FIGS. 10B-10C, in this exemplary embodiment, the obturator 1000 is inserted concentrically through the first housing 1100 and is guided towards the passage 1340 created by the internal surfaces of the elongate rigid members 1300. As the larger cross-sectional area region 1032 of the obturator tip 1030 comes in contact with the distal internal surfaces 1311 of the elongate rigid members 1300, the obturator tip 1030 applies a force on the distal internal surfaces 1311 such that it creates a convex bend 1370 in the elongate rigid members 1300 at the point of contact momentarily. This is not feasible in conventional trocars with rigid and fixed diameter cannulas because the rigid cylinder would prevent any object that has a larger cross-sectional area than their internal diameter from passing through.

With particular reference to FIGS. 10D-10E, the obturator also comprises a cylindrical head 1010 which has an inner diameter greater than the outer diameter of the first housing 1100 but smaller than the outer diameter of the second housing 1200 and a height larger than the exposed height of the first housing 1100.

In another embodiment, the cylindrical head 1010 height can be at least equal to said exposed height of the first housing 1100 such that the distal surface 1011 of the obturator head 1010 comes into contact with the proximal surface 1240 of the second housing 1200. It may also have cuts 1013 throughout for improve hand and finger grips.

When the obturator 1000 is inserted completely, the obturator tip taper 1031 becomes flush with the internal surface 1331 of the elongate rigid members 1300 as their complimentary tapers align, causing the elongate rigid members 1300 to retract around the obturator shaft 1020 and lose its convex bend 1370 and create a tight and straight fit 1380 with the obturator 1000. The distal interface of the elongate rigid members 1300 and obturator tip 1030 have a seamless internal and external interface, where the larger inner cross-sectional area created by the distal tips 1330 of the elongate rigid members 1300 is not only parallel to but also lined up and in contact with largest diameter of the obturator tip 1032, such that if this expandable cannula device 100 were to be inserted in tissue, the seamless interface would allow for a smooth insertion.

Simultaneously, the distal surface 1011 of the obturator head 1010 is in contact with the proximal surface 1240 of the second housing 1200 and preventing the obturator 1000 from being inserted further, thereby creating a mechanical stop. In this embodiment the mechanical stop interface is also forming a seamless interface, but in other embodiments it may not form a seamless interface. If the obturator 1000 were to be inserted further due to the obturator head 1010 not extending to the proximal surface 1240 of the second housing 1200, the obturator tip 1030 could protrude from the elongate rigid members 1300, losing the seamless interface, and the obturator head 1010 could apply force on the first housing 1100 causing it to move vertically downwards (distally) causing unwanted expansion of the elongate rigid members 1300.

In an alternative embodiment, the complimentary geometry (shape, size and angle) 1031 of the distal tip 1030 and distal internal surface 1331 of the elongate rigid members 1300 may differ, and have a cylindrical interface, for example.

In alternative embodiments, the obturator head 1010 and the distal surface 1011 may comprise a user-controlled attachably-detachable mechanism that engages and disengages with the second housing 1200 and the proximal surface 1240. Examples of such mechanism include cantilever latch mechanisms or twist-lock mechanisms, or other mechanisms that are known in the art.

Turning to FIGS. 11A-11E, the previously described expandable cannula device 100 (of FIGS. 10A-10E) is shown, wherein the passage created by the distal internal surfaces 1311 of the elongate rigid members 1300 is expanded prior to obturator 1000 entry.

With particular reference to FIG. 11A, as previously described and with reference to the coordinate system in FIG. 1C and the rightmost elongate rigid member 1300 shown in this cross section figure, vertical force in the −z direction is applied on the first housing 1100 relative to the second housing 1200, where the vertical force in the −z direction causes rightmost elongate rigid member 1300 to move outwards to the right in the +x direction, where the diagonal rail 1321 of the elongate rigid member 1300 moves along the diagonal groove 1130 in the first housing 1100, and where the horizontal rail 1322 moves along the horizontal groove 1230 in the second housing 1200. The same outwards motion occurs for the other elongate rigid members 1300, where they are moving away from each other, thus increasing the cross-sectional area of the passage created by the distal internal surfaces 1311 of the elongate rigid members 1300, expanding the passage 1390 of the expandable cannula device 100 slightly to make room for the obturator 1000.

With particular reference to FIG. 11B, in this exemplary embodiment, the obturator 1000 is inserted through the first housing 1100 and is guided towards the passage 1390 created by the internal surfaces of the elongate rigid members 1300, where the inner cross-sectional area of this passage is greater than the outer cross-sectional area of the obturator tip 1030.

With particular reference to FIGS. 11C-11D, in this exemplary embodiment, when the obturator head 1010 comes in contact with the proximal surface of the second housing 1200, the obturator tip 1030 is not flush with the internal surface taper of the distal tip 1331 of the elongate rigid members 1300 as the first housing 1100 remains downwards (distally), causing the elongate rigid members 1300 to be expanded.

To retract the elongate rigid members 1300 and create a flush interface between the obturator tip 1030 and the internal surface taper of the distal tip 1331 of the elongate rigid members 1300, an upwards (proximal) force on the first housing 1100 through the cuts in the obturator head 1010 is applied to move the first housing 1100 vertically upwards (proximally) in the +z direction with respect to the second housing 1200, causing the elongate rigid members 1300 to move together again where the cross-sectional area of the passage created by the distal internal surfaces 1311 of the elongate rigid members 1300 decreases. The distal interface of the elongate rigid members 1300 and obturator tip 1030 have a seamless internal and external interface 1380, such that if this expandable cannula device 100 were to be inserted in tissue, the seamless interface would allow for a smooth insertion.

With particular reference to FIG. 11E, in this exemplary embodiment, the obturator head 1010 has cuts in its side 1013 that allow for the first housing 1100 to be able to be pulled upwards (proximally).

In an alternative embodiment, the obturator head 1010 may come into contact and become flush with the second housing 1200 in a different way.

Turning to FIGS. 12A-12D, the previously described expandable cannula device 100 (of FIGS. 10A-11E) is shown being manipulated in reverse, wherein the obturator tip 1030 that has complimentary geometry to the distal internal surface 1311 of the elongate rigid members 1300 is removed from the expandable cannula device 100, and the elongate rigid members 1300 retract back to their smallest cross-sectional area.

With particular reference to FIGS. 12A-12C, in this exemplary embodiment, an upwards (proximal) force is applied on the distal surface 1011 of the obturator head 1010 to begin removal of the obturator 1000. Upon obturator 1000 removal, the larger cross-sectional area 1032 of the obturator tip 1030 applies force on the distal internal surface 1311 of the elongate rigid members 1300 causing the inner cross-sectional area of the passage created by the distal internal surfaces 1311 of the elongate rigid members 1300 to increase in diameter to equal the outer cross-sectional area of the obturator tip 1030. The force applied by the obturator tip 1030 on the distal internal surface 1311 of the elongate rigid members 1300 causes a convex bend.

With particular reference to FIG. 12D, when the obturator tip 1030 is no longer in contact with the distal internal surfaces 1311 of the elongate rigid members 1300, the elongate rigid members 1300 retract back to their smallest cross-sectional area 1340.

In an alternative embodiment, the obturator 1000 is removed by first moving the first housing 1100 vertically downwards (distally) with respect to the second housing 1200 to cause the elongate rigid members 1300 to move away from each other first before removing the obturator 1000.

Figure 13C:
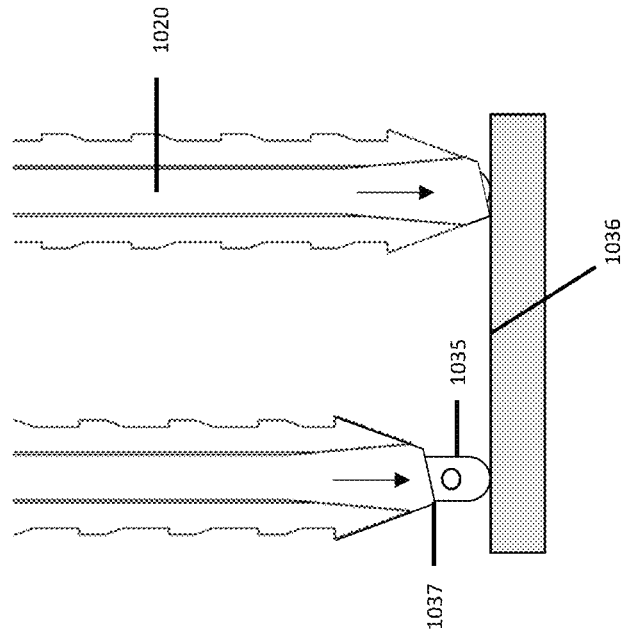
FIGS. 13A-13C are cross-sectional side views of exemplary embodiments of obturator tips that may be provided on an obturator used with the cannula devices of FIGS. 10A-11E.
Figure 13B:
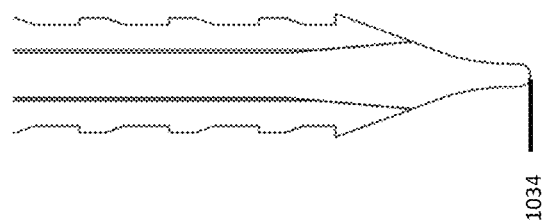
Figure 13A:
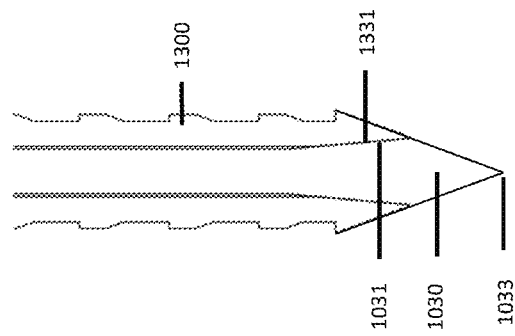

Turning to FIGS. 13A-13C, exemplary embodiments of obturator tips 1030 are shown, wherein the proximal surface of the obturator tip region 1031 with complimentary geometry to the internal surface 1331 of the elongate rigid members 1300 remains the same, but the exposed tip has several possible geometries.

For example, with particular reference to FIG. 13A, an exemplary embodiment of the previously described obturator tip 1030 is shown, wherein the proximal surface of the obturator tip region 1031 with complimentary geometry to the internal surface 1331 of the elongate rigid members 1300 remains the same, but the exposed tip is in the shape of a sharp tip 1033.

With particular reference to FIG. 13B, the previously described obturator tip 1030 of FIG. 13A is shown, wherein the proximal surface of the obturator tip region 1031 with complimentary geometry to the internal surface 1331 of the elongate rigid members 1300 remains the same, but the exposed tip is in the shape of a dolphin nose 1034, shown by concave edges and a blunt tip.

With particular reference to FIG. 13C, another exemplary embodiment of an obturator tip 1030 is shown, wherein the proximal surface of the distal tip region 1031 with complimentary geometry to the internal surface 1331 of the elongate rigid members 1300 remains the same, but the exposed tip 1037 includes a Veress needle 1035. The Veress needle tip is spring-loaded such that as it comes in contact with a surface 1036, the surface 1036 applies an upwards (proximal) force on the Veress needle tip 1035 causing it to retract upwards (proximally) in the +z direction in the obturator shaft 1020, allowing the sharp surface of the tip 1037 to penetrate the surface 1036. Veress needle tips are commonly used in laparoscopic surgeries.

Turning to of FIGS. 14A-14E, another exemplary embodiment of an expandable cannula device 100 is shown that is generally similar to previous embodiments, except that the distal region 1330 of the elongate rigid members 1300 come together to form a seamless and closed tip 1332 which allows the expandable cannula device 100 to be used without an obturator 1000 as the closed tip 1332 will replicate the functionality of an obturator 1000 and can also be used with a navigational member 2500 or expanded to a larger diameter with an expansion assembly 1500.

With particular reference to FIGS. 14A-14B, in this exemplary embodiment, the distal region 1330 of the elongate rigid members 1300 come together to form a seamless and closed tip 1332 which allows the expandable cannula device 100 to be used without an obturator 1000 as the closed tip 1332 will replicate the functionality of an obturator 1000.

In alternative embodiments, the closed tip 1332 can vary in angle and shape and can be either sharp or blunt.

With particular reference to FIGS. 14C-14D, in this exemplary embodiment, a navigational member 2500 such as an optical or electromagnetic navigation probe may be inserted through the lumen 1340 of the elongate rigid members 1300 and rest on the flat internal surface 1333 of the closed tip 1332 to provide locational data about the closed tip 1332 of the expandable cannula device 100 when inserting into tissue. This embodiment is useful for neurosurgical applications where navigation probes are commonly used to identify the tip location in the brain. The navigational probe 2500 can also be locked proximally relative to the first housing 1100 or the second housing 1200 or both via a set-screw mechanism or a resistive member 1600 that is located in the first housing as described previously.

With particular reference to FIG. 14E, in this exemplary embodiment, the expandable cannula device 100 can be inserted into tissue and an expansion assembly 1500 can be inserted as in previously described embodiments to expand the elongate rigid members 1300, and where the distal surface 1525 of the fixed diameter cannula 1520 is flat and rests on the flat internal surface 1333 of the closed tip 1332 of the elongate rigid members 1300.

In alternative embodiments, the distal surface 1525 of the fixed diameter cannula 1520 can connect to the internal surface 1333 of the closed tip 1332 of the elongate rigid members 1300 in a variety of different complimentary ways and shapes.

Turning to FIGS. 15A-15D, another exemplary embodiment of an expandable cannula device 100 is shown in unexpanded 1340 and expanded 1350 states that is generally similar to previous embodiments except that the cannula device includes a first sealing elastic member 1710 and a second sealing elastic member 1720 covering exterior surfaces of the expandable cannula device 100, where the second sealing elastic member 1720 is assembled in different ways. A one-way valve 1190 and a resistive member in the form of a backup valve 1610 is located in the cavity 1160 in the proximal region of the first housing 1100, creating a fluid seal preventing fluid transfer between the lumen of the cannula and the exterior environment, even when instruments are entered into the cannula.

With particular reference to FIG. 15A, in this exemplary embodiment, the first sealing elastic member 1710 is an elastic member which covers the exterior surface 1312 of the elongate rigid members 1300 from the distal tips 1330 upwards (proximally) to the exterior surface 1270 of the second housing 1200. The first sealing elastic member 1710 may be an elastomer with a low shore hardness and high elongation and tensile strength, such as silicone, polyisoprene or neoprene, and may be manufactured through dip molding, coating or casting methods, and potentially through multi-cycle dip coating.

The proximal portion 1713 of the first sealing elastic member 1710 may be kept in place on the second housing 1200 using a glue. The distal portion 1714 of the first sealing elastic member 1710 may be kept in place on the distal tip 1330 of the elongate rigid members 1300 using a glue.

In an alternative embodiment, the first sealing elastic member 1710 may be stretched in the unexpanded state 1340 of the elongate rigid members 1300 where the elasticity is sufficient to keep the first sealing elastic member 1710 in firm contact with the exterior surface of the elongate rigid members 1300 without a permanent glue.

The first sealing elastic member 1710 may be assembled onto the expandable cannula device 100 by being rolled up from the distal end 1330 of the elongate rigid members 1300 and permanently or non-permanently held by the second housing 1200.

In an alternative embodiment, the first sealing member 1710 may have surface modifications such as thicker regions or ribs to provide better retention in tissue.

In this embodiment, the second sealing elastic member 1720 is an elastic member which covers the region between the proximal surface 1140 of the first housing 1100 where the throughbore 1110 begins, and the second housing 1200.

The second sealing elastic member 1720 may be an elastomer made of the same material as the first sealing elastic member 1710 as described previously.

The proximal portion 1723 of the second sealing elastic member 1720 may be kept in place on the first housing 1100 by compressing or pinching it underneath a cap 1180 that attaches to the first housing 1100 via press-fit or threading mechanism, which simultaneously compresses a resistive member 1610 to create a tight seal and prevent gas loss.

The combination of the first sealing elastic member 1710 and the second sealing elastic member 1720 prevents fluid leaks from around the elongate rigid members 1300, between the concentric interfaces of the first housing 1100 and second housing 1200, and between the elongate rigid members 1300 and the second housing 1200 as it completely seals the expandable cannula device 100 from the tip 1330 of the elongate rigid members 1300 to the proximal surface 1140 of the first housing 1100. However, the first sealing elastic member 1710 and second sealing elastic member 1200 do not prevent leakage from the throughbore of the cannula, as this is done using a valve system described later (FIG. 32).

With particular reference to FIG. 15B, in this exemplary embodiment, upon expansion of the expandable cannula device 100, the first sealing elastic member 1710 stretches 1712 to accommodate the increasing cross-sectional area of the external surfaces 1312 of the elongate rigid members 1300, while the second sealing elastic member 1720 contracts 1722 to accommodate the first housing 1100 moving vertically downwards (distally) with respect to the second housing 1200. Both the first sealing elastic member 1710 and the second sealing elastic member 1720 remain intact during expansion and retraction in order to maintain a fluid seal and prevent fluid from transferring between the lumen of the cannula and the exterior environment.

In an alternative embodiment, the sealing members 1710 and 1720 may comprise of more than one layer of material and/or including mesh structures.

In an alternative embodiment, the sealing members 1710 and 1720 may be attachably detachable from the expandable cannula device 100.

In an alternative embodiment, the sealing members 1710 and 1720 may be heat shrinkable.

In an alternative embodiment, the first sealing elastic member 1710 may aid in retracting the expandable cannula device 100 when no expansion assembly 1500 is present. When the first sealing elastic member 1710 is in its expanded state 1712, it is experiencing tension which in turn is applying a radial inwards force on the external surface 1312 of the elongate rigid members 1300, causing them to contract to the unexpanded the state 1340 thereby causing the first sealing elastic member 1710 to return to an initial state that has minimal or no tension 1711.

In an alternative embodiment, the retraction of the expandable cannula device 100 can be initiated by an expansion assembly 1500 being removed with a resistive member 1610 as in FIGS. 5A-5E, where the upwards (proximal) removal of the obturator tip 1513 initiates:

1) the distal region 1310 of the elongate rigid members 1300 to contract due to the first sealing elastic member 1710 applying a radial inwards force on the external surface 1312 of the elongate rigid members 1300 as described above, and
2) the resistive member 1600 to follow the obturator tip 1523 and cause the first housing 1100 to move upwards (proximally) causing the proximal region 1320 of the elongate rigid members 1300 to contract back to their smallest cross-sectional area 1340.

With particular reference to FIG. 15C-15D, an alternative exemplary embodiment is shown, where the proximal portion 1723 of the second sealing elastic member 1720 may be kept in place on the first housing 1100 by placing an O-ring 1750 or similar elastic part over the second sealing elastic member 1720 in a groove created between the first housing 1100 and a cap 1180 followed by folding the proximal portion 1723 over the O-ring 1750. This creates a tight seal and prevents gas loss from the moving parts that are enclosed within the second sealing elastic member 1720.

The distal portion 1724 of the second sealing elastic member 1720 may also be kept in place on the second housing 1200 using a glue or an O-ring 1750 mechanism as described above.

Turning to FIGS. 16A-16B, an alternative embodiment of the previously described first sealing elastic member 1710 and the second sealing elastic member 1720 (of FIGS. 15A-15D) is shown, wherein the first sealing elastic member 1710 remains the same and the second sealing member is flexible but not stretchable and can be accordioned or corrugated 1730 such that when the cannula 100 is expanded, the surfaces of the accordioned shape 1735 come closer together causing the outer cross-sectional area of the second sealing member 1730 to increase.

In some embodiments, the second sealing member 1730 may resemble bellows, corrugations, waves, zig-zag folds, and other accordioned shapes.

In some embodiments, the second sealing member 1730 may be made of a fabric or polymer material that is relatively difficult to stretch, e.g., modulus of elasticity in the range of 12-2000 MPa.

Figure 17B:
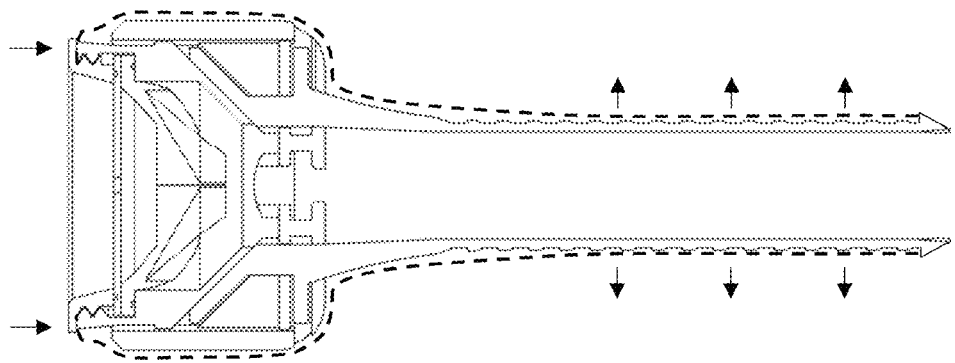
FIGS. 17A-17B are cross-sectional side views of an exemplary embodiment of an expandable cannula device including a single sealing elastic member.
Figure 17A:
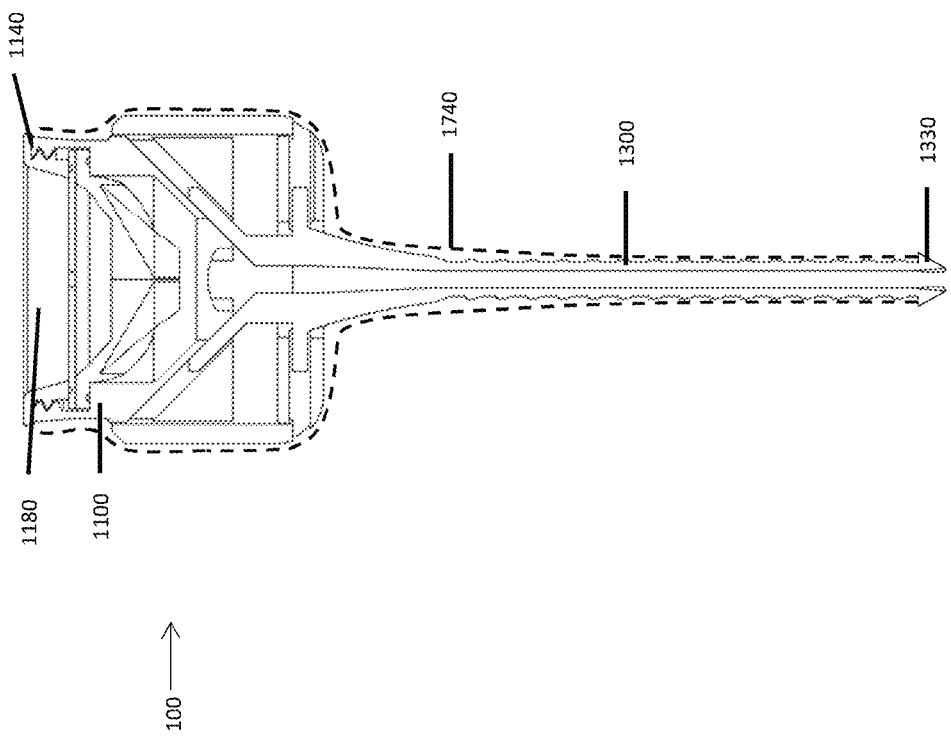

Turning to FIGS. 17A-17B, another exemplary embodiment of an expandable cannula device is shown that is generally similar to the previous embodiments, except that a single sealing elastic member 1740 is provided, where the functionality remains the same; remaining intact during expansion and retraction in order to maintain a fluid seal and prevent fluid from transferring between the lumen of the cannula and the exterior environment.

The single sealing elastic member 1740 may be comprised of various different elastomeric materials with a high elongation and tensile strength, such as a dip-molded silicone, polyisoprene or neoprene, and may be hydrophobic or hydrophilic.

The single sealing elastic member 1740 may be assembled by pulling the entire member over the expandable cannula device 100 from the distal tip 1330 of the elongate rigid members 1300 upwards (proximally) to the proximal surface 1140 of the first housing 1100 where it may be kept in place by compressing it underneath a valve cap 1180, by using a glue or by holding it in place via an O-ring 1750 mechanism as described earlier.

Figures 18A, 18B:
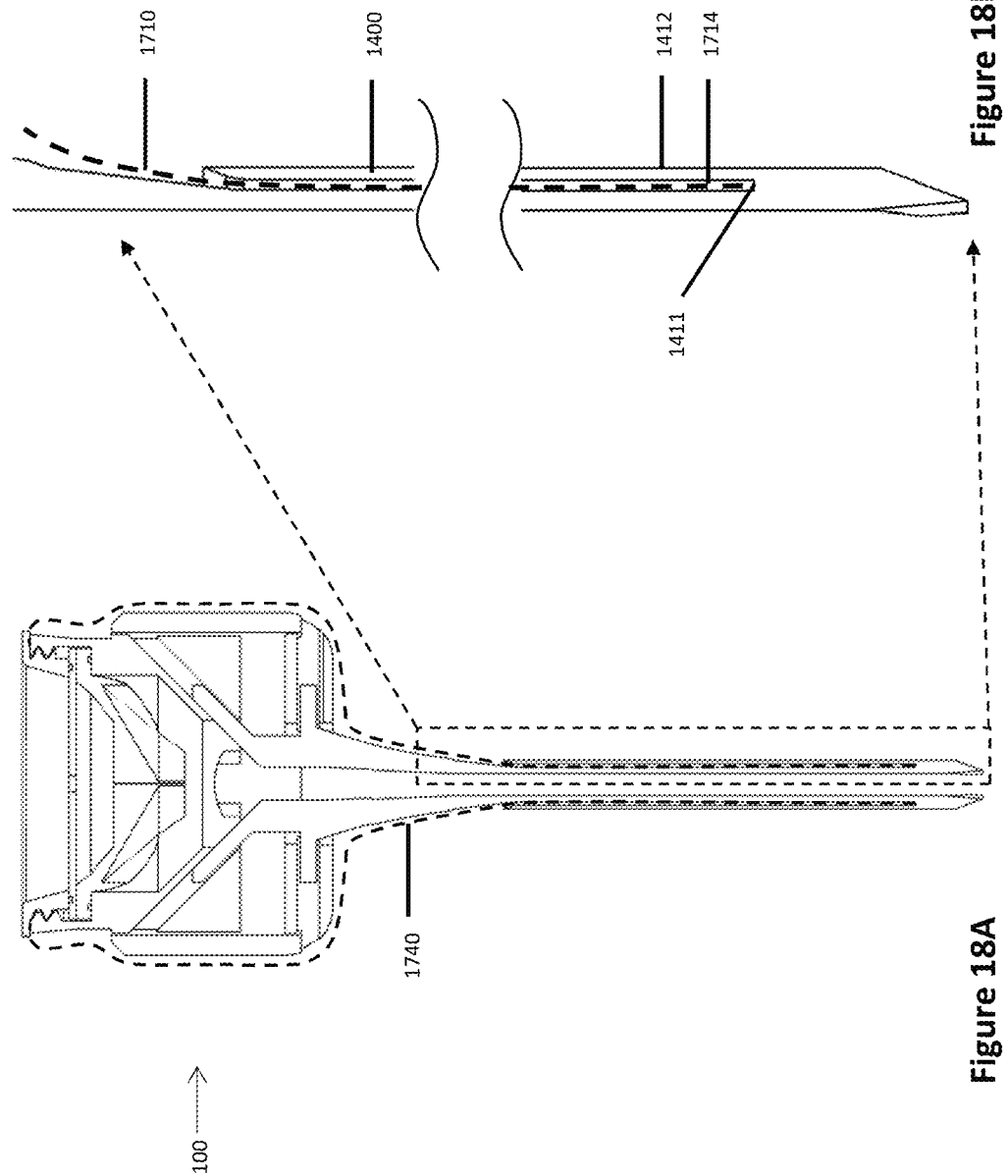

Turning to FIGS. 18A-18B, another exemplary embodiment of an expandable cannula device is shown generally similar to previous embodiments. In reference to the previous embodiment, the first sealing elastic member 1710 or the single sealing elastic member 1740 are both referred to interchangeably in this embodiment and set of figures. This is because the first sealing elastic member 1710 still describes the distal section and surrounds the external surfaces 1312 of the elongate rigid members 1300. The sealing member 1710 is therefore exposed to external forces such as friction from tissue during insertion, which may lead to the first sealing member 1710 catching on surfaces, tearing or rolling up the elongate rigid members 1300. In this alternative embodiment, the previously described elongate rigid members 1300 are described where they protect the first sealing member 1710 using a u-shaped 1400 geometry.

With particular reference to FIG. 18A-18B, in this exemplary embodiment, the elongate rigid members are u-shaped 1400, wherein a groove 1411 is located along the external surface 1412 of the straight portion of the elongate rigid members 1400, resembling a u-channel or slot 1411 where a first sealing member 1710 may be inserted.

In this embodiment, a first sealing member 1710 is placed within the u-channel 1411. The external surface 1412 of the u-shaped elongate rigid member 1400 protects the first sealing member 1710 by preventing external forces from directly acting on it and potentially rolling up the distal end 1714 or creating a tear during initial entry in tissue.

The u-shaped elongate rigid member 1400 may also aid in preventing gas loss from the distal end of the expandable cannula device as it removes all possible gaps between the distal ends of the u-shaped elongate rigid members 1400 and the distal end 1714 of the first sealing member 1710.

The first sealing member 1710 may be glued to the u-shaped elongate rigid members 1400 on either surface within the u-channel 1411.

Figures 27C, 27D:
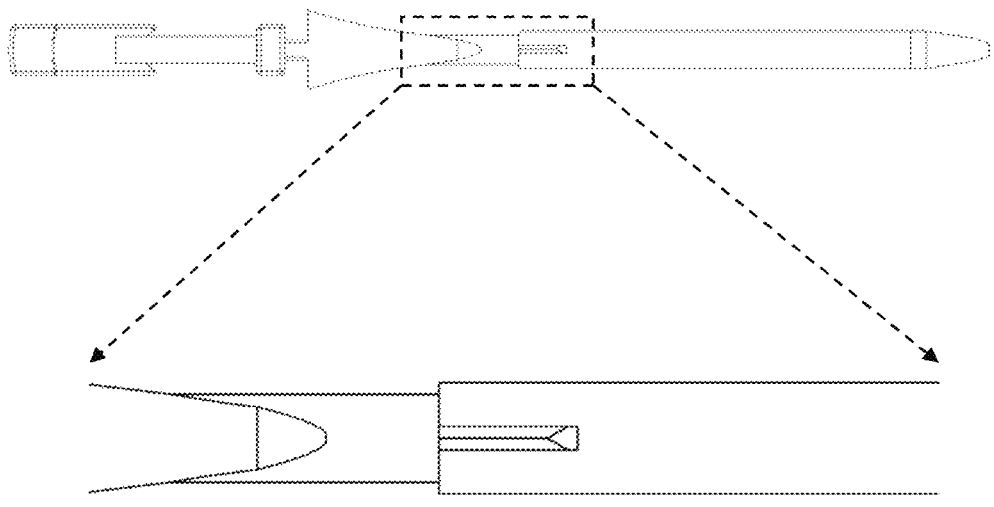
FIGS. 27A-27D are side and front views of an exemplary embodiment of a 'u-shaped' elongate rigid member for an expandable cannula device with a blade for the purpose of extending an incision in tissue when the cannula device is expanded.
Figures 27A, 27B:
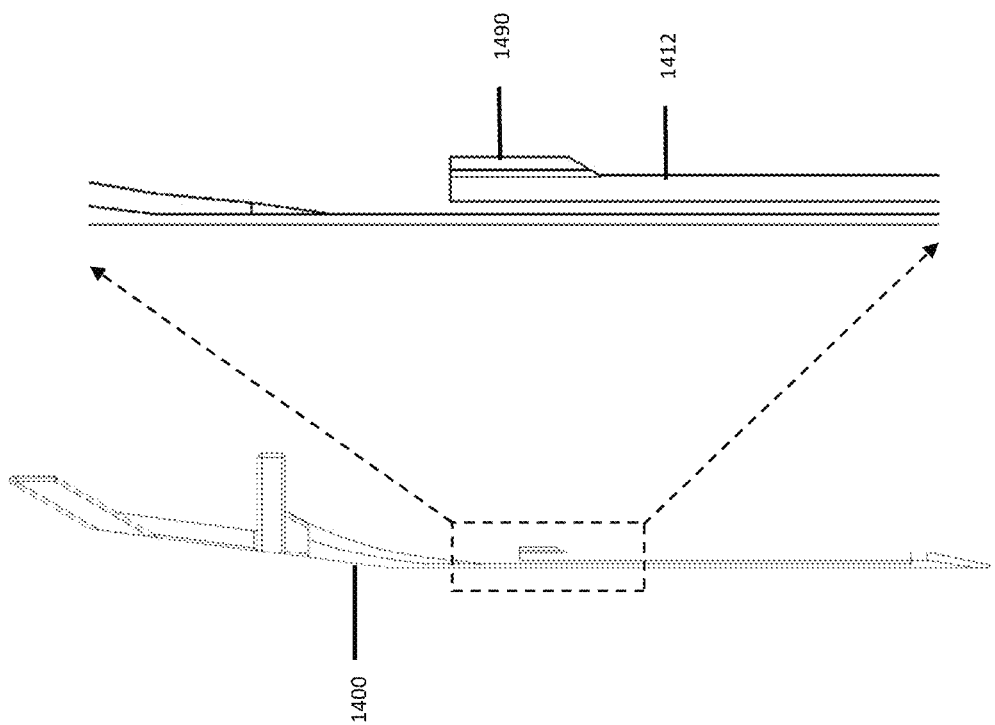

In the following embodiments, the u-shaped elongate rigid members 1400 may not only protect the first sealing member 1710 but also allow for any surface modifications to the external surface 1412 of the elongate rigid members 1400 to increase fixation, guide an incision or house a blade to create an incision, as described in FIGS. 26-28.

In an alternative embodiment, the u-channel 1411 may not be as deep and may resemble a small groove in the proximal end of the current u-shaped elongate rigid members 1400, as described in FIG. 20.

Turning to FIGS. 19A-19B, an alternative exemplary embodiment of the previously described u-shaped elongate rigid members 1400 (FIG. 18) is shown. In this embodiment, the external surface 1412 of the u-shaped elongate rigid members 1400 has surface modifications 1413 on the external surface 1412 to enhance the fixation of the expandable cannula device 100 in tissue, such that it increases contact and friction with tissue and reduce the likelihood of the cannula from slipping out of the tissue.

In alternative embodiments, the surface modifications 1413 may be in the form of ridges, threads, any extrusions or extruded cut.

Turning to FIGS. 20A-20B, an alternative exemplary embodiment of the previously described u-shaped elongate rigid members 1400 (FIGS. 18-19) is shown. In this example, the external surface 1412 of the u-shaped elongate rigid members 1400 has surface modifications 1413, and the u-channel is in the form of a small groove 1420 in the most distal surface modification 1430 of the u-shaped elongate rigid members 1400 which may be larger in width that the proximal surface modifications.

The first sealing member 1710 may be inserted into the groove 1420 in the most distal surface modification 1430 and wrap tightly around the additional surface modifications. The most distal surface modification 1430 prevents the sealing member from rolling up from friction when the expandable cannula device 100 is inserted in tissue.

The first sealing member 1710 may or may not be glued in the groove of the most distal surface modification 1430.

Turning to FIGS. 21A-21B, an alternative exemplary embodiment of the previously described elongate rigid members 1400 is shown. In this embodiment, the external surface of elongate rigid members 1400 has surface modifications 1413, where the most distal surface modification is larger in diameter, thickness or cross-sectional area than the proximal surface modification features.

The first sealing member 1710 may be wrapped tightly around the proximal surface modifications and sit proximal to the most distal surface modification 1430, such that it creates a leading edge and surface into the tissue, which in turn may prevent the first sealing member 1710 from coming in direct contact with tissue and prevent it from rolling up due to friction from inserting the expandable cannula device 100 in tissue.

The first sealing member 1710 may be glued behind the most distal surface modification 1430.

Turning to FIGS. 22A-22D and 23A-23D, an alternative exemplary embodiment of the previously described u-shaped elongate rigid members 1400 (FIGS. 18-19) is shown. In this embodiment, the u-shaped elongate rigid members 1400 can be separated into an interior piece 1451 and exterior piece 1452, wherein the exterior piece 1452 can be attached to the interior piece 1451 to form a u-channel 1411 for the first sealing member 1710 to be inserted.

With particular reference to FIGS. 22A-22D, in this exemplary embodiment, the exterior piece is a tongue 1452 and the interior piece is a groove 1451 in the distal tip 1440, where the exterior piece 1452 can slide into the interior piece 1451 and lock in place.

In alternative embodiments, the exterior piece 1452 may lock in place by way of a press fit or glue/epoxy, and/or may have surface modifications 1413.

In an alternate embodiment, the fit may be in the form of a lock and key or may be detachably attachable.

With particular reference to FIGS. 23A-23D, in this alternative exemplary embodiment, the exterior piece is a groove 1453 in the distal tip 1440 and the interior piece 1454 is a tongue. The interior piece 1454 can slide into the groove in the exterior piece 1453 to lock in place.

In alternative embodiments, the exterior piece 1453 may lock in place by way of a press fit or glue/epoxy, and/or may have surface modifications 1413.

The first sealing member 1710 may be inserted in the u-channel 1411 and locked in place before or after the interior and exterior pieces are assembled.

Turning to FIGS. 24A-24D, in this alternative exemplary embodiment, the exterior piece has extruded surface modifications 1461 that press-fit into the cut surface modifications in the interior piece 1462, which can compress the first sealing member 1710 or pierce through it to lock it in place.

Turning to FIGS. 25A-25B, in this alternative exemplary embodiment, the exterior piece 1471 comprises a distal tip 1440 and two grooves 1472 in the internal surface of the region where the distal tip ends and the u-channel begins 1473, and the interior piece 1474 comprises the entire elongate rigid member 1400 wherein the distal region has two rails along either side 1475. The exterior piece 1471 can slide on the interior piece 1474 distally via the rails 1475 and grooves 1472 and be glued in place to form the u-channel. In alternative embodiments, the rail configuration geometry may differ.

Turning to FIGS. 26A-26D, in this alternative exemplary embodiment, the external surface 1412 of the proximal region of the u-shaped elongate rigid member 1400 contains a vertical groove/guide 1480 for making an incision using a blade to create an incision of a predetermined dimension and shape, in the case where the expandable cannula device 100 must be expanded to a larger size.

Turning to FIGS. 27A-27D, in this alternative exemplary embodiment, the u-shaped elongate rigid member 1400 comprises a cannula with at least one blade 1490, located on the exterior surface 1412 of the proximal region of the u-shaped elongate rigid member 1400. In a situation where the expandable cannula device 100 must be expanded to a larger size, the incision in the skin will be extended using a scalpel, however in this embodiment, a blade 1490 is integrated into the u-shaped elongate rigid member 1400 such that the incision can be extended without surgeon interference to provide a streamlined expansion.

Upon expansion of the elongate rigid members 1400, the blade 1490 comes in contact with the tissue and applies a force which immediately cuts the tissue. When the device is expanded, the blade 1490 is no longer applying a force on the tissue and is therefore not cutting further.

In an alternative embodiment, a user can tilt the expandable cannula device 100 in the direction of the blade 1490 to apply force on the tissue and cut through it.

Turning to FIGS. 28A-28E, in this alternative exemplary embodiment, the blade 1490 may have a cover 1491 to prevent the blade 1490 from undesired activation. The blade cover 1491 may be in the form of a sliding door or removable cover.

Turning to FIGS. 29A-29D, an exemplary embodiment of an expandable cannula device 100 is shown, wherein the expansion of the elongate rigid members 2000 is actuated by a hinge system 2100 connecting the first housing 1800 to the elongate rigid members 2000.

With particular reference to FIGS. 29A-29B, an exemplary embodiment of an expandable cannula device 100 is shown comprising a cylindrical first housing 1800 defining a first throughbore 1810; a plurality of elongate rigid members 2000 cooperatively defining a passage axially aligned with the first throughbore 1810; a hinge system 2100 connecting the elongate rigid members 2000 to the first housing 1800, a second housing 1900 defining a second throughbore 1910, the second housing 1900 is concentric with the first housing 1800 and moveable in a vertical direction with respect to the first housing 1800, the second housing 1900 being operably connected to the elongate rigid members 2000 such that vertical movement of the first housing 1800 with respect to the second housing 1900 causes the hinge system 2100 to force the elongate rigid members 2000 away from each other and increases the cross-sectional area of the passage 2040.

In this embodiment, the plurality of elongate rigid members 2000 comprises an inner surface 2010 and an outer surface 2011, a proximal horizontal rail 2030 perpendicular to the long axis of the elongate rigid member 2000 which is complimentary to a horizontal groove 1920 in the second housing 1900, and a pin 2130 on the outermost edge of the horizontal rail 2030 perpendicular to the horizontal groove 1920 in the second housing 1900. The inner surfaces 2010 of the plurality of elongate rigid members 2000 form the cross-sectional area of the passage.

In this embodiment, the first housing 1800 comprises a plurality of vertical grooves/cuts 1820, where each groove 1820 has a pin 2120 that is fixed on either side of the groove near the edge of the throughbore 1810, perpendicular to the cut 1820, which connects to an elongate rigid link 2110.

In an alternative embodiment, the first housing may resemble a hollow cylinder or ring.

In this embodiment, the second housing 1900 comprises a plurality of horizontal grooves or cuts 1920, where each horizontal groove 1920 is complimentary to the horizontal rail 2030 of the elongate rigid member 2000, and where there is a cut on the proximal face of the second housing 1900 to allow for the elongate rigid links 2110 to move freely.

In this embodiment, the hinge system 2100 comprises a plurality of elongate rigid links 2110 with symmetric holes on the distal end 2111 and proximal end 2112, a proximal pin 2120 in the first housing 1800, and a parallel distal pin 2130 in the elongate rigid member 2000, where the holes in the elongate rigid links 2110 are complimentary to the diameter of the pins. The elongate rigid links 2110 are connected to each of these pins to allow for rotational motion to occur around the long axis of the pins. A plurality of proximal pins 2120 in the first housing 1800 are closer to the central z-axis in the throughbore 1810 of the first housing 1800 than the distal pins 2130 in the elongate rigid members 2000, creating an initial acute angle when the elongate rigid members are not expanded 2040.

In an alternative embodiment, this initial angle may be increased or decreased to change the rate of axial motion of the first housing 1800 in the second housing 1900, and thus the rate of expansion of the plurality of elongate rigid members 2000.

In an alternative embodiment, the number of elongate rigid links 2110, proximal pins 2120 and distal pins 2130 may be increased.

With particular reference to FIGS. 29C-29D, as previously described and with reference to the coordinate system shown which is the same as in FIG. 1C, and where the second housing 1900 is fixed at an origin, as vertical force in the −z direction is applied on the first housing 1800, the proximal part 2112 of the right elongate rigid link 2110 moves downwards (distally) in the −z direction while rotating at the proximal pin 2120 in the first housing 1800. Since the elongate rigid link 2110 is rigid, its length must remain the same, and since it is pinned at both ends, it must move while maintaining its rigidity. Thus, as the proximal part 2112 of the right elongate rigid link 2110 is forced downwards (distally) in the −z direction, this forces the distal part 2111 of the right elongate rigid link 2110 to move downwards (distally), but since it is attached to the distal pin 2130 in the horizontal rail 2030 of the right elongate rigid member 2000, the right elongate rigid link 2110 forces the horizontal rail 2030 of the right elongate rigid member 2000 to move outwards in the +x direction in the horizontal groove 1920 in the second housing 1900. The same outwards motion occurs for the other elongate rigid members 2000, where they are moving away from each other, thus increasing the cross-sectional area of the passage created by the internal surfaces 2010 of the elongate rigid members 2000, expanding the passage 2050 of the expandable cannula device 100.

The second housing 1900 remains fixed at an origin, while the first housing 1800 is displaced in the −z direction relative to the second housing 1900, the elongate rigid links 2110 have smaller angle than the starting position (in an alternative embodiment the angle can be zero), and the plurality of elongate rigid members 2000 are displaced radially outwards in the relative to the second housing 1900.

In an alternative embodiment, this hinge system 2100 could resemble a slider-crank mechanism.

In an alternative embodiment, the same mechanism of expansion may be used for retraction of the elongate rigid members 2000 by reversing the movement of the first housing 1800 relative to the second housing 1900; that is to move it in the +z direction relative to the second housing.

Turning to FIGS. 30A-30D, another exemplary embodiment of an expandable cannula device 100 is shown, which may be generally similar to any of the previous embodiments, although shown a single sealing elastic member 1740. In this embodiment, the cannula device can be attached to a robotic surgical system 2200 using a mount 2300 that is fixated to the external surface 1270 of the second housing 1200 and to a robotic arm 2200.

Figure 30D:
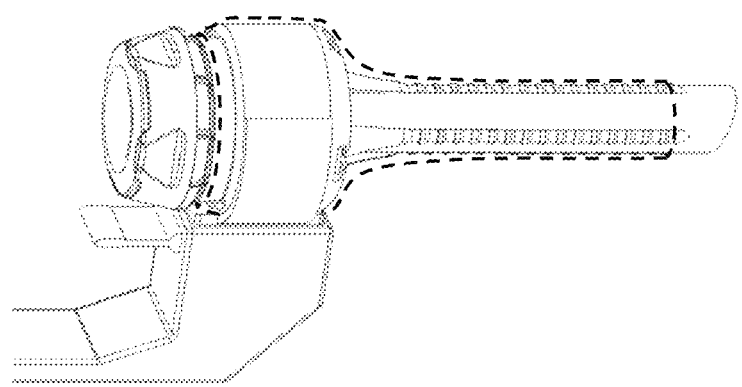
FIGS. 30A-30D are side, top and isometric views of an exemplary embodiment of an expandable cannula device including a mount which is shown being attached to a robotic arm for the purposes of being used with a robotic surgical system.
Figure 30C:
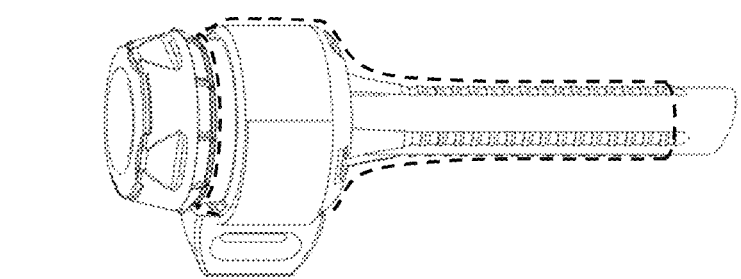
Figure 30B:
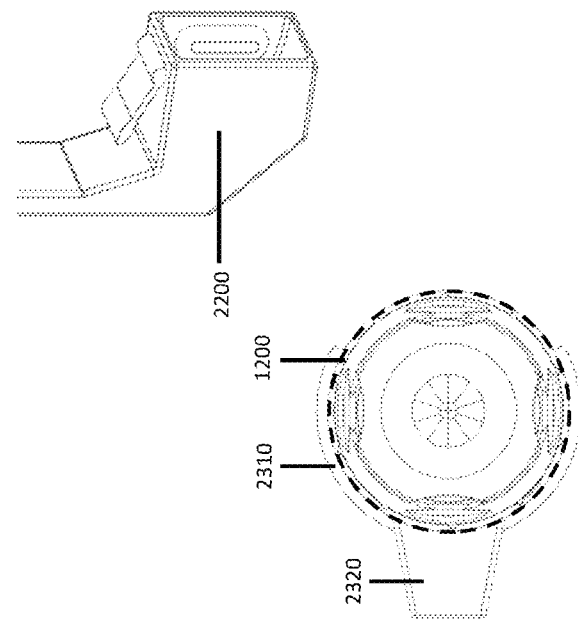
Figure 30A:
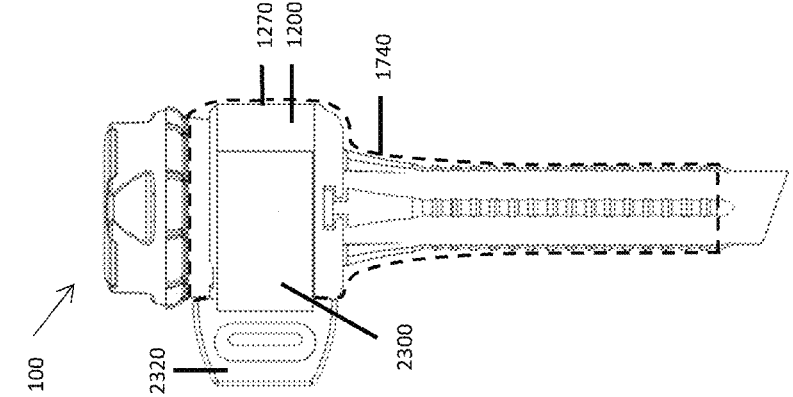

With particular reference to FIGS. 30A-30B, in this exemplary embodiment, the mount 2300 comprises a circular body 2310 with an inner cross-sectional area complimentary to the outer cross-sectional area of the second housing 1200, and an extruded adapter 2320 which can operably be connected to a robotic arm 2200 through any attachably detachable mechanical fixation mechanisms known in the art.

In alternative embodiments, the circular body 2310 of the mount 2300 may have different geometries, internal geometry is complimentary to and can be operably connected to the external surface 1270 of the second housing 1200.

With particular reference to FIGS. 30C-30D, the mount 2300 can be attached to the expandable cannula device 100 using any form of mechanical fixation including a pin, press or friction fit, screw, a series of grooves/rails, a latch mechanism, etc. The mount 2300 can be made of a variety of different rigid materials, including injection molded plastics or metal.

Turning to FIGS. 31A-31F, another example of an expandable cannula device is shown that may be mounted to a robotic arm. In this exemplary embodiment, a compressible mount 2400 is provided, which may or may not be connected to a robotic arm 2200 and can initiate expansion of the expandable cannula device 100 using a mechanical mechanism.

With particular reference to FIGS. 31A-31B, the mount 2400 comprises a proximal piece 2410 and a distal piece 2420 which are connected by a mechanical mechanism 2430 such as a linear actuator that can be actuated to bring the proximal 2410 and distal pieces 2420 closer together or further apart.

The mount mechanism 2430 may be pneumatic, hydraulic, spring-loaded, electrically powered, electromechanically powered system or any other actuation system. The mount 2400 may be actuated to initiate expansion by pressing a button on the mount itself or independently using a remote, wired or wireless controller.

The mount 2400 attaches to the expandable cannula device 100 with contact on the proximal surface 1140 of the first housing 1100 and the distal surface 1250 of the second housing 1200, thereby the actuation of the mechanical mechanism 2430 causes the proximal piece 2410 to apply force on the proximal surface 1140 of the first housing 1100 and the distal piece 2420 to apply force on the distal surface 1250 of the second housing 1200, causing a compression that initiates the expansion of the expandable cannula device 100. The compression can be controlled such that either one of the proximal piece 2410 or distal piece 2420 may be stationary and the other piece to move towards the other, causing the actuation, which may be useful in situations where the depth of the expandable cannula device 100 in tissue must not change during the expansion.

In this embodiment, the proximal region of the internal surface 1323 of the elongate rigid members 1300 creates a larger passage cross-sectional area 1361 than the distal internal surface 1311 of the elongate rigid members 1300, shown by a gradual taper of decreasing cross-sectional area 1360 throughout the passage.

With particular reference to FIGS. 31C-31D, in this exemplary embodiment, an expansion assembly 1500 is inserted downwards (distally) through the throughbore 1110 of the first housing 1100 and the passage 1340 created by the distal internal surfaces 1311 of the elongate rigid members 1300. The distal tip 1513 of the obturator 1510 in the expansion assembly 1500 initiates contact with the distal internal surface 1311 of the elongate rigid members 1300 at the smaller passage cross-sectional area 1362 and causes the distal region 1310 of the elongate rigid members 1300 to expand such that the distal internal surfaces 1311 of the elongate rigid members 1300 surround the expansion assembly 1500.

With particular reference to FIG. 31E-31F, in this exemplary embodiment, the obturator 1510 is removed from the fixed diameter cannula 1520 to allow for instruments to be inserted through the hollow passage 1521 in the fixed diameter cannula 1520. The obturator 1510 is removed by applying a vertical force upwards (proximal) on the distal surface 1512 of the obturator head 1511 such that the fixed diameter cannula 1520 remains in place in the expandable cannula by the elongate rigid members 1300.

In an alternative embodiment not shown, a robotic arm 2200 may be able to guide an expansion assembly 1500 downwards (distally) and concentrically into the expandable cannula device 100 and may utilize the resistive member 1600 initiated expansion as described above and with reference to FIGS. 4A-9D to expand the cannula device 100 to a larger diameter.

Turning to FIGS. 32A-32D, another exemplary embodiment of an expandable cannula device 100 is shown, which may be generally similar to any of the previous embodiments, except that the cannula device includes a side port with a stopcock 1280. As shown, the cannula device also includes a single sealing elastic member 1740 and a one-way valve 1190 and backup valve 1610 which can prevent gas leakage with and without instruments. The cannula device may be used in cooperation with a fixed diameter cannula 1520 including one or more holes, e.g., an array of holes 1524 arranged around a perimeter of a proximal region of the cannula 1520. The fixed diameter cannula 1520 may also include a valve system 1540 with a backup valve 1541 and a one-way valve 1542, which can also prevent gas leakage with and without instruments. The expandable cannula device 100 and fixed diameter cannula 1520 are shown together where the combination of the valve systems and single sealing elastic member 1740 work together to prevent gas leakage from the entire device 100.

With particular reference to FIG. 32A-32B, in this exemplary embodiment, the expandable cannula device 100 is shown with a stopcock 1280 which is configured for injecting or releasing gas through the lumen of the cannula. The stopcock 1280 is connected to expandable cannula device 100 through a hole 1290 in the second housing 1200 which leads to an extruded cut 1170 in the first housing 1100 which allows for gas to travel into the passage created by the throughbore 1110 in the first housing 1100 and the elongate rigid members 1300. The stopcock 1280 may be configured with a lever to control the flow rate of inflowing and outflowing gas.

In this embodiment, the expandable cannula device 100 is covered by a single sealing elastic member 1740, and the first housing 1100 contains a one-way valve 1190 and a resistive member 1610 in the form of a flat backup valve (hereon referred to interchangeably), which are compressed by a resistive member cap 1180. All of these components interact together in preventing gas loss from the expandable cannula device 100 when there are no instruments inserted through it and even when there are instruments inserted through it. The single sealing elastic member 1740 seals the gaps surrounding the elongate rigid member 1300 and the gaps between the first housing 1100 and the second housing 1200, as well as the gaps between the elongate rigid members 1300 and the second housing 1200—all of which has been described at length in previous sections of this description, and particularly in sections related to FIGS. 15A-17B.

In this exemplary embodiment the one-way valve 1190 is a cross-slit valve made out of a silicone or similar material in this embodiment, which prevents gas from flowing up through the valve 1190 in a resting position, however in the case where an instrument is present, the one-way valve 1190 is opened, hence the need for a backup valve 1610. In other embodiments, the one-way valve 1190 maybe in the form of a duckbill valve or other one-way valves known in the art.

As described in FIGS. 4-7, the backup valve 1610 is made from an elastic member with a concentric hole 1611 and is capable of stretching to fit an expansion assembly 1500 or instrument 2511 inside and retracting back to its original hole cross-sectional area after the expansion assembly 1500 or instrument is removed, wherein the concentric hole 1611 comprises a cross-sectional area that is smaller than the cross-sectional area of members that would be inserted through it. The backup valve 1610 may be made of a thin polymer such as polyisoprene or silicone which can be made from sheet polymer where the hole 1611 can be punched.

Thus, in the resting position the one-way valve 1190 blocks the gas from escaping through the throughbore 1110, and when an instrument 2511 is present the one-way valve 1190 is opened and is no longer preventing the gas from escaping. The backup valve 1610 then stretches around the instrument with no gaps to create a gas-tight seal. This system is important in maintaining the insufflated gas in the patient since the one-way valve 1190 and backup valve 1610 would not work independently as the one-way valve 1190 would leak when instruments are inserted through it, and the backup valve 1610 would leak in the resting position when no instruments 2511 are inserted as it has a hole 1611 that does not close.

In an alternative embodiment, the backup valve 1610 seals around an obturator 1000 to prevent gas loss during initial entry in tissue.

In alternative embodiments of the backup valve 1610, it may be flat, floating, corrugated, wavy, layered or have any combination thereof that is known and described in the prior art.

With particular reference to FIG. 32C, an exemplary embodiment of a fixed diameter cannula 1520 is shown with an array of holes 1524 surrounding the region of the hollow cylindrical passage 1521 to allow for gas to enter and leave the fixed diameter cannula 1520, as well as a head 1535 with a valve system 1540 with a backup valve 1541 and a one-way valve 1542. In this embodiment the backup valve 1541 is a conical backup valve 1541, although in other embodiments, it may be flat, floating, corrugated, wavy, layered or have any combination thereof that is known and described in the prior art. In this embodiment, the one-way valve 1542 is shown as a cross-slit valve (herein referred to interchangeably), although in other embodiments it can be a duckbill valve or other known one-way valves known in the art.

The one-way valve 1542 in the head 1535 is similar to the cross-slit valve 1190 in the expandable cannula device 100 in terms of material properties, cross-slit shape and function, but is slightly smaller as it only needs to fit instruments less than the diameter of the fixed cannula device hollow passage 1521, whereas the one-way valve 1190 in the expandable cannula device 100 must fit the entire expansion assembly 1500 which has a larger diameter. It functions the same as it prevents gas from flowing through the valve 1542 in a resting position, however in the case where an instrument or obturator 1510 is present, the one-way valve 1542 is opened, hence the need for a conical backup valve 1541.

The conical backup valve 1541 has a central hole 1546 with an inner diameter that can be stretched to accommodate the obturator 1510 and a range of instrument sizes, and then retract back to its original inner diameter using its elastic properties. The conical backup valve 1541 may be an elastomer with a low shore hardness and high elongation and tensile strength, such as silicone or polyisoprene, and may be manufactured through injection or compression molding. The same way the flat backup valve 1610 prevents gas leakage from the throughbore 1110 of the expandable cannula device 100 when an instrument is present, the conical backup valve 1541 prevents gas leakage from the throughbore 1521 of the fixed diameter cannula 1520. However, the flat backup valve 1610 can only prevent gas leakage if the instrument is fully concentric, whereas the conical valve 1541 also has the capability to pivot with the instrument in order to prevent gas leakage at all times (further described in FIG. 34).

In alternative embodiments, the conical backup valve 1541 and one-way valve 1542 may have different geometries.

In an alternative embodiment, the valve system 1540 is removeable for rapid desufflation or specimen retrieval purposes, as described in FIG. 33.

With particular reference to FIG. 32D, in this exemplary embodiment, the fixed diameter cannula 1520 is shown within the expandable cannula device 100, where it has expanded to a larger diameter, and where gas can be transmitted through the stopcock 1280 and through the holes 1524 of the fixed diameter cannula 1520, allowing the gas to flow through the cylindrical passage 1521 of the fixed diameter cannula 1520 and into the enclosed region that is being operated on and vice versa. The elongate rigid members 1300 are not visible in this particular cross-section due to a different positioning relative to the stopcock 1280.

The holes 1524 are configured such that independent of the direction that the fixed diameter cannula 1520 is inserted into the expandable cannula device 100, the gas will be able to enter/leave through at least one of the holes 1524. In alternative embodiments, these holes 1524 may be dispersed in a different arrangement to affect gas flow.

In this embodiment, the single sealing elastic member 1740, backup valve 1610, one-way valve 1190 in the first housing 1100, the conical backup valve 1541 and a one-way valve 1542 in the fixed diameter cannula 1520 are all working collectively in order to prevent gas leakage. The single sealing elastic member 1740 prevents gas leakage in the retracted state and the expanded state (as described in FIGS. 15-17) from around the elongate rigid members 1300, between the concentric interfaces of the first housing 1100 and second housing 1200, and between the elongate rigid members 1300 and the second housing 1200 as it completely seals the expandable cannula device 100 from the tip 1330 of the elongate rigid members 1300 to the proximal surface 1140 of the first housing 1100.

When the fixed diameter cannula 1520 is entering the expandable cannula device 100, the fixed diameter cannula 1520 compromises the one-way valve's 1190 ability to seal the gas. However, simultaneously, it stretches the backup valve 1610 in the first housing 1100 as described in previous embodiments until it is fully inserted where the holes 1524 of the fixed diameter cannula 1520 are located distal to the stretched resistive member 1610 (backup valve), thereby the backup valve 1610 ensures that a gas seal is maintained for the entire assembly. This allows for expansion to occur with minimal gas loss which is important during surgery because it prevents the collapse of the insufflated working space during emergency expansion.

The conical backup valve 1541 and a one-way valve 1542 in the fixed diameter cannula 1520 then prevent gas leakage from the throughbore 1521 as described above, with and without instruments (described further in FIG. 34).

Turning to FIGS. 33A-33E, another exemplary embodiment of an expandable cannula device 100 is shown, generally similar to previous embodiments, although shown surrounded by a single sealing elastic member 1740 with a fixed diameter cannula 1520 inside, where the head 1535, which contains a conical backup valve 1541 and a one-way valve 1542, can be separated from the distal cylindrical body 1521 via a latch mechanism 1536 for the purpose of allowing the full diameter of the open passage 1521 for rapid desufflation of gas, which may be important during emergencies, if the CO2 pressure is too high which may cause embolisms for example, or for specimen retrieval 2522.

With particular reference to FIG. 33A-33D, in this exemplary embodiment, the head 1535 is released by twisting the latch mechanism 1536 counter-clockwise and guiding it upwards (proximally) and out of the cylindrical body 1521, and vice versa to place it back.

In alternative embodiments the latch mechanism 1536 could be any type of lock-release mechanisms such as snap-lock and push-release.

In an alternative embodiment, the latch 1536 may contain only a backup valve 1541, where the one-way valve 1542 remains in the cylindrical passage 1521.

Figure 33E:
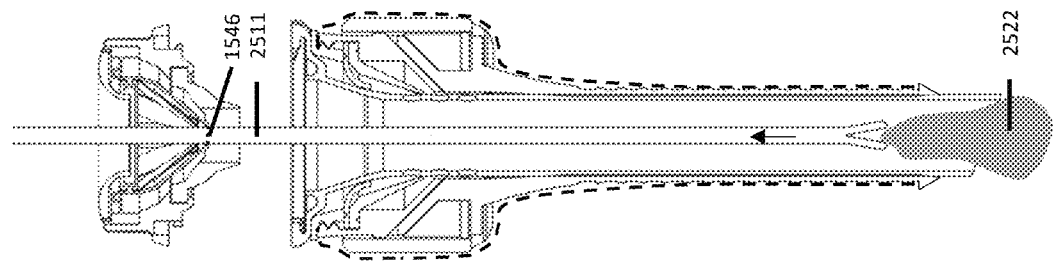
FIGS. 33A-33E are isometric and cross-sectional side views of an embodiment of the expandable cannula device in its expanded state with a fixed diameter cannula inserted therein, showing a one-way valve and a backup valve of the fixed diameter cannula contained in an attachably detachable housing that can be removed for rapid gas desufflation or specimen retrieval through the lumen of the fixed diameter cannula.
Figure 33D:
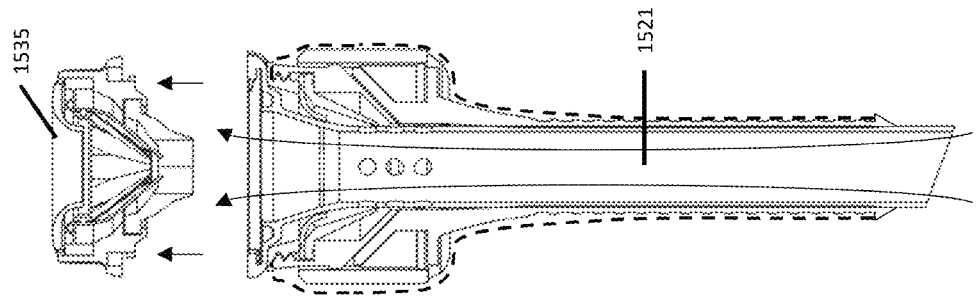
Figure 33C:
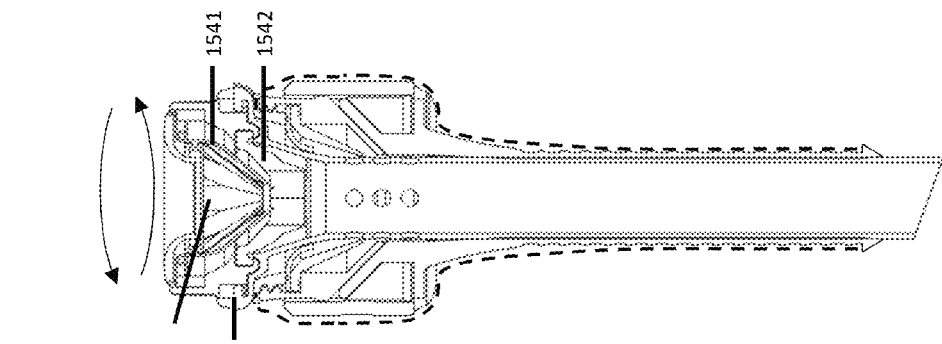
Figure 33B:
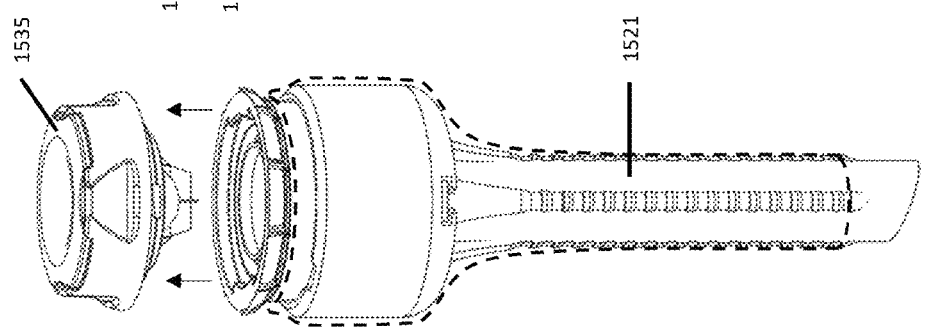
Figure 33A:
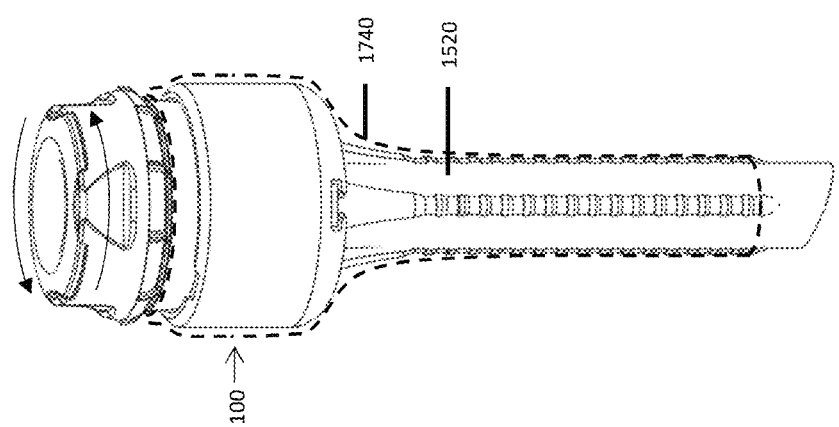

With particular reference to FIG. 33E, in this embodiment, if a user intends on removing a specimen 2522 that is larger than the inner diameter of the conical backup valve hole 1546, the head 1535 should be removed such that the specimen 2522 can be guided up through the cylindrical passage 1521 without interference from the valve system 1540. A user can insert an instrument 2511 such as a grasper through the lumen of the fixed diameter cannula 1520, grasp the specimen 2522 and pull it proximally through the cylindrical passage 1521, where the head 1535 can be separated and pulled proximally along with the instrument 2511 and specimen 2522.

Turning to FIGS. 34A-34D, another exemplary embodiment of an expandable cannula device 100 is shown, generally similar to previous embodiments, surrounded by a single sealing elastic member 1740 with a fixed diameter cannula 1520 inside, where the head 1535, contains a conical backup valve 1541, a serrated shield 1543 and a one-way valve 1542 compressed by a valve cap 1537 and where various instruments can be inserted through the cylindrical passage 1521 of the fixed diameter cannula 1520 while retaining a gas-tight seal.

With particular reference to FIG. 34A, in this exemplary embodiment, the serrated shield 1543 comprises a proximal cylindrical portion with a tongue that fits into a complimentary groove 1544 in the conical backup valve 1541, and a distal portion with non-elastic, serrated strips 1545 that overlap and form a conical passage that is complimentary to the conical backup valve 1541. The serrated shield 1543 acts as a barrier that prevents piercing of the softer elastic conical backup valve 1541 underneath when sharp or multi-pronged instruments are inserted (such as needles or clip applier instruments). The serrated strips 1545 are hinged proximally and push the elastic conical valve 1541 below them when such instruments are entered and prevent the conical backup valve 1541 from being punctured. The serrated shield 1543 can be made of an injection molded plastic with a high shore hardness that is flexible, such as polyethylene or polypropylene. In other embodiments, the serrated shield 1543 may be flat, floating, corrugated, wavy, layered or have any combination thereof that is known and described in the prior art.

As described in previous embodiments, the conical backup valve 1541 has a central hole 1546 with an inner diameter that can be stretched to accommodate both the smallest instruments 2511 and the largest instruments 2533, and then retract back to its original inner diameter using its elastic properties.

In alternative embodiments, the serrated shield 1543 can be attached to the conical backup valve 1541 in a variety of different ways such as with glue or epoxy, an opposite tongue and groove mechanism, or can be overmolded.

In this embodiment, a large instrument 2533 such as a clip applier is inserted into the fixed diameter cannula 1520 and is guided concentrically by the conical opening of the valve cap 1537 where it first comes into contact with the serrated shield 1543 which shields the conical backup valve 1541 and guides the instrument 2533 concentrically distally towards the hole opening 1546 of the conical backup valve 1541, where it then stretches the hole 1546 diameter to accommodate the instrument 2533 diameter and simultaneously create a tight seal, where gas cannot escape.

The serrated shield 1543 and conical backup valve 1541 and/or the instrument itself may be lubricated to reduce frictional forces when the instrument is being guided axially through the fixed diameter cannula 1520.

With particular reference to FIG. 34B, in this exemplary embodiment, the conical backup valve 1541 has a distal conical section 1547 and a proximal u-shaped section 1548 (shown in cross-section view, even though the shape profile extends circumferentially about the axis of the conical backup valve 1541) to allow for vertical motion in the z-direction and can pivot at different angles to accommodate small instruments being manipulated at different angles through the lumen of the fixed diameter cannula 1520.

In alternative embodiments, the u-shape 1548 geometry can differ, and can have at least one or a plurality of "u" sections. The "u" sections may be accordioned, zig-zag in shape or folded in various ways known in the art.

In this embodiment, a small instrument 2511 such as a grasper is inserted into the fixed diameter cannula 1520 and is guided concentrically similar to the large instrument 2533, where the hole 1546 diameter is stretched to accommodate the instrument 2511 while preventing gas loss.

With particular reference to FIGS. 34C-34D, in this exemplary embodiment, the small instrument 2512 is being manipulated in the fixed diameter cannula 1520 at an angle 2512, causing the conical backup valve 1541 to pivot, where one side (shown in this figure on the left) of the proximal u-shaped section 1548 extends out sufficiently 1551 causing the same side of the distal conical section 1547 to move distally, while the opposing side (shown in this figure on the right) of the proximal u-shaped section 1548 can bend further 1552 and gather under the valve cap 1537, causing the opposing side of the distal conical section 1547 to move proximally, such that the entire distal conical section 1547 of the conical backup valve 1541 and the complimentary serrated shield 1543 are at an angled position 1550 with little to no stretch.

Since the outer diameter of the small instrument 2511 is much smaller than the inner diameter of the fixed diameter cannula 1520, the small instrument 2511 can be manipulated at different angles, where the conical backup valve 1541 and serrated shield 1543 can pivot accordingly and where the hole 1546 remains tight around the small instrument 2511, preventing gas loss.

In alternative embodiments, the degree of the angled small instrument 2512 can be controlled by changing the length and inner diameter of the fixed diameter cannula 1520.

Turning to FIGS. 35A-35D, in this exemplary embodiment, the expansion assembly 1500 with an obturator 1510 and a fixed diameter cannula 1520 without the insufflation holes 1523 is shown on its own, where the expansion assembly 1500 can be used as its own cannula device, and in similar fashion to conventional trocars.

Figure 35D:
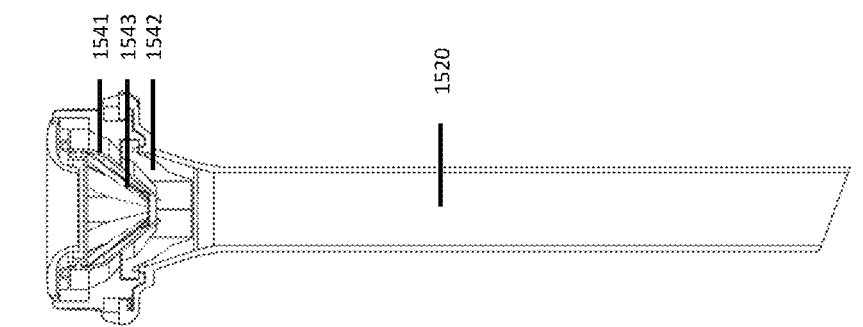
FIGS. 35A-35D are side and cross-sectional views of an alternative exemplary embodiment of a fixed diameter cannula and an obturator without holes in the walls of the fixed diameter cannula, wherein the components can be used as a conventional trocar or conventional optical trocar.
Figure 35C:
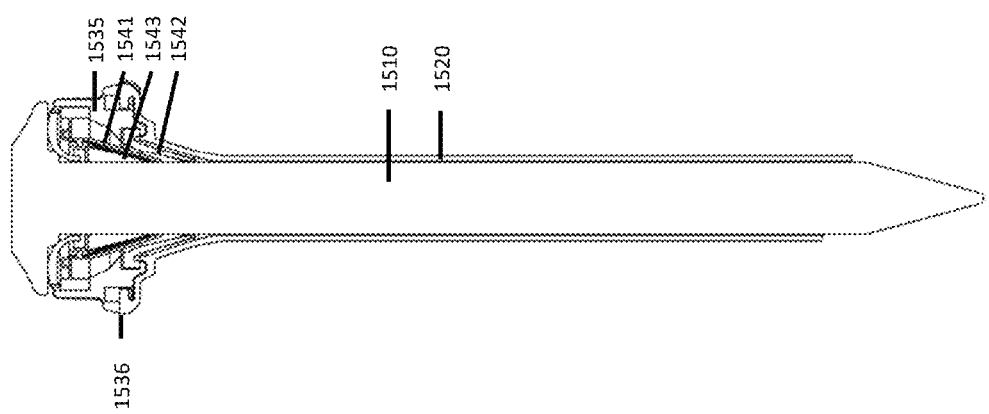
Figure 35B:
Figure 35A:
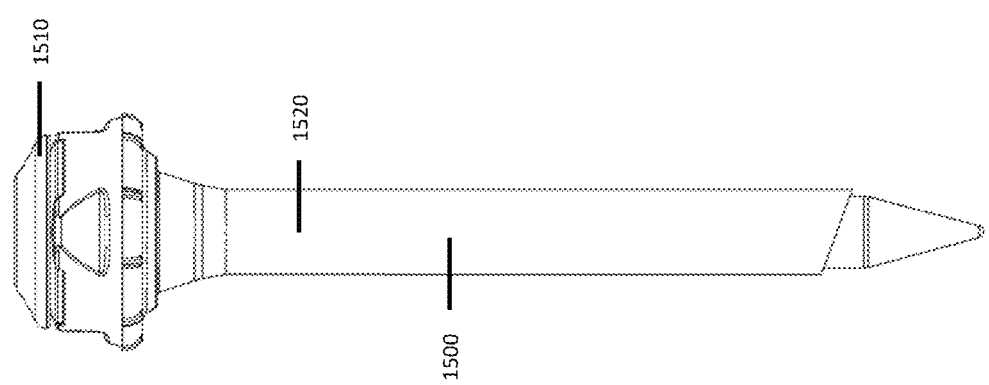

With particular reference to FIGS. 35A-35B, in this particular embodiment, the expansion assembly 1500 is shown without the insufflation holes 1523 which may be removed in the manufacturing process, may be covered via a removable tape, or may be plugged via known sealants.

In an alternative embodiment, the obturator 1510 can comprise an optical tip and hollow lumen that allows for entry of an endoscope, and can therefore be used as an "optical" obturator and the entire assembly 1500 can be used as an "optical trocar", which is known and would be appreciated by someone versed in the art.

In an alternative embodiment, the fixed diameter cannula may have surface modifications such as those on the elongate rigid members 1300 to provide better fixation.

With particular reference to FIGS. 35C-35D, in the exemplary embodiment a cross-sectional view is shown, where the head 1535 contains a conical backup valve 1541, serrated shield 1543 and one-way valve 1542 that can be detached and re-attached via a latch mechanism 1536 previously described, thereby preventing gas leakage through the fixed diameter cannula 1520.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A cannula device, comprising:
   a first housing defining a first throughbore aligned along a central axis;
   a second housing defining a second throughbore aligned with the first throughbore along the central axis, the second housing moveable in an axial direction along the central axis with respect to the first housing;
   a plurality of elongate members cooperatively defining a passage axially aligned with the first throughbore along the central axis between proximal ends and distal tips of the elongate members; and
   a plurality of guide elements on the proximal ends of the elongate members and the first and second housings configured to cooperate such that axial movement of the first housing with respect to the second housing along the central axis causes the proximal ends of the elongate members to move outwardly with respect to the central axis to move away from each other and increase a size of the passage,
   wherein the elongate members are configured such that, as the proximal ends move radially outwardly, if the distal tips are constrained, the elongate members define a tapered shape extending from the proximal ends towards the distal tips.

2. The cannula device of claim 1, further comprising:
   a resistive member within the first housing adjacent an inlet communicating with the first throughbore, the resistive member configured to receive a secondary device therethrough when the secondary device is inserted into the inlet and first throughbore and couple axial movement of the first housing to axial movement of the secondary device.

3. The cannula device of claim 1, further comprising:
an obturator including an elongate shaft defining an outer diameter; and an obturator tip on a distal end of the shaft having a cross-section larger than the outer diameter,
wherein the distal tips of the elongate members include interior tapers from the passage to an outlet of the elongate members sized to receive a portion of the obturator tip when the shaft is positioned within the passage, and
wherein the obturator tip comprises a proximal region that tapers outwardly from the distal end of the shaft and a distal region that tapers inwardly to a nose of the obturator tip, and wherein the tapers of the distal tips are shaped to receive the proximal region of the obturator tip such that the nose extends from the outlet of the elongate members, and wherein the distal tips of the elongate members provide a substantially smooth outer profile from the elongate members to the nose.

4. The cannula device of claim 1, further comprising:
a tubular membrane overlying the elongate members from the proximal ends at least partially towards the distal tips to provide a fluid-tight seal to prevent gas within the passage from escaping between the elongate members, and
wherein the membrane at least partially covers one or both of the first and second housings to prevent gas within the first and second throughbores from escaping through sidewalls of the first and second housings.

5. The cannula device of claim 4, wherein each distal tip comprises a tapered tip including a blunt proximal surface extending radially outwardly from the elongate member to an outer edge and a tapered distal surface tapering inwardly from the outer edge to an outlet of the passage, and wherein a distal end of the membrane is attached adjacent the blunt proximal surface.

6. The cannula device of claim 4, wherein a distal end of the membrane is permanently attached to the elongate members.

7. The cannula device of claim 1, wherein each of the elongate members comprises a plurality of engagement features on an outer surface thereof for engaging surrounding tissue to prevent migration of the cannula device.

8. The cannula device of claim 7, wherein each engagement feature includes a tapered distal surface and a blunt proximal surface.

9. The cannula device of claim 1, wherein one of the first and second housings comprises a mount for docking the cannula device to an arm of a robotic surgical system.

10. The cannula device of claim 1, wherein one of the first and second housings comprises a side port communicating with one or both of the first and second throughbores for connecting a source of pressurized gas for insufflation.

11. The cannula device of claim 1, wherein the guide elements are configured such that, as the first housing moves distally along the central axis relative to the second housing, the proximal ends of the elongate members move diagonally in a proximal direction relative to the first housing and radially outwardly relative to the second housing.

12. The cannula device of claim 1, wherein the guide elements comprise first tracks including inter-engaging first tongues and first guides oriented diagonally relative to the central axis, and the second housing and the elongate members comprise second tracks including second tongues and second guides such that axial movement of the first housing with respect to the second housing along the central axis causes the proximal ends of the elongate members to move outwardly with respect to the central axis and diagonally with respect to the first housing to move away from each other and increase the size of the passage.

13. The cannula device of claim 1, wherein axial movement of the first housing in a first direction with respect to the second housing along the central axis causes the proximal ends of the elongate members to move outwardly with respect to the central axis to move away from each other and increase a size of the passage, and, after expanding the passage, axial movement of the first housing in a second direction opposite the first direction causes the proximal ends of the elongate members to move inwardly to decrease a size of the passage.

14. The cannula device of claim 1, wherein the first and second housings include cooperating tongues and grooves that allow the first housing to move along the central axis relative to the second housing without rotation.

15. The cannula device of claim 1, further comprising one or more seals within the first housing for sealing the passage but allowing one or more devices to be inserted through the first throughbore into the passage.

16. The cannula device of claim 1, further comprising a first obturator configured to be inserted into the first throughbore, all the way through the unexpanded passage such that a tip of the first obturator is exposed prior to inserting the cannula device into tissue.

17. The cannula device of claim 16, wherein a second obturator with a larger diameter than the first obturator is configured to engage the first housing when inserted into the throughbore to cause the first housing to move distally relative to the second housing to move the elongate members away from each other and increase the size of the passage.

18. The cannula device of claim 17, wherein the first housing comprises a resistive member disposed across the first throughbore, and wherein the second obturator is configured to engage the resistive member to couple axial movement of the first housing to corresponding movement of the second obturator.

19. The cannula device of claim 1, wherein the elongate members define curved or tapered inner surfaces extending between the proximal ends and distal tips thereof at least partially defining the passage.

20. A system for introducing one or more instruments into a patient's body to perform a procedure, comprising:
  i. a cannula device comprising:
    a. first and second housings defining a throughbore along a central axis, the first housing moveable in an axial direction along the central axis with respect to the second housing;
    b. a plurality of elongate members extending distally from the first and second housings, the elongate members cooperatively defining a passage axially aligned with the throughbore along the central axis between proximal ends and distal tips of the elongate members; and
    c. a plurality of guide elements on the proximal ends of the elongate members and the first and second housings configured to cooperate such that axial movement of the first housing with respect to the second housing along the central axis causes the proximal ends of the elongate members to move outwardly with respect to the central axis to move away from each other and increase a size of the passage, the distal tips of the elongate members include interior tapers from the passage to an outlet of the elongate members such that the outlet has a larger diameter than the passage; and ii. an obturator comprising:
   a. an elongate shaft configured to be inserted through the throughbore into the passage and defining an outer diameter; and
   b. an obturator tip on a distal end of the shaft having a cross-section larger than the outer diameter, the tapers of the distal tips sized to receive a portion of the obturator tip when the shaft is positioned within the passage.

21. The system of claim 20, wherein the obturator tip comprises one of a sharpened nose or a dolphin nose or wherein the obturator tip comprises a Veress needle.

22. The system of claim 20, wherein the obturator comprises a proximal portion or handle that engages with a portion of the second housing to create a stop feature that controls the distance the obturator tip is able to advance distally in the passage.

23. A system for introducing one or more instruments into a patient's body to perform a procedure, comprising:
i. a cannula device comprising:
   a. first and second housings defining a throughbore along a central axis, the first housing moveable in an axial direction along the central axis with respect to the second housing;
   b. a plurality of elongate members extending distally from the first and second housings, the elongate members cooperatively defining a passage axially aligned with the throughbore along the central axis between proximal ends and distal tips of the elongate members; and
   c. a plurality of guide elements on the proximal ends of the elongate members and the first and second housings configured to cooperate such that axial movement of the first housing with respect to the second housing along the central axis causes the proximal ends of the elongate members to move outwardly with respect to the central axis to move away from each other and increase a size of the passage; and
ii. a secondary device sized for insertion through the throughbore into the passage, the secondary device configured to engage the first housing to cause the first housing to move distally relative to the second housing to move the elongate members away from each other and increase the size of the passage.

24. The system of claim 23, wherein the secondary device comprises:
an elongate tubular member comprising a proximal end, a distal end, and a lumen extending between the proximal and distal ends; and
an obturator received within the lumen such that a distal tip of the obturator extends beyond the distal end of the tubular member.

25. The system of claim 24, wherein one of the first and second housings comprises a side port communicating with one or both of the first and second throughbores, and wherein the tubular member comprises one or more openings in a sidewall thereof communicating with the lumen such that a source of pressurized gas connected to the side port can deliver gas through the one or more openings into the lumen.

26. The system of claim 24, further comprising one or more seals adjacent an inlet communicating with the throughbore for sealing the throughbore, and wherein the one or more seals comprise a one-way valve configured to prevent pressurized gas from escaping from the throughbore.

27. The system of claim 26, wherein the one or more seals further comprise a back-up valve adjacent the one-way valve configured to prevent pressurized gas from escaping from the throughbore when a secondary device is inserted therethrough.

28. The system of claim 23, wherein the secondary device comprises a first tubular member having a first outer diameter configured to move the elongate members away from one another to expand the passage to a first expanded configuration, the system further comprising a second tubular member having a second outer diameter larger than the first outer diameter, the second tubular member insertable into the cannula device after removing the first elongate member to expand the passage to a second expanded configuration.

29. The system of claim 23, wherein the first housing comprises a seal configured to prevent backflow of fluid proximally through the passage and the throughbore, and wherein the elongate member is configured to engage the seal to couple axial movement of the first housing to movement of the elongate member.

30. A method for performing a medical procedure within a subject's body, comprising:
providing a cannula device comprising first and second housings defining a throughbore along a central axis, the first housing moveable in an axial direction along the central axis with respect to the second housing, a plurality of elongate members extending distally from the first and second housings, the elongate members cooperatively defining a passage axially aligned with the throughbore along the central axis between proximal ends and distal tips of the elongate members; and
inserting distal tips of the elongate members through tissue into the subject's body;
inserting a first elongate tubular member through the throughbore and passage to move the first housing relative to the second housing along the central axis, thereby causing proximal ends of the elongate members to move outwardly with respect to the central axis to move the elongate members away from each other and increase a size of the passage; and
introducing one or more instruments through the first tubular member to perform the medical procedure within the subject's body.

* * * * *